United States Patent
Fogelman et al.

(10) Patent No.: US 7,250,304 B2
(45) Date of Patent: *Jul. 31, 2007

(54) FUNCTIONAL ASSAY OF HIGH-DENSITY LIPOPROTEIN

(75) Inventors: Alan M Fogelman, Beverly Hills, CA (US); Mohamad Navab, Los Angeles, CA (US); Susan Hama, Torrance, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/053,123

(22) Filed: Feb. 7, 2005

(65) Prior Publication Data

US 2005/0272162 A1    Dec. 8, 2005

Related U.S. Application Data

(60) Continuation-in-part of application No. 10/455,243, filed on Jun. 5, 2003, now Pat. No. 6,869,568, which is a division of application No. 09/541,468, filed on Mar. 31, 2000, now Pat. No. 6,596,544.

(51) Int. Cl.
   *G01N 33/92* (2006.01)
(52) U.S. Cl. .......... 436/71; 436/161; 436/164; 436/172; 436/173; 422/70; 422/82.05; 422/82.08; 435/11
(58) Field of Classification Search ............ 436/71, 436/161, 164, 172, 173, 63, 169, 170; 422/61, 422/70, 82.05, 55, 56, 82.08; 435/11, 4, 435/7.1; 600/481
See application file for complete search history.

(56) References Cited

U.S. PATENT DOCUMENTS

| | | | |
|---|---|---|---|
| 4,367,285 A | 1/1983 | Yamaguchi et al. | |
| H930 H | 6/1991 | Kato et al. | |
| 5,118,601 A | 6/1992 | Gruber | |
| 5,135,716 A | 8/1992 | Thakore | |
| 5,231,090 A | 7/1993 | Hsia et al. | |

(Continued)

FOREIGN PATENT DOCUMENTS

| | | |
|---|---|---|
| WO | WO 1994/023302 | 10/1994 |
| WO | WO 1996/018898 | 6/1996 |
| WO | 97/36927 | 9/1997 |
| WO | 98/20897 | 5/1998 |
| WO | WO 1998/059248 | 12/1998 |
| WO | 99/47566 | 9/1999 |

OTHER PUBLICATIONS

Navab et al. Journal of Lipid Research, vol. 42, 2001, pp. 1308-1317.*

(Continued)

*Primary Examiner*—Maureen M. Wallenhorst
(74) *Attorney, Agent, or Firm*—Beyer Weaver LLP; Tom Hunter

(57) ABSTRACT

This invention provides novel assays that are prognostic and/or diagnostic for atherosclerosis or risk of atherosclerosis. It was discovered that high density lipoprotein (HDL) or components thereof can prevent the oxidation of lipids (e.g., lipids present in LDLs) and can also repair (reduce) already oxidized lipids and thereby reduce the inflammatory response associated with and characteristic of atherosclerotic plaque formation. Moreover it was a discovery of this invention that individuals vary in the ability of their HDL to afford such protection. Thus an assay of HDL protective and/or repair activity provides a highly effective assay for risk of atherosclerosis and its associated pathologies and such assays are provided herein.

25 Claims, 23 Drawing Sheets

U.S. PATENT DOCUMENTS

| | | | |
|---|---|---|---|
| 5,458,896 A | 10/1995 | Porter | |
| 5,561,052 A | 10/1996 | Koike | |
| 5,989,803 A | 11/1999 | Tabas et al. | |
| 6,074,834 A * | 6/2000 | Slezak et al. | 435/7.1 |
| 6,265,147 B1 | 7/2001 | Mobley et al. | |
| 6,299,858 B1 | 10/2001 | Serbedzija et al. | |
| 6,309,888 B1 * | 10/2001 | Holvoet et al. | 436/71 |
| 6,362,236 B1 | 3/2002 | Aviram et al. | |
| 6,596,544 B1 * | 7/2003 | Fogelman et al. | 436/71 |
| 6,869,568 B2 * | 3/2005 | Fogelman et al. | 422/56 |

OTHER PUBLICATIONS

Anderson et al. (1987) "Cholesterol and Mortality: 30 Years of Follow-up From the Framingham Study." *Journal of the American Medical Association*, 257: 2176-2180.

Badimon et al. (1989), "High Density Lipoprotein Plasma Fractions Inhibit Aortic Fatty Streaks in Cholesterol-Fed Rabbits." *Laboratory Investigation*, 60:455-461.

Barr et al. (1951) "Protein-Lipid Relationships in Human Plasma: II. In Atherosclerosis and Related Conditions." *The American Journal of Medicine*, 11:480-493.

Bruce et al. (1998), "Plasma Lipid Transfer Proteins, High-Density Lipoproteins, and Reverse Cholesterol Transport." *Annual Review of Nutrition*, 18:297-330.

Chisolm (1991), "Antioxidants and Atherosclerosis: A Current Assessment." *Clinical Cardiology*, 14:125-130.

Christison et al. (1995), "Exchange of oxidized cholesteryl linoleate between LDL and HDL mediated by cholesteryl ester transfer protein." *Journal of Lipid Research*, 36:2017-2026.

Cyrus et al. (1999), "Disruption of the 12/15-lipooxygenase gene diminishes atherosclerosis in apo E-deficientmice." *The Journal of Clinical Investigation*, 103: 1487-1488.

Fluiter et al. (1999) "Scavenger Receptor BI Mediates the Selective Uptake of Oxidized Cholesterol Esters by Rat Liver." *Journal of Biological Chemistry*, 274:8893-8899.

Forte et al. (1995) "Recruitment of cell phospholipids and cholesterol by apolipoprotein-specific HDL that differ in size, phospholipid composition, and reactivity with LCAT." *Journal of Lipid Research* 36:148-157.

Garner et al. (1998) "Oxidation of High Density Lipoproteins: Formation of Methionine sulfoxide in apolipoproteins AI and AII is an early event that accompanies lipid peroxidation and can be enhanced by $\alpha$-Tocopherol." *Journal of Biological Chemistry*, 273:6080-6087.

Garner et al. (1998) "Oxidation of High Density of Lipoproteins: Evidence for Direct Reduction of Lipid Hydroperoxides by Methionine Residues of Apolipoproteins AI and AII." *Journal of Biological Chemistry*, 273:6088-6095.

Gofman et al. (1966) "Ischemic Heart Disease, Atherosclerosis, and Longevity." *Circulation*, 34:679-697.

Gordon et al. (1989), "High-Density Lipoprotein Cholesterol and Cardiovascular Disease: Four Prospective American Studies." *Circulation*, 79:8-15.

Hama (1997), "Apolipoprotein A-I Can Remove Lipid Molecules from Native LDL Rendering it Resistant to Oxidation by Cultured Artery Wall Cells." *Circulation*, 96:I-485, Abst.

Hama et al. (1998), "Circulating Low Density Lipoprotein-Minus Induces Marked Monocyte-endothelial Interactions." *Circulation*, 98:I-252, Abst.

Laplaud et al. (1998) "Paraoxonase as risk marker for cardovascular disease: Facts and Hypothesis" *Clin. Chem and Lab Med.* vol. 36, No. 7, pp. 431-441.

Mackness et al. (1995) "HDL, its enzymes and its potential to influence lipid peroxidation" *Atheroschlerosis*, 115, pp. 243-253.

Mackness et al. (1999) "Low serum paraoxonase: a risk factor for atherosclerotic disease?" *Chem-Biol Inter*, 119-120, pp. 389-397.

Metzler et al. (1999) Database BIOSIS on STN. "LDL stimulates mitogen-activated protein kinase phosphatase-1 expression, independent of LDL receptors, in vascular smooth muscle cells." *Arteriosclerosis, Thrombosis, and Vasular Biology*, 19(8): 1862-1871.

Miller and Miller (1975) "Plasma-High-Density-Lipoprotein Concentration and Development of Ischæmic Heart-Disease." *Lancet*, 1:16-19.

Navab et al. (1991) "Monocyte Transmigration Induced by Modification of Low Density Lipoprotein in Cocultures of Human Aortic Wall Cells Is due to Induction of Monocyte Chemotactic Protein 1 Synthesis and Is Abolished by High Density Lipoprotein," *The Journal of Clinical Investigation*, 88:2039-2046.

Navab et al. (1997) "Mildly Oxidized LDL Induces an Increased ApolipoproteinJ/Paraoxonase Ratio." *The Journal of Clinical Investigation*, 99: 2005-2019.

Navab et al. (2002) "Oxidized Lipids as Mediators of Coronary Heart Disease." *Current Opinion in Lipidology*, 13(4): 363-372.

Oram and Yokoyama (1996) "Apolipoprotein-mediated removal of cellular cholesterol and phospholids." *Journal of Lipid Research*, 37:2473-2491.

Parthasarathy (1994), In: *Free Radicals in the Enviornment, Medicine and Toxicology*, pp. 163-179. H. Nohl, H. Esterbauer, and C. Rice Evans, eds. Richelieu Press, London.

Parthasarathy (1994), "Mechanisms of Oxidation of LDL," pp. 91-119. In: *Modified Lipoproteins in the Pathogenesis of Atherosclerosis*, R.G. Landes Co., Austin, TX.

Phillips et al. (1998) "Mechanisms of high density lipoprotein-mediated efflux of cholesterol from cell plasma membranes." *Atheroscler*, 137 Supp: S13-S17.

Polidori et al. (1998) "Increased Plasma Levels of Lipid Hydroperoxides in Patients with Ischemic Stroke." *Free Rad. Biol. Med.*, 25:561-567.

Sevanian et al. (1997) "LDL is a lipid Hydroperoxide-enriched circulating lipoprotein." *Journal of Lipid Research*, 38:419-428.

Shwaery et al. (1999) "Preparation of Lipid Hydroperoxide-Free Low Density Lipo-proteins." *Meth. Enz.*, 300:17-23.

Sigari et al. (1997) "Fibroblasts That Overexpress 15-Lipoxygenase Generate Bioactive and Minimally Modified LDL." *Arteriosclerosis, Thrombosis and Vascular Biology*, 17:3639-3645.

Stampfer et al. (1991) "A Prospective Study of Cholesterol, Apolipoproteins, and the risk of mycocardial infarction." *The New England Journal of Medicine*, 325:373-381.

Thomas and Jackson (1991) "Lipid Hydroperoxide Involvement in Copper-Dependent and Independent Oxidation of Low Density Lipoproteins." *The Journal of Pharmacology and Experimental Therapeutics*, 256:1182-1188.

Thomas et al. (1994) "Involvement of Pre-existing Lipid Hydroperoxides in $Cu^{2+}$-Stimulated Oxidation of Low-Density Lipoproteind[1]." *Archives of Biochemistry and Biophysics*, 315:244-254.

Van de Vijver et al. (1998) "LDL oxidation and extent of coronary atherosclerosis" *Arteriosclerosis, Thrombosis and Vascular Biology*, 18: 193-199.

Vega and Grundy (1996) "Hypoalphalipoproteinemia (low high density lipoprotein) as a risk factor for coronary heart disease." *Current Opinion in Lipidology*, 7:209-216.

Watson et al. (1995) "Structural Identification of a Novel Pro-inflammatory Epoxyisoprostane Phospholipid in Mildly Oxidized Low Density Lipoprotein." *Journal of Clinical Investigation*, 95:774-782.

Watson et al. (1999) "Effect of Platelet Activation Factor-Acetylhydrolase on the Formation and Action of Minimally Oxidized Low Density Lipoprotein." *The Journal of Biological Chemistry*, 274:24787-24798.

Witztum (1994) "The oxidation hypothesis of atherosclerosis." *Lancet*, 344:793-795.

Witztum and Steinberg (1991) "Role of Oxidized Low Density Lipoprotein in Atherogenesis." *The Journal Of Clinical Investigation*, 88:1785-1792.

Bauer et al (1982) "SMS 2001-995: A Very Potent and Selective Octapeptide Analogue of Somatostatin with Prolonged Action" *Life Sciences* 31:1133-1140.

Boffelli et al (1997) "Reconstitution and Further Characterization of the Cholesterol Transport Activity of the Small-Intestinal Brush Border Membrane" Biochemisty 36:10784-10792.

Brouillette et al (2001) "Structural Models of Human Apolipoprotein A-I : A Critical Analysis and Review" Biochemical at Biophysical Acta 55753:1-44.

Datta et al (2001) "Effects of Increasing Hydrophobicity on the Physical=Chemical and Biological Properties of a Class A Amphipathic Helical Peptide." J. Lipid Research 42:1096-1104.

Diederich et al (2001) "Apolipoprotein Al and HDL3 Inhibit Spreading of Primary Human Monocytes through a Mechanism that Involves Cholesterol Depletion and Regulation of CD42" Atherosclerosis 159:313-324.

Dooley et al (1984) "An All D-Amino Acid Opioid Peptide with Central Analgesic Activity from a Combinatorial Library" Science 2019-2022.

Duff (1995) Mitogen-activated Protein (MAP) Knase Is Regulated by the MAP Kinase Phosphatase (MKP-1) in Vascular Smooth Muscles Cells. Journal of Biological Chemistry vol. 270 No. 13 pp. 7161-7166.

Fricker et al (1995) "Eternal Absorption of Octreotide: Modulation of Intestinal Permeability by Distinct Carbohydrates" The Journal of Pharmacology and Experimental Therapeutics 274:826-832.

Fuessl et al (1987) "Oral Absorption of the Somatostatin Analogue SMS 201-995: Theoretical and Practical Implications" Clinical Science 72:225-257.

Garfinkel et al (2002) "Influenza Vaccines Pilot Study in Acute Coronary Syndromes and Planned Percutaneous Coronary Interventions. The FLU Vaccination Acute Coronary Syndromes (FLUVACS) Study" Circulation 105:2143-2147.

Hamase et al (2001) "Determination of Free D-Proline and D-Leucine in the Brains of Mutant Mice Lacking D-Amino Acid Oxidase Activity" Analytical Biochemistry 298:253-258.

Hardy et al (2001) "An Automated High-Performance Liquid Chromatography Procedure for the Quantitation of L-and D-Amino Acids by Means of Stepwise Precolumn Derivatization" Analytical Biochemistry 291:297-299.

Hyka et al (2001) "Apolipoprotein A-I Inhibits the Production of Interleukin-l and Tumor Necrosis Factor by Blocking Contact-Mediated Activation of Monocytes by T Lymphycytes" Blood 97:2381-2389.

Jones et al (1992) "Computer Programs to Identify and Classify Amphipatic Helical Domains" Journal of Lipid Research 33:287-296.

Kullman et al (1999) "Evaluation of the Enantiomeric Composition of Amino Acids in Tobacco" Chirality 11:669-673.

Lai et al (1996) "Mitogen-activated Protein Kinase Phosphatase-1 in Rat Arterial Smooth Muscle Cell Proliferation" Journal of Clinical Invest vol. 98 No. 7 pp. 1560-1567.

Lundin et al (1986) "Absorption of Intragastrically Administered DDAVP in Conscious Dogs" Life Sciences 38:703-709.

Merrifield et al (1995) "Retro and Retroenantio Analogs of Cecropin-Melittin Hybrids" Proc Natl Acad Aci USA 92:3449-3453.

Navab et al (2002) "Oral Administration of an Apo A-I Mimetic Peptide Synthesized from D-Amino Acids Dramatically Reduces Atherosclerosis in Mice Independent of Plasma Cholesterol" Circulation 105:290-292.

Navab et al "A Cell-Free Assay for Detecting HDL that is Dysfunctional In Preventing the Formation of or inactivation Oxidized Phospholipids" Journal of Lipid Research vol 42, 2001, pp. 1308-1317.

Owens et al (1990). "Apolipoprotein A-I and its Amphiapathic Helix Peptide Analogues Inhibit Human Immunodeficiency Virus-Induced Syncytium Formation" J. Clin. Invest 86:1142-1150.

Panizzutti et al (2001) "A New Strategy to Decrease N-Methyl-D-aspartate (NMDA) Receptor Coactivation: Inhibition of D-Serine Synthesis by Converting Serine Racemase into an Eliminase" PNAS 98:5394-5299.

Pappenheimer et al (1994) "Intestinal Absorption and Excretion of Octapeptides Composed of D Amino Acids" Proc Natil Acad Sci USA 91:1942-1945.

Peng et al (2001) "Effects of L-glutamate, D-aspartate, and monesnsin on Glycolic and Oxidative Glucose Metabolism in Mouse Astrocyte Cultures: Further Evidence that Glutamate Uptake is Metabolically Driven by Oxidative Metabolism" Neurochemistry International 38:437-443.

Reddy et al (2001) "Mitogen-activated Protein Kinase Phosphatase 1 Activity Is Necessary for Oxidized Phospholipids to Induce Monocyte Chemotactic Activity in Human Aortic Endothelial Cells," Journal of Biological Chemistry vol. 276, No. 20pp. 17030-17035.

Segrest et al (1992) "The Amphipathic Helix in the Exchangeable Apolipoproteins: A Review of Secondary Structure and Function" J. Lipid Research 33:141-166.

Singh et al (2000) Innate Defenses Against Viraemia Rev Med Virol 10:395-403.

Srinivas Et al (1990) "Antiviral Effects of Apolipoprotein A-I and its Synthetic Amphipathic Peptide Analogs" Virology 176:48-57.

International Search Report of May 20, 2001 PCT/US01/10590.

EPO Search Report of Jul. 30, 2004, Application No. EP01923023.

* cited by examiner

FUNCTIONAL ASSAY OF HIGH-DENSITY LIPOPROTEIN

CROSS-REFERENCE TO RELATED APPLICATIONS

This application is a Continuation-in-Part of U.S. Ser. No. 10/455,243, now U.S. Pat. No. 6,869,568, filed on Jun. 5, 2003, which is a Divisional of U.S. Ser. No. 09/541,468, now U.S. Pat. No. 6,596,544, filed Mar. 31, 2000, all of which are incorporated herein by reference in their entirety for all purposes.

STATEMENT AS TO RIGHTS TO INVENTIONS MADE UNDER FEDERALLY SPONSORED RESEARCH AND DEVELOPMENT

This invention was made with Government support under Grant No: HL30568, awarded by the National Institutes of Health. The Government of the United States of America may have certain rights in this invention.

FIELD OF THE INVENTION

This invention relates to the diagnosis of atherosclerosis. In particular this invention provides improved assays

BACKGROUND OF THE INVENTION

Cardiovascular disease is a leading cause of morbidity and mortality, particularly in the United States and in Western European countries. Several causative factors are implicated in the development of cardiovascular disease including hereditary predisposition to the disease, gender, lifestyle factors such as smoking and diet, age, hypertension, and hyperlipidemia, including hypercholesterolemia. Several of these factors, particularly hyperlipidemia and hypercholesteremia (high blood cholesterol concentrations) provide a significant risk factor associated with atherosclerosis.

Cholesterol is present in the blood as free and esterified cholesterol within lipoprotein particles, commonly known as chylomicrons, very low density lipoproteins (VLDLs), low density lipoproteins (LDLs), and high density lipoproteins (HDLs). Concentration of total cholesterol in the blood is influenced by (1) absorption of cholesterol from the digestive tract, (2) synthesis of cholesterol from dietary constituents such as carbohydrates, proteins, fats and ethanol, and (3) removal of cholesterol from blood by tissues, especially the liver, and subsequent conversion of the cholesterol to bile acids, steroid hormones, and biliary cholesterol.

Maintenance of blood cholesterol concentrations is influenced by both genetic and environmental factors. Genetic factors include concentration of rate-limiting enzymes in cholesterol biosynthesis, concentration of receptors for low density lipoproteins in the liver, concentration of rate-limiting enzymes for conversion of cholesterols bile acids, rates of synthesis and secretion of lipoproteins and gender of person. Environmental factors influencing the hemostasis of blood cholesterol concentration in humans include dietary composition, incidence of smoking, physical activity, and use of a variety of pharmaceutical agents. Dietary variables include amount and type of fat (saturated and polyunsaturated fatty acids), amount of cholesterol, amount and type of fiber, and perhaps amounts of vitamins such as vitamin C and D and minerals such as calcium.

As indicated above, high blood cholesterol concentration is one of the major risk factors for vascular disease and coronary heart disease in humans. Elevated low density lipoprotein cholesterol ("LDL-cholesterol") and total cholesterol are directly related to an increased risk of coronary heart disease (see, e.g., Anderson et al. (1987) JAMA, 257:2176-2180).

Although high levels of total cholesterol and LDL-cholesterol are risk factors in developing atherosclerosis and vascular diseases, a deficiency of high density lipoprotein cholesterol (hereafter "HDL-cholesterol") has recently been recognized as a risk factor for developing these conditions. Several clinical trials support a protective role of HDL-cholesterol against atherosclerosis. A study has shown that for every 1-mg/dl increase in HDL-cholesterol in the blood, the risk for coronary vascular disease is decreased by 3% in women (see, Gordon et al. (1989) Circulation, 79: 8-15).

It is widely believed that HDL is a "protective" lipoprotein (Vega and Grundy (1996) Curr. Opin. Lipidology, 7, 209-216) and that increasing plasma levels of HDL may offer a direct protection against the development of atherosclerosis. Numerous studies have demonstrated that both the risk of coronary heart disease (CHD) in humans and the severity of experimental atherosclerosis in animals are inversely correlated with serum HDL cholesterol (HDL-C) concentrations (Russ et al. (1951) Am. J. Med., 11: 480-493; Gofman et al. (1966) Circulation, 34: 679-697; Miller and Miller (1975) Lancet, 1: 16-19; Gordon et al. (1989) Circulation, 79: 8-15; Stampfer et al. (1991) N. Engl. J. Med., 325: 373-381; Badimon et al. (1989) Lab. Invest., 60: 455-461).

While HDU LDL ratios have appear to provide a good marker for risk of atherosclerosis and heart disease on a population level, HDL and/or LDL measurements have proven to be poor prognostic indicators at an individual level. In particular individuals with high HDL:LDL ratios have been observed with severe atherosclerosis, while conversely, individuals with very low HDL:LDL ratios have been identified with no evidence of atherosclerosis.

SUMMARY OF THE INVENTION

This invention provides novel assays that are prognostic and/or diagnostic for atherosclerosis or risk of atherosclerosis. The assays are based, in part, on elucidation of a mechanism by which HDL affords protection against plaque formation. In particular, it was a discovery of this invention that HDL or components can prevent the oxidation of lipids (e.g., lipids present in LDLs) and can also repair (reduce) already oxidized lipids and thereby reduce the inflammatory response associated with and characteristic of atherosclerotic plaque formation. Moreover it was a discovery of this invention that individuals vary in the ability of their HDL to afford such protection. Thus an assay of HDL protective and/or repair activity provides a highly effective assay for risk of atherosclerosis and its associated pathologies.

Thus, in certain embodiments, this invention provides methods of evaluating the risk for atherosclerosis in a mammal by evaluating the ability of the animal's HDL to repair (reduce) oxidized phospholipids. The methods can involve providing a biological sample from the mammal where the sample comprises a high-density lipoprotein (HDL) or a component thereof (e.g., apo A-I, paraoxonase, platelet activating factor acetylhydrolase, etc.), contacting the high-density lipoprotein with an oxidized phospholipid; and measuring a change in the amount of oxidized or non-oxidized phospholipid where the reduction or absence of change in the amount of oxidized phospholipid indicates the mammal is at risk for atherosclerosis. In certain embodiments, the oxidized phospholipids is provided in combination with low density lipoprotein (LDL).

Suitable oxidized phospholipids include an oxidized phospholipid that causes a monocytic reaction. Certain preferred phospholipids include, but are not limited to the oxidized form of lipids selected from the group consisting of 1-palmitoyl-2-arachidonoyl-sn-glycero-3-phosphorylcholine (Ox-PAPC), 1-palmitoyl-2-oxovaleroyl-sn-glycero-3-phosphorylcholine (POVPC), 1-palmitoyl-2-glutaroyl-sn-glycero-3-phosphorylcholine (PGPC), 1-palmitoyl-2-epoxyisoprostane-sn-glycero-3-phosphorylcholine (PEIPC), 1-stearoyl-2-arachidonoyl-sn-glycero-3-phosphorylcholine (SAPC), 1-stearoyl-2-oxovaleroyl-sn-glycero-3-phosphorylcholine (SOVPC), 1-stearoyl-2-glutaroyl-sn-glycero-3-phosphorylcholine (SGPC), 1-stearoyl-2-epoxyisoprostane-sn-glycero-3-phosphorylcholine (SEIPC), 1-stearoyl-2-arachidonyl-sn-glycero-3-phosphorylethanolamine (Ox-SAPE), 1-stearoyl-2-oxovaleroyl-sn-glycero-3-phosphorylethanolamine (SOVPE), 1-stearoyl-2-glutaroyl-sn-glycero-3-phosphorylethanolamine (SGPE), and 1-stearoyl-2-epoxyisoprostane-sn-glycero-3-phosphorylethanolamine(SEI PE). In one particularly preferred embodiment, the oxidized phospholipid is a component of (present in) a low density lipoprotein.

The oxidized phospholipid (or reduced phospholipid) can be determined by any convenient method. Such methods include, but are not limited to mass spectrometry, liquid chromatography, thin layer chromatography, fluorimetry, radioisotope detection, antibody detection, and detecting a signal from a label that indicates an oxidized phospholipid. Fluorescent labels (e.g., 2',7'-dichlorodihydrofluorescine diacetate, rhodamine, cis-parinaric acid, NBD, cis-parinaric acid cholesteryl ester, diphenylhexatriene propionic acid), and dichlorofluorescein diacetate (DCFH-DA), are particularly preferred.

In certain embodiments, the detecting comprises a chromatography method selected from the group consisting of fast performance liquid chromatography (FPLC).

Preferred samples include fluid or tissue samples containing HDL. Particularly preferred samples include, but are not limited to whole blood or blood fractions (e.g., serum, plasma, etc.).

The sample can be used directly, or alternatively, HDL may be isolated from the sample. Thus, for example, in certain embodiments, magnetic bead reagents are used to remove non-HDL cholesterol. The change and/or amount of oxidized phospholipid can be determined relative to known levels for the subject population and/or by reference to various controls. Such controls include, but are not limited to the change in amount of oxidized phospholipid produced by contacting the oxidized phospholipid with HDL known to reduce levels of oxidized phospholipid, the change in amount of oxidized phospholipid produced by contacting the oxidized phospholipid with HDL known to be deficient in the ability to reduce levels of oxidized phospholipid, and the change in phospholipid produced in the same experiment run without HDL or with HDL present at a lower concentration.

The mammal can be a human or a non-human. Particularly preferred mammals include, but are not limited to humans, non-human primates, canines, felines, murines, bovines, equines, porcines, and lagomorphs. The human may be a human diagnosed as having a low HDL:LDL ratio and/or as being at risk for atherosclerosis.

In another embodiment this invention provides methods of evaluating the risk for atherosclerosis in a mammal by measuring the ability of the mammal's HDL to protect lipids from oxidation. The methods preferably involve providing a biological sample from the mammal where the sample comprises a high-density lipoprotein (HDL), contacting the high density lipoprotein with a phospholipid, subjecting the phospholipid to oxidizing conditions; and measuring a change in the amount of oxidized or non-oxidized phospholipid where a change in the amount of oxidized or non-oxidized phospholipid indicates the mammal is at risk for atherosclerosis. In a preferred embodiment the phospholipid is provided in a low density lipoprotein (LDL). Particularly preferred phospholipids are phospholipids that, when oxidized, cause a monocytic reaction. Such phospholipids include, but are not limited to 1-palmitoyl-2-arachidonoyl-sn-glycero-3-phosphorylcholine (Ox-PAPC), 1-palmitoyl-2-oxovaleroyl-sn-glycero-3-phosphorylcholine (POVPC), 1-palmitoyl-2-glutaroyl-sn-glycero-3-phosphorylcholine (PGPC), 1-palmitoyl-2-epoxyisoprostane-sn-glycero-3-phosphorylcholine (PEIPC), 1-stearoyl-2-arachidonoyl-sn-glycero-3-phosphorylcholine (SAPC), 1-stearoyl-2-oxovaleroyl-sn-glycero-3-phosphorylcholine (SOVPC), 1-stearoyl-2-glutaroyl-sn-glycero-3-phosphorylcholine (SGPC), 1-stearoyl-2-epoxyisoprostane-sn-glycero-3-phosphorylcholine (SEIPC), 1-stearoyl-2-arachidonyl-sn-glycero-3-phosphorylethanolamine (Ox-SAPE), 1-stearoyl-2-oxovaleroyl-sn-glycero-3-phosphorylethanolamine (SOVPE), 1-stearoyl-2-glutaroyl-sn-glycero-3-phosphorylethanolamine (SGPE), and 1-stearoyl-2-epoxyisoprostane-sn-glycero-3-phosphorylethanolamine(SEI PE).

In certain embodiments the phospholipid is subjected to oxidizing conditions by contacting the phospholipid with an oxidizing agent, e.g., an agent selected from the group consisting of hydrogen peroxide, 13(S)-HPODE, 15(S)-HIPETE, HPODE, HPETE, HODE, and HETE. The detection of oxidized or reduced phospholipid can be by any convenient method, with the methods described herein (e.g., described above) being most preferred. Particularly preferred detection labels include but are not limited to 2',7'-dichlorodihydrofluorescine diacetate, rhodamine, cis-parinaric acid, NBD, cis-parimic acid cholesteryl ester, and diphenylhexatisene propionic acid. Preferred samples are as describe above and herein. In the case of blood or blood fraction samples, the method may involve direct use of the blood or blood fraction or isolation of HDL from the blood or blood fraction.

The change and/or amount of oxidized phospholipid can be determined relative to known levels for the subject population and/or by reference to various controls. Such controls include, but are not limited to the change in amount of oxidized phospholipid produced by contacting the oxidized phospholipid with HDL known to reduce levels of oxidized phospholipid, the change in amount of oxidized phospholipid produced by contacting the oxidized phospholipid with HDL known to be deficient in the ability to reduce levels of oxidized phospholipid, and the change in phospholipid produced in the same experiment run without HDL or with HDL present at a lower concentration.

Preferred mammals assayed according to the methods of this invention include humans and non humans, e.g., as described above. Particularly preferred subjects are humans diagnosed as having a low HDL:LDL ratio and/or as being at risk for atherosclerosis.

In still another embodiment this invention provides kits for evaluating the risk for atherosclerosis in a mammal. The kits preferably comprise a container containing one or more oxidized or non-oxidized phospholipids, and instructional materials providing protocols for the assays described herein. The kits optionally include a label for detecting oxidized phospholipid and/or optionally, an oxidizing agent (e.g., 13(S)-HPODE, 15(S)-HPETE, HPODE, HPETE, HODE, and HETE). In certain embodiments, the kit comprises a container containing one or one or more oxidized phospholipids, and the instructional materials describe assaying HDL for the ability to reduce oxidized lipids. In other embodiments, the kit comprises a container containing one or more non-oxidized (reduced) phospholipids, and the instructional materials describe assaying HDL for the ability to protect lipids (e.g., lipids in LDL) from oxidation.

In still another embodiment, this invention provides test devices for the assays of this invention. The test device preferably comprises an inert porous substrate having a receiving area, the porous substrate being juxtaposed to a transport medium, the transport medium being juxtaposed to a test membrane comprising a reagent for detecting an oxidized lipid. The test device optionally includes a non-oxidized lipid and an oxidizing agent or an oxidized phospholipid.

Definitions

The terms "low density lipoprotein" or "LDL" are defined in accordance with common usage of those of skill in the art. Generally, LDL refers to the lipid-protein complex which when isolated by ultracentrifugation is found in the density range d=1.019 to d=1.063.

The terms "high density lipoprotein" or "HDL" are defined in accordance with common usage of those of skill in the art. Generally "HD" refers to lipid-protein complex which when isolated by ultracentrifugation is found in the density range of d=1.063 to d=1.21.

The term "Group I HDL" refers to a high density lipoprotein or components thereof (e.g., apo A-I, paraoxonase, platelet activating factor acetylhydrolase, etc.) that reduce oxidized lipids (e.g., in low density lipoproteins) or that protect oxidized lipids from oxidation by oxidizing agents.

The term "Group II HDL" refers to an HDL that offers reduced activity or no activity in protecting lipids from oxidation or in repairing (e.g., reducing) oxidized lipids.

The term "HDL component" refers to a component (e.g., molecules) that comprises a high density lipoprotein (HDL). Assays for HDL that protect lipids from oxidation or that repair (e.g., reduce oxidized lipids) also include assays for components of HDL (e.g., apo A-I, paraoxonase, platelet activating factor acetylhydrolase, etc.) that display such activity.

A "monocytic reaction" as used herein refers to monocyte activity characteristic of the "inflammatory response" associated with atherosclerotic plaque formation. The monocytic reaction is characterized by monocyte adhesion to cells of the vascular wall (e.g., cells of the vascular endothelium), and/or chemotaxis into the subendothelial space, and/or differentiation of monocytes into macrophages.

The term "absence of change" when referring to the amount of oxidized phospholipid refers to the lack of a detectable change, more preferably the lack of a statistically significant change (e.g., at least at the 85%, preferably at least at the 90%, more preferably at least at the 95%, and most preferably at least at the 98% or 99% confidence level). The absence of a detectable change (e.g., when scoring a positive result for Group I HDL) can also refer to assays in which oxidized cholesterol level changes, but not as much as in the absence of the HDL or with reference to other positive or negative controls.

The following abbreviations may be used herein: PAPC: L-α-1-palmitoyl-2-arachidonoyl-sn-glycero-3-phosphocholine; POVPC: 1-palmitoyl-2-(5-oxovaleryl)-sn-glycero-3-phosphocholine; PGPC: 1-palmitoyl-2-glutaryl-sn-glycero-3-phosphocholine; PEIPC: 1-palmitoyl-2-(5,6-epoxyisoprostane $E_2$)-sn-glycero-3-phsophocholine; ChC18:2: cholesteryl linoleate; ChC18:2—OOH: cholesteryl linoleate hydroperoxide; DMPC: 1,2-ditetradecanoyl-rac-glycerol-3-phosphocholine; PON: paraoxonase; HPF: Standardized high power field; PAPC: L-α-1-palmitoyl-2-arachidonoyl-sn-glycero-3-phosphocholine; POVPC: 1-palmitoyl-2-(5-oxovaleryl)-sn-glycero-3-phosphocholine; PGPC: 1-palmitoyl-2-glutaryl-sn-glycero-3-phosphocholine; PEIPC: 1-palmitoyl-2-(5,6-epoxyisoprostane $E_2$)-sn-glycero-3-phsophocholine; PON: paraoxonase; HPF: Standardized high power field; BL/6: C57BL/6J; C3H:C3H/HeJ.

DETAILED DESCRIPTION

Figure 1:
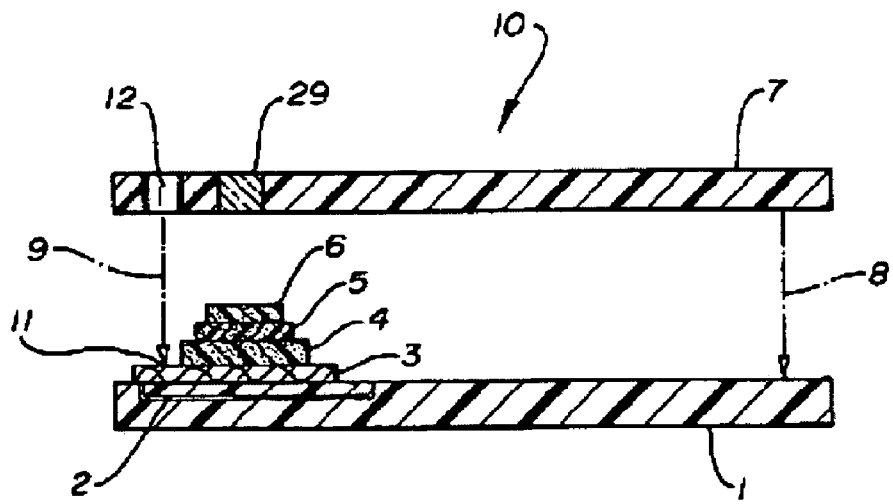
FIG. 1 illustrates one embodiment of a test for assaying activity of HDL in protecting lipids from oxidation.

This invention provides novel assays that are prognostic and/or diagnostic for atherosclerosis or risk of atherosclerosis. The assays are based, in part, on elucidation of a mechanism by which HDL affords protection against plaque formation.

It has been noted that freshly isolated low density lipoprotein (LDL) contains lipid hydroperoxides (Sevanian et al. (1997) *J. Lipid Res.*,38: 419-428). We believe that LDL oxidation requires that the LDL be "seeded" with reactive species before it can be oxidized. The presence of oxidized lipids results in an "inflammatory response; the induction of monocyte binding, chemotaxis, and differentiation into macrophages. This process underlies plaque formation characteristic of atherosclerosis.

More particularly, without being bound to a theory, it is believed that the biologically active lipids in mildly oxidized LDL (m/z 594, 610, and 828) are formed in a series of three steps. The first step is the seeding of LDL with products of the metabolism of linoleic and arachidonic acid as well as with cholesteryl hydroperoxides. The second step involves trapping of LDL in the subendothelial space and the delivery to this trapped LDL of additional reactive oxygen species derived from nearby artery wall cells. The third step is the non-enzymatic oxidation of LDL phospholipids that occurs when a critical threshold of "seeding molecules" (e.g., 13-hydroperoxyoctadecadienoic acid [13(S)-HPODE] and 15-hydroperoxyeicosatetrenoic acid [15(S)-HPETE ]) is reached in the LDL. This results in the formation of specific oxidized lipids (m/z 594,610,828) that induce monocyte binding, chemotaxis, and differentiation into macrophages. We present evidence which indicates that when the "seeding molecules" reach a critical level, they are approximately two orders of magnitude more potent than hydrogen peroxide in causing the non-enzymatic oxidation of a major LDL phospholipid, 1-palmitoyl-2-arachidonoyl-sn-glycero-3-phosphocholine (PAPC) resulting in the formation of the three biologically active oxidized phospholipids (m/z 594, 610, and 828) (Watson et al. (1997) *J Biol Chem* 272:13597-13607; Watson et al. (1999) *J Biol Chem* 274:24787-24798).

The experiments described herein also indicate that, in contrast to the case for normal HDL, BDL taken from a relatively rare subset of patients, those with angiographically documented coronary artery disease who had perfectly normal levels of LDL-cholesterol, HDL-cholesterol, and triglycerides and who were not diabetic and who were not taking hypolipidemic medications did not protect LDL against oxidation by human artery wall cells and failed to inhibit the biologic activity of oxidized PAPC.

Thus, we have identified two sets of subjects: 1) Those subjects whose HDL affords protection against the formation of oxidized lipids and/or reduces or eliminates these oxidized lipids and hence protects against the associated inflammatory processes of atherosclerosis (designated herein as Group I HDLs); and 2) Those subjects whose HDL does not afford protection against the formation of oxidized lipids, and/or does not reduce or eliminate these oxidized lipids, particularly oxidized LDL (designated herein as Group II HDLs). It is believed that the differences in the HDL activity between these two sets of subjects accounts, at least in part, for the lack of predictability offered by conventional HDL assays. It is also believed that subjects in this second subset are at considerably greater risk for atherosclerosis and its associated complications. An assay that distinguishes between these two sets of subjects (i.e., between subjects having Group I HDLs and subjects having Group II HDLs) is of significant prophylactic and diagnostic value.

As a prophylactic assay, the methods of this invention allow identification of individuals of particularly high risk for atherosclerosis. Upon such identification, such subjects can adopt more frequent testing, dietary adjustments, monitoring and regulation of blood pressure, and the like. As a diagnostic assay, the methods of this invention supplement traditional testing methods (e.g., HDL:LDL ratios, etc.) to identify subjects known to be at risk who may prove resistant to conventional therapeutic regimens and alter the prescribed treatment. Thus, for example, where a subject is diagnosed with early stages of atherosclerosis, a positive test using the assays of this invention may indicate additional drug intervention rather than simply dietary/lifestyle changes.

In one embodiment the assays exploit the discovery that the "Group I HDLs" can actually reduce and/or eliminate oxidized phospholipids. Thus, Group I HDLs can be identified by providing a biological sample from said mammal (e.g., serum) where the biological sample comprises a high-density lipoprotein (HDL), contacting the high-density lipoprotein with an oxidized phospholipid and/or oxidized phospholipids(s) combined with a low density lipoprotein (LDL); and measuring a change in the amount of oxidized or non-oxidized phospholipid wherein a reduction in the amount of oxidized phospholipid indicates the mammal has Group I HDLs and, hence, is at lower risk for atherosclerosis. Conversely, where no significant change in oxidized phospholipid is observed, the subject has Group II HDLs and is at increased risk for atherosclerosis.

In another embodiment, the assays of this invention exploit the discovery that Group I HDLs can prevent the oxidization of LDLs and/or phospholipid-containing components of LDLs. These assays preferably involve providing a biological sample from a mammal where the sample comprises a high-density lipoprotein (HDL), contacting the high density lipoprotein with a phospholipid (e.g., isolated phospholipid and/or with a low density lipoprotein), subjecting the phospholipid to oxidizing conditions; and measuring a change in the amount of oxidized or non-oxidized phospholipid. A change in the amount of oxidized or non-oxidized phospholipid indicates that the HDL is a Group II HDL and is not protecting the lipid from oxidation. Thus subject mammal is thus at increased risk for atherosclerosis. Where there is reduced, or no substantial change in oxidized or unoxidized phospholipid, the HDL affords protection against lipid oxidation and the subject is at reduced risk for atherosclerosis and associated pathologies.

The assays of this invention are rapid, simple, inexpensive, and can readily be formatted as a "home test kit".

I. HDL Activity Assays.

As indicated above, in certain preferred embodiments, the assays of this invention can be performed in several formats. In one format, the HDL is assayed for the ability to reduce the level of oxidized phospholipid (e.g., in a low density lipoprotein). In another format, the HDL is assayed for the ability to protect a phospholipid from oxidation by an oxidizing agent.

Both assay formats require provision of a biological sample containing HDL (or components thereof) contacting the HDL (or KDL components) with a lipid (oxidized or not depending on the assay), and detecting the amount of oxidized lipid or lipid that is not oxidized. The assays differ in that the first assay contacts the HDL (or HDL component) of an oxidized lipid (or LDL comprising such lipid), while the second assay contacts the HDL to a lipid that is not oxidized, and contacting the lipid with an oxidizing agent to evaluate the protection from oxidation afforded by the HDL.

A) Providing a Biological Sample Comprising HDL.

In certain preferred embodiments the assays are performed using a biological sample from the organism/subject of interest. While the assays are of great use in humans, they are not so limited. It is believed similar HDL subtypes exist essentially in all mammals and thus the assays of this invention are contemplated for veterinary applications as well. Thus, suitable subjects include, but are not limited to humans, non-human primates, canines, equines, felines, porcines, ungulates, largomorphs, and the like.

A suitable biological sample includes a sample of any biological material (e.g., fluid, cell, tissue, organ, etc.) comprising high density lipoproteins (HDLs) or components thereof. One particularly preferred tissue is liver tissue. In a most preferred embodiment, the biological sample is a blood sample. As used herein a blood sample includes a sample of whole blood or a blood fraction (e.g., serum, plasma, etc.). The sample can be fresh blood or stored blood (e.g., in a blood bank) or blood fractions. The sample can be a blood sample expressly obtained for the assays of this invention or a blood sample obtained for another purpose which can be subsampled for the assays of this invention.

The sample may be pretreated as necessary by dilution in an appropriate buffer solution, heparinized, concentrated if desired, or fractionated by any number of methods including but not limited to ultracentrifugation, fractionation by fast performance liquid chromatography (FPLC), or precipitation of apolipoprotein B containing proteins with dextran sulfate or other methods. Any of a number of standard aqueous buffer solutions, employing one of a variety of buffers, such as phosphate, Tris, or the like, at physiological pH can be used.

In certain embodiments, the sample is treated to remove non-HDL cholesterol. This can be accomplished by any of a number of methods know to those of skill in the art. In one embodiment, this is accomplished by the use of a commercially supplied magnetic bead reagent, e.g., as described in the examples.

B) Contacting the HDL With a Lipid.

HDL from the biological sample is then contacted with a lipid (oxidized or not depending on the assay as described above) or collection of lipids (isolated lipid(s) or presented as an LDL). The HDL can be fully isolated, partially isolated, or the whole (e.g., unfractionated) biological sample can be contacted with the lipid. Methods of partially or completely isolating HDL are known to those of skill in the art (see, e.g., Havel, et al. (1955) *J Clin Invest* 43:1345-1353; Navab et al. (1997) *J Clin Invest* 99:2005-2019; Carroll and Rudel (1983) *J Lipid Res* 24:200-207, McNamara et al. (1994) *Clin Chem* 40:233-239, Grauholt et al. (1986) *Scandinavian J Clin Lab Invest* 46:715-721; Warnick et al. (1982) *Clin Chem* 28:1379-1388; Talameh et al., (1986) *Clin Chimica Acta* 158:33-41).

In a preferred embodiment, the lipid that is contacted comprises one or more lipids (preferably phospholipids) capable of being oxidized. Preferred lipid(s) include, but are not limited to reduced (not oxidized) 1-palmitoyl-2-arachidonoyl-sn-glycero-3-phosphorylcholine, 1-palmitoyl-2-oxovaleroyl-sn-glycero-3-phosphorylcholine (POVPC), 1-palmitoyl-2-glutaroyl-sn-glycero-3-phosphorylcholine (PGPC), 1-palmitoyl-2-epoxyisoprostane-sn-glycero-3-phosphorylcholine (PEIPC), 1-stearoyl-2-arachidonoyl-sn-glycero-3-phosphorylcholine (SAPC), 1-stearoyl-2-oxovaleroyl-sn-glycero-3-phosphorylcholine (SOVPC), 1-stearoyl-2-glutaroyl-sn-glycero-3-phosphorylcholine (SGPC), 1-stearoyl-2-epoxyisoprostane-sn-glycero-3-phosphorylcholine (SEIPC), 1-stearoyl-2-arachidonyl-sn-glycero-3-phosphorylethanolamine (Ox-SAPE), 1-stearoyl-2-oxovaleroyl-sn-glycero-3-phosphorylethanolamine (SOVPE), 1-stearoyl-2-glutaroyl-sn-glycero-3-phosphorylethanolamine (SGPE), and 1-stearoyl-2-epoxyisoprostane-sn-glycero-3-phosphorylethanolamine(SEI PE).

These lipids are illustrative and not intended to be limiting. Other suitable lipids can be readily identified by those of ordinary skill in the art. This is accomplished simply by contacting the lipid(s) in question with an oxidizing agent (e.g., hydrogen peroxide, HPODE, HPETE, HODE, HETE, etc.) and measuring the amount of oxidized lipid produced. Alternatively, the "oxidized lipid/LDL can be assayed for its ability to induce a response characteristic of atherosclerotic plaque formation (e.g., induction of monocyte adhesion and/or chemotaxis, and/or differentiation in a culture of vascular endothelial cells).

The lipid(s) can be presented as "isolated" or "partially isolated" lipid(s) or may be presented/contacted in the form of a low density lipoprotein (LDL). The LDL can be an LDL isolated from an organism or a synthetically assembled/created LDL. Means of isolating or synthesizing lipids (e.g., phospholipids), and/or LDLs are well known to those of skill in the art (see, e.g., Havel, et al. (1955) *J Clin Invest* 43:1345-1353; Navab et al. (1997) *J Clin Invest* 99:2005-2019; Carroll and Rudel (1983) *J Lipid Res* 24:200-207, etc.).

C) Detecting the Level of Oxidized Lipid.

As indicated above, the assays can involve detecting the amount of oxidized lipid, or conversely lipid that is not oxidized. Since, in certain embodiments, the lipid content of the assay is essentially constant, a measurement of oxidized lipid or change in oxidized lipid provides a measure of lipid that is not oxidized or a change in the amount of lipid that is not oxidized and vice versa.

Methods of measuring oxidized lipids are well known to those of skill in the art (see, e.g., Vigo-Pelfrey et al. *Membrane Lipid Oxidation*, Volume I-III. CRC Press). such methods include, but are not limited to mass spectrometry, absorption spectrometry (e.g., using UV absorbance at 234 nm), liquid chromatography, thin layer chromatography, and the use of various "oxidation-state" sensitive reagents (e.g., dichlorofluorescein diacetate (DCFH-DA), etc.), e.g., in various redox reactions.

Previously known methods for measuring oxidized lipids (e.g., lipid peroxides), include the Wheeler method, iron thiocyanate method, thiobarbituric acid method, and others. The Wheeler method (Wheeler (1932) *Oil and Soap*, 9: 89-97) is that in which oxidized lipid is reacted with potassium iodide to isolate iodine, which is then titrated with a sodium thiosulfate standard solution. In the iron thiocyanate method (Stine et al. (1954) *J. Dairy Sci.*,37: 202) oxidized lipid peroxide is mixed with ammonium thiocyanate and ferrous chloride, and the blue color from the resulting iron thiocyanate is calorimetrically determined. In the thiobarbituric acid method (Tappel and Zalkin (1959) *Arch. Biochem. Biophys.*,80: 326) the lipid peroxide is heated under acidic conditions and the resulting malondialdehyde is condensed with thiobarbituric acid to form a red color dye, which is then calorimetrically measured.

In another approach, it has been demonstrated that peroxidase decomposes lipid peroxides and that the resulting reaction system colors intensely with increasing quantities of lipid peroxide, if an adequate hydrogen donor is present in the reaction system (see, e.g., U.S. Pat. No. 4,367,285) Thus, in one embodiment, the assays of this invention may utilize a peroxidase and a hydrogen donor.

Many peroxidases are suitable. In preferred embodiments, the peroxidase employed in the present invention is preferably any of the commercially available horseradish peroxidases.

In certain embodiments, the hydrogen donor employed in the present invention is any of the known oxidizable compounds which, preferably, generate color, fluorescence or luminescence upon oxidation. The conventional coloring, fluorescent, luminescent reagents may be utilized. The known coloring reagents which may be employed include, but are not limited to guaiacol, 4-aminoantipyrine with phenol, 4-aminoantipyrine with N,N-dimethylaniline, 3-methyl-2-benzothiazolinone with dimethylaniline, ortho-dianisidine, and the like. Typically useful fluorescent reagents include, but are not limited to homovanillic acid, p-hydroxyphenylacetic acid, and the like. Suitable luminescent reagents include but are not limited to luminol and the like. All of these reagents are mentioned merely for exemplification, and not for limitation, of the hydrogen donor of the present invention.

The amount of the hydrogen donor employed is preferably at least equimolar, preferably not less than two moles, per mole of lipid peroxide contained in test sample. The amount may be varied depending upon the size of the sample and the content of the lipid peroxide in the sample.

Suitable reaction mediums which can be employed include, but are not limited to dimethylglutarate-sodium hydroxide buffer solution, phosphate buffer solution and, Tris-hydrochloric acid buffer solution is normally from about pH 5 to about pH 9.

A typical (high volume) assay (3 ml) may contain a 50 mM dimethylglutarate-sodium hydroxide buffer solution (pH 6.0) containing 0.03% (W/V) of 4-aminoantipyrine, 0.04% (V/V) of N,N-dimethylaniline and 4.5 units of peroxidase. In a typical measurement, the assay solution is preliminarily warmed to 37° C. and 50 µL of a test sample containing lipid peroxide is added. The mixture is incubated at 37° C. for 15 minutes and, the intensity of the color generated is measured suing a spectrophotometer at a wavelength of, for example, 565 nm. The amount of the lipid peroxide in the sample is calculated from the extinction value.

Such factors as the pH at the time of reaction, the reaction period, the measuring wavelength, etc., may be varied depending upon the reagents employed. Suitable conditions can be selected according to the circumstances.

Another class of assays for oxidized lipids is described in U.S. Pat. No. 4,900,680. In this approach, an oxidized lipid (e.g., a hydroperoxide) is reacted with a salt or hydroxide of a transition metal which produces a cation having a valency of 2, a complex of a transition metal having a valency of 2, a heme, a heme peptide, a heme protein, or a heme enzyme. The resultant active oxygen and oxygen radicals react with a luminescent substance, and light emitted by this reaction is optically measured. Examples of a catalyst acting on a lipid hydroperoxide to produce active oxygen species such as active oxygen or oxygen radicals are: a transition metal salt which produces a cation having a valency of 2 (e.g., ferrous chloride, ferrous sulfate, potassium ferricyanide, each of which produces $Fe^{2+}$; manganous chloride or manganous sulfate, each of which produces $Mn^{2+}$; or cobalt chloride or cobalt sulfate, each of which produces $Co^{2+}$); a hydroxide of the transition metals described above; a complex of a transition metal having a valency of 2 (e.g., $Fe^{II}$-porphyrin complex); a heme protein (e.g., cytochrome C, hemoglobin, or myoglobin); a heme peptide (e.g., a compound obtained by decomposing a heme protein by a protease such as chymotrypsin or trypsin); and a heme enzyme (e.g., horseradish peroxidase or prostaglandin peroxidase).

Preferred catalyst compounds include, but are not limited to, a heme protein, a heme peptide, or a heme enzyme. Most usually, the heme protein such as cytochrome C is used due to easy handling. The concentration of the catalyst compound preferably ranges from about 0.1 µg/ml to about 1,000 µg/ml and usually falls within the range of about 1 µg/ml to about 200 µg/ml. For example, best luminous efficiency can be obtained when the concentration is about 10 µg/ml for cytochrome C, about 120 µg/ml for cytochrome C heme peptide; and about 10 µg/ml for horseradish peroxidase.

The luminescent substance is not limited to a specific one, provided it reacts with active oxygen or an oxygen radical to emit light. Examples of such a compound include, but are not limited to polyhydroxyphenols (e.g., pyrogallol, perprogalline etc.), phthaladine derivatives (e.g., luminol, isoluminol, etc.), indol derivatives (e.g., indoleacetic acid, skatole, tryptophan, etc.); thiazolidine derivatives (e.g., Cypridinacea luciferin, lophine, etc.), an acrydine derivatives (e.g., lucigenine), oxalic acid derivatives (e.g., bistrichlorophenyloxalate); and 1,2-dioxa-4,5-azine derivatives. The concentration of the luminescent substance varies depending on the compound used. The concentration is preferably 0.1 µg/ml or more. When luminol is used, its concentration is most preferably 1 µg/ml.

Measurements are preferably performed in a weak basic solution of a luminescent reagent such as a heme protein and luminol. A preferred pH value ranges from about pH 9 to about pH 10. Many buffers are suitable. On preferred buffer is a borate buffer ($H_3BO_3$—KOH), a carbonate buffer ($Na_2CO_3$—$NaHCO_3$), a glycine buffer ($NH_2CH_2$ COOH—NaOH), or the like. The borate buffer is most preferred.

In order to prevent oxygen dissolved in the luminescent reagent solution from interfering analysis of a very small amount of oxidized lipid, the luminescent reagent solution is desirably purged with an inert gas to remove oxygen to obtain a stable measurement value. Examples of the inert gas are nitrogen gas and argon gas.

The concentration of the oxidized lipid in the sample is calculated based on a calibration curve. The calibration curve can be formed according to standard methods, e.g., by using a material selected from methyl linolate hydroperoxide, arachidonic acid hydroperoxide, phosphatidylcholine hydroperoxide, phosphatidylethanolamine hydroperoxide, and triacylglycerol hydroperoxide.

In preferred embodiments, the assays of this invention utilize fluorescent materials whose fluorescence is altered by oxidation state. Such fluorescent materials are well known to those of skill in the art and include, but are not limited to 2'7'-dichlorodihydrofluorescine diacetate, rhodamine cis-parinaric acid, NBD, cis-parinimic acid cholesteryl esters, diphenylhexatriene proprionic acid, and the like. The use of such indicators is illustrated in the examples.

In certain embodiments, antibodies can be used to specifically detect oxidized phospholipids. Thus, for example U.S. Pat. No. 6,225,070 provides a panel of monoclonal antibodies ("E0 antibodies") that have unique binding specificity for one or more oxidation-specific epitopes on oxidized blood lipoproteins. The E0 antibodies can be used in any of a number of convenient immunoassay formats (e.g., ELISA, sandwich, etc.) to detect oxidized phospholipids in the methods described herein.

It will be appreciated that the foregoing methods of detecting/quantifying oxidized lipids are intended to be illustrative and not limiting. Numerous other methods of assaying oxidized lipids are known to those of skill in the art and are within the purview of this application.

D) Contacting the Lipid With an Oxidizing Agent.

In the "second" assay format described above, a lipid or collection of lipids (isolated or present in an LDL) are contacted with an oxidizing agent and the HDL is assayed for the ability to protect the lipids from oxidization. Essentially any agent capable of oxidizing a phospholipid is suitable for use in this invention. Such agents include, but are not limited to various peroxides, and in particularly preferred embodiments the oxidizing agent is a hydrogen peroxide, 13(s)-HPODE, 15(S)-HPETE, HPODE (hydroperoxyoctadecadienoic acid), HPETE (hydroperoxyeicosatetraenoic acid), HODE, HETE, and the like.

The suitability of other oxidizing agents can be readily determined. This is easily accomplished by contacting an LDL and/or the isolated phospholipid(s) of interest with the oxidizing agent and measuring the amount of oxidized lipid produced. Alternatively, the "oxidized lipid/LDL can be assayed for its ability to induce a response characteristic of atherosclerotic plaque formation (e.g., induction of monocyte adhesion and/or chemotaxis, and/or differentiation in a culture of vascular endothelial cells).

E) Scoring the Assay.

The assays are scored as positive for "Group I" HDL (negative for "Group II" HDL) where the HDL reduces the amount of oxidized lipid or prevents lipid from being oxidized in the assay. Conversely, the assays are scored as negative for "Group I" HDL (positive for "Group II" HDL) where the HDL does not reduce the amount of oxidized lipid or fails to prevent lipid from being oxidized in the assay.

While initial studies indicate that some HDLs offer protection and others do not, it is neither expected nor required that, on a population level, the distribution of responses be bi-modal. To the contrary, it is expected that the degree of protection against lipid oxidation or repair of oxidized lipids by HDL will vary with parameters such as genetics, sex, age, physiological maturity, ethnicity, (gestational stage for females), general health, immunocompetency of the subject, and the like.

To facilitate the use of a commercial embodiment of the assays for this invention, the effects of these (and other) parameters on the protection afforded by HDL can be routinely determined. Thus, for example, HDL protection can be assayed in elderly individuals that are diagnosed by other means as very low risk for atherosclerosis and in elderly individuals determined to have advanced atherosclerosis. This will provide a measure of the activity of "protective HDL" or lack of activity in "non-protective HDL" among the elderly and permit comparisons of HDL activity with the young. The effects of these other parameters can similarly be determined and from such studies population baseline "activity" levels for protective and non-protective HDL can be determined.

It is emphasized that such measurements need not produce an "absolute" scale to be of considerable use. An evaluation of relative risk is of great use. Because an indication of "elevated" risk for atherosclerosis can be addressed with relatively little investment (e.g., increased exercise, dietary changes, increased monitoring, etc.) the downside risk of a false positive (i.e. an indication that the individual is at greater risk of atherosclerosis) is minor. Similarly, with the presence of other diagnostic/risk factors for atherosclerosis (e.g., HDL:LDL ratios, blood pressure monitoring, behavioral and general health factors, etc.) the downside risk of a false negative (i.e. an indication that the individual's HDL offers protection against lipid oxidation) is also relatively slight.

The assay may be scored as positive, negative, or assigned a score on a continuum (e.g., a particular risk level ranging from very low risk to low risk to moderate risk to high risk to very high risk, etc.) by comparison or the assay result to levels determined for the relevant population (e.g., corrected for the various parameters described above) and/or by direct reference to a positive or negative control. Thus, for example, the results of an assay for change in oxidized lipid caused by contacting the lipid(s) with the subject's HDL may be compared to a "control" assay run without the HDL (or with the HDL at lower concentration). In this instance, a decrease in oxidized lipid in the presence of the HDL as compared to the assay in the absence of HDL indicates the HDL offers protection/repair of oxidized lipids (i.e., is positive for "Group I" HDL).

Similarly in an assay where HDL is assayed for the ability to protect lipids from an oxidizing agent, the assay results may be compared with a control assay that is identical but lacking the HDL (or having he HDL present at lower concentration). Where the assay shows more oxidized lipid in the absence or reduced HDL, the assay is scored as positive for Group I HDL.

The assays are scored as positive, as described above, where the difference between the test assay and the control assay is detectable, and more preferably where the difference is statistically significant (e.g., at least at the 85%, preferably at least at the 90%, more preferably at least at the 95%, and most preferably at least at the 98% or 99% confidence level).

II. Assay Formats.

The assays of this invention can be practiced in almost a limitless variety of formats depending on the particular needs at hand. Such formats include, but are not limited to traditional "wet chemistry" (e.g., as might be performed in a research laboratory), high-throughput assays formats (e.g., as might be performed in a pathology or other clinical laboratory), and "test strip" formats, (e.g., as might be performed at home or in a doctor's office).

A) Traditional Wet Chemistry.

The assays of this invention can be performed using traditional "wet chemistry" approaches. Basically this involves performing the assays as they would be performed in a research laboratory. Typically the assays are run in a fluid phase (e.g., in a buffer with appropriate reagents (e.g., lipids, oxidized lipids, oxidizing agent, etc.) added to the reaction mixture as necessary. The oxidized lipid concentrations are assayed using standard procedures and instruments, e.g., as described in the examples.

B) High-throughput Assay Formats.

Where population studies are being performed, and/or in clinical/commercial laboratories where tens, hundreds or even thousands of samples are being processed (sometimes in a single day) it is often preferably to perform the assays using high-throughput formats. High throughput assay modalities are highly instrumented assays that minimize human intervention in sample processing, running of the assay, acquiring assay data, and (often) analyzing results. In preferred embodiments, high throughput systems are designed as continuous "flow-through" systems, and/or as highly parallel systems.

Flow through systems typically provide a continuous fluid path with various reagents/operations localized at different locations along the path. Thus, for example a blood sample may be applied to a sample receiving area where it is mixed with a buffer, the path may then lead to a cell sorter that removes large particulate matter (e.g., cells), the resulting fluid may then flow past various reagents (e.g., where the reagents are added at "input stations" or are simply affixed to the wall of the channel through which the fluid flows. Thus, for example, the sample may be sequentially combined with a lipid (e.g., provided as an LDL), then an oxidation agent, an agent for detecting oxidation, and a detector where a signal (e.g., a colorimetric or fluorescent signal) is read providing a measurement of oxidized lipid.

In highly parallel high throughput systems samples are typically processed in microtiter plate formats (e.g., 96 well plates, 1536 well plates, etc.) with computer-controlled robotics regulating sample processing reagent handling and data acquisition. In such assays, the various reagents may all be provided in solution. Alternatively some or all of the reagents (e.g., oxidized lipids, indicators, oxidizing agents, etc.) may be provided affixed to the walls of the microtiter plates.

High throughput screening systems that can be readily adapted to the assays of this invention are commercially available (see, e.g., Zymark Corp., Hopkinton, Mass.; Air Technical Industries, Mentor, Ohio; Beckman Instruments, Inc. Fullerton, Calif.; Precision Systems, Inc., Natick, Mass., etc.). These systems typically automate entire procedures including all sample and reagent pipetting, liquid dispensing, timed incubations, and final readings of the microplate in detector(s) appropriate for the assay. These configurable systems provide high throughput and rapid start up as well as a high degree of flexibility and customization. The manufacturers of such systems provide detailed protocols the various high throughput. Thus, for example, Zymark Corp. provides technical bulletins describing screening systems for detecting the modulation of gene transcription, ligand binding, and the like.

C) "Test Strip" Assay Formats.

In certain preferred embodiments, the assays of this invention are provided in "test well" or "test strip" formats. In "test well" or "test strip" formats, the biological sample is typically placed in the well or applied to a receiving zone on the strip and then a fluorescent or calorimetric indicator appears which, in this case, provides a measure of the protection or repair afforded by the subject's HDL or components thereof.

Many patents have been issued which describe the various physical arrangements for blood testing. These include systems which involve lateral or horizontal movement of the blood, as well as plasma testing. For example, U.S. Pat. Nos. 4,876,067, 4,861,712, 4,839,297, and 4,786,603 describe test carriers and methods for analytical determination of components of bodily fluids, including separating plasma from blood using glass fibers and the like. These patents, all teach systems which require some type of rotation of test pads or a portion of the test pads during use. U.S. Pat. No. 4,816,224 describes a device for separating plasma or serum from whole blood and analyzing the serum using a glass fiber layer having specific dimensions and absorption to separate out the plasma from the whole blood for subsequent reaction. Similarly, U.S. Pat. No. 4,857,453 describes a device for performing an assay using capillary action and a test strip containing sealed liquid reagents including visible indicators. U.S. Pat. No. 4,906,439 describes a diagnostic device for efficiently and accurately analyzing a sample of bodily fluid using fluid delivery in a lateral movement via flow through channels or grooves.

In addition to the above patents which are representative of the prior art showing various physical types of systems for blood testing and the like, recent patents have issued which are directed to the particular chemistry for the determination of HDL cholesterol. Thus, U.S. Pat. Nos. 4,851,335 and 4,892,815 also to Kerscher et al, describe specific types of processes and reagents for HDL cholesterol determination.

U.S. Pat. No. 5,135,716 describes a device for determining HDL cholesterol by obtaining plasma from whole blood and determining the HDL cholesterol esterol level from the plasma.

In certain embodiments this invention contemplates devices wherein the sample processing, including plasma separation, HDL metering (if desired), contact with a lipid (oxidized or not oxidized), optional contact with an oxidizing agent, and detection of oxidized lipids are built into a strip such that user manipulations are minimized and HDL protective activity can be measured in one to two minutes directly from whole blood and/or serum. In a preferred embodiment, the method measures the end-point of the reaction and therefore precise time and temperature controls are not necessary.

In certain preferred embodiments the device is similar to that described in the U.S. Pat. No. 5,135,716. Thus, for example, in one embodiment (see, e.g., FIG. 1), the device includes an inert or active substrate support 1. A receiving area/receiving reservoir 11 and/or a filtering membrane, can optionally be present. Disposed in the test device are reagents for the assay typically an oxidized lipid or a lipid that is not oxidized and an oxidizing agent. The lipid and/or the and an optional carrier/detection membrane. The test membrane 6 has reactants which will react with oxidized lipid and indicate quantify oxidized lipid, lipid that is not oxidized, or a ratio of oxidized lipid to lipid that is not oxidized.

In use, blood is added to the blood application area 11 of physical transport medium 3. It travels along the channels 2 and physical transport medium 3 (e.g., a sheet which is a woven mesh of monofilament polyester with 17 micron mesh opening (Tetko, Briarcliff, N.Y.) and having a thickness of about 75 microns). Woven fabric, non-woven fabric, gauze and monofilament yarn are among the many choices for the transport membrane sheet shown as physical transport medium 3. Plasma separation as well as precipitation may be handled by a microporous plasma separation membrane 4, in this case, 5 micron nitrocellulose (Schleicher and Schuell, Keene, N.H.).

An optional filtering membrane 5 filters off the LDL and VLDL precipitates and prevents them from reaching the test membrane 6. When present, in one embodiment, filtering membrane 5 is a 0.4 micron hydrophilic polycarbonate membrane (Poretics Corp., Livermore, Calif.) used without treatment or 0.2 micron nylon (Micron Separations, Inc., Westboro, Mass.) or 0.8 micron polysulfone (Gelman Sciences, Ann Arbor, Mich.). The latter two were saturated with 5% or 10% aqueous solution of polyethylene glycol (molecular weight 1000 daltons) and dried. Polyethylene glycol (PEG) is optionally used as a wetting agent.

In certain preferred embodiments, test membrane 6, as mentioned, contains enzymes and/or and chromogens and/or fluorescenrs assaying oxidized lipid so that HDL-containing sample reaching it (now devoid of LDL and VLDL components) reacts with the reagents (e.g., oxidized lipid, lipid that is not oxidized and oxidizing agent(s)) in the test membrane 6, producing a colored reaction, the intensity of color being proportional to oxidized lipid and/or to non-oxidized (reduced) lipid) concentration.

In one preferred embodiment the test membrane 6 is a 0.45 micron nylon membrane (Micron Separations, Inc, Westboro, Mass.). Top sheet 7 with orifice 12 and transparent area 29 is adhered over the tops of the other components as shown by arrows 8 and 9. Transparent area 29 is comprised of an aperture covered with a transparent membrane that may or may not be oxygen permeable.

A drop of blood can be applied to the blood application area 11 of physical transport medium 3 through orifice 12 and the calorimetric reaction may be viewed through transparent area 29. Alternatively, one or more of the layers may be strong enough to support the device in the absence of an inert substrate support.

One will appreciate that such a laminate device may be designed as a test strip to which a sample is applied, as a "dipstick" for immersion into a sample, or as a component of a sample receiving receptacle (e.g., a well in a microtiter plate). It will also be appreciated that this embodiment is intended to be illustrative and not limiting. Following the teaching provided herein and the ample body of literature pertaining to the design of "test strips" such assays for HDL activity according to the methods of this invention can readily be assembled by those of skill in the art.

V. Kits.

In another embodiment, this invention provides kits for practicing one or more of the assays described herein. Assay kits preferably comprise one or more containers containing one or more oxidized lipids (isolated or provided in an LDL), and/or a reduced (not oxidized) lipid and an oxidizing agent (e.g., hydrogen peroxide, 13(S)-HPODE, 15(S)-HPETE, HPODE, HODE, HETE, HPETE, etc.). The kit preferably includes one or more reagents for the detection of oxidized lipids (e.g., 2',7'-dichlorodihydrofluorescine diacetate, rhodamine, cis-parinaric acid, NBD, cis-parinaric acid cholesteryl ester, diphenylhexatriene propionic acid, and other fluorescent materials). The kits may optionally include any one or more of the devices and/or reagents for practice of the asssays as described herein. Such devices and/or reagents include, but are not limted to microtiter plates, buffers, filters for quantification of fluorescence, etc.

In addition, the kits optionally include labeling and/or instructional materials providing directions (i.e., protocols) for the practice of the assay methods. Preferred instructional materials describe screening HDL (or components thereof) for the ability to protect lipids from okidization or to reduce oxidized lipids. The instructional materials optionally include a description of the use of such assays for evaluating risk for atherosclerosis.

While the instructional materials typically comprise written or printed materials they are not limited to such. Any medium capable of storing such instructions and communicating them to an end user is contemplated by this invention. Such media include, but are not limited to electronic storage media (e.g., magnetic discs, tapes, cartridges, chips), optical media (e.g., CD ROM), and the like. Such media may include addresses to internet sites that provide such instructional materials.

EXAMPLES

The following examples are offered to illustrate, but not to limit the claimed invention.

Example 1

Normal HDL Inhibits Three Steus in the Formation of Mildly Oxidized LDL-Step 1

Apo A-I and an apo A-I peptide mimetic removed "seeding molecules" from human LDL and rendered the LDL resistant to oxidation by human artery wall cells. The apo A-I-associated "seeding molecules" included 13-hydroperoxyoctadecadienoic acid [13-HPODE] and 15-hydroperoxyeicosatetraenoic acid [15-HPETE]. LDL from mice genetically susceptible to fatty streak lesion formation was highly susceptible to oxidation by artery wall cells and was rendered resistant to oxidation after incubation with apo A-I in vitro. Injection of apo A-I (but not apo A-II) into mice rendered their LDL resistant to oxidation within 3 hours. Infusion of apo A-I into humans rendered their LDL resistant to oxidation within 6 hours. HDL and its associated enzyme paraoxonase (PON) also rendered LDL resistant to oxidation. We conclude that: (1) oxidation of LDL by artery wall cells requires "seeding molecules" that include 13-HPODE and 15-HPETE; (2) LDL from mice genetically susceptible to atherogenesis is more readily oxidized by artery wall cells; (3) Normal HDL and its components can remove or inactivate lipids in freshly isolated LDL that are required for oxidation by human artery wall cells.

Introduction.

HDL and its major apolipoprotein, apo A-I, are known to remove cholesterol and phospholipids from cells (Oram and Yokoyama (1996 *J. Lipid Res*. 37: 2473-2491; Forte et al. (1995). *J. Lipid Res*. 36: 148-157; Bruce et al. (1998) *Ann. Rev. Nutr*. 18: 297-330; Phillips et al. (1998) *Atheroscler*. 137 Suppl: S13-S-17). Stocker and colleagues (Christison et al. (1995) *J. Lipid Res*. 36: 2017-2026) and Fluiter et al. (1999) *J. Biol. Chem*. 274: 8893-8899, have reported that cholesteryl ester hydroperoxides can be transferred from LDL to HDL, in part, mediated by cholesteryl ester transfer protein. Fluiter and colleagues (Id.) also demonstrated that there was a selective uptake of oxidized cholesteryl esters from HDL by rat liver parenchymal cells. Stocker and colleagues (Garner et al. (1998) *J. Biol. Chem*. 273: 6080-6087) reported that both apo A-I and apo A-II can reduce cholesteryl ester hydroperoxides via a mechanism that involves oxidation of specific methionine residues (Garner et al. (1998) *J. Biol. Chem*. 273: 6088-6095). However, a direct role for apo A-I in removing oxidized lipids from lipoproteins and cells has not previously been reported.

Sevanian and colleagues noted that a subpopulation of freshly isolated LDL that they have described as LDL contains lipid hydroperoxides (Sevanian et al. (1997) *J. Lipid Res*. 38: 419-428). Parthasarathy (Parthasarathy (1994) *Modified Lipoproteins in the Pathogenesis of Atherosclerosis*. Austin, Tex.; R. G. Landes Co. pp. 91-119; Parthasarathy (1994) *Free Radicals in the Environment, Medicine and Toxicology*. edited by H. Nohl, H. Esterbauer, and C. Rice Evans. Richelieu Press, London. pp. 163-179), Witztum and Steinberg (1991) *J. Clin. Invest*. 88: 1785-1792; Witztum (1994) *Lancet* 344: 793-795; Chisolm (1991) *Clin. Cardiol*. 14: 125-130; Thomas and Jackson (1991) *J. Pharmacol. Exp. Therap*. 256: 1182-1188; Shwaery et al. (1999) *Meth. Enz*. 300: 17-23; Polidori et al. (1998) *Free Rad. Biol. Med*. 25: 561-567; Thomas et al. (1994) *Arch. Biochem. Biophys*. 315: 244-254, have studied LDL oxidation in vitro by metal ions and have hypothesized that LDL must be "seeded" with reactive oxygen species before it can be oxidized. Jackson and Parthasarathy suggested a role for lipoxygenases (LO) in the "seeding" of LDL (Parthasarathy (1994) *Free Radicals in the Environment, Medicine and Toxicology*. edited by H. Nohl, H. Esterbauer, and C. Rice Evans. Richelieu Press, London. pp. 163-179; Thomas and Jackson (1991) *J. Pharmacol. Exp. Therap*. 256: 1182-1188). They also hypothesized the possibility that hydrogen peroxide or its lipoperoxide equivalent (Parthasarathy (1994) *Free Radicals in the Environment, Medicine and Toxicology*. edited by H. Nohl, H. Esterbauer, and C. Rice Evans. Richelieu Press, London. pp. 163-179; Thomas and Jackson (1991) *J. Pharmacol. Exp. Therap*. 256: 1182-1188) may play an important role in "seeding" LDL. We previously reported that de-fatted albumin was capable of removing biologically active lipids from mildly oxidized LDL (Watson et al. (1995) *J. Clin. Invest*. 95: 774-782). Based on the known lipid binding properties of apo A-I (1-4), we reasoned that apo A-I was likely to be more effective than de-fatted albumin in binding and removing lipids. We, therefore, used apo A-I and apo A-I mimetic peptides to treat LDL. We hypothesized that if apo A-I could bind oxidized lipids and if the "seeding molecules" were oxidized lipids, then incubating apo A-I and LDL followed by separation of the two, might result in the transfer of the "seeding molecules" from LDL to apo A-I from which they could be extracted and identified. We found that both the neutral lipid and fatty acid fractions of the lipids extracted from apo A-I after incubation with LDL contained "seeding molecules". The neutral lipid fraction is the fraction where cholesteryl ester hydroperoxides would be found. Since there is evidence that the lipoxygenase pathway can act to form cholesteryl ester hydroperoxides largely as a result of a non-enzymatic process mediated by the products of fatty acid oxidation and alpha tocopherol (Neuzil et al. (1998) *Biochem*. 37: 9203-9210; Upston et al. (1997) *J. Biol. Chem*. 272: 30067-30074; Upston et al. (1999) *FASEB J*. 13: 977-994), we concentrated our efforts on the fatty acid fraction of the lipids extracted from apo A-I after incubation with freshly isolated LDL. We present evidence in this example that the "seeding molecules" present in freshly isolated LDL are derived, in part, from the cellular metabolism of linoleic acid (13-hydroperoxyoctadecadienoic acid [13-HPODE]) and arachidonic acid (15-hydroperoxyeicosatetraenoic acid [15-HPETE ]) as originally predicted by Parthasarathy (10,11) and in accord with the recent findings of Cyrus et al. that disruption of the 12/15-lipoxygenase gene diminished atherosclerosis in apo E-deficient mice (Cyrus et al. (1999) *J. Clin. Invest*. 103: 1597-1604; Steinberg (1999) *J. Clin. Invest*. 103: 1487-1488).

The experiments presented in this example also indicate that the "seeding molecules" in freshly isolated LDL can be removed and/or inactivated by normal HDL and its components (i.e. apo A-I, and paraoxonase). The experiments detailed in this example and in example 2 have led us to propose that the biologically active lipids (Watson et al. (1997) *J. Biol. Chem*. 272: 13597-13607; Watson et al. (1999) *J. Biol. Chem*. 274: 24787-24798) in mildly oxidized LDL are formed in a series of three steps. The first step is the seeding of LDL with products of the metabolism of linoleic and arachidonic acid as well as with cholesteryl hydroperoxides. The second step is trapping of LDL in the subendothelial space and the accumulation of additional reactive oxygen species derived from nearby artery wall cells. We propose that the third step is the non-enzymatic oxidation of LDL phospholipids that occurs when a critical threshold of reactive oxygen species is reached resulting in the formation of specific oxidized lipids that induce monocyte binding, chemotaxis, and differentiation into macrophages. The experiments in this example focus on the first of these three steps and example 2 presents data on the second and third steps.

Materials & Methods.

Materials.

Tissue culture materials and other reagents were obtained from sources previously described (Navab, et al. (1991) *J. Clin. Invest*. 88: 2039-2046; Navab et al. (1993). *J. Clin. Invest*. 91: 1225-1230; Navab et al. (1997) *J Clin Invest*, 99: 2005-2019). Acetonitrile, chloroform, methanol, ethyl acetate, acetic anyhydride, triethylamine, tert-butanol, polypropylene glycol, ammonium formate, formic acid and water (all Optima grade) were obtained from Fisher Scientific, Pittsburgh, Pa. Authentic L-α-1-palmitoyl-2-arachidonoyl-sn-glycero-3-phosphocholine (PAPC), and linoleic acid were obtained from Avanti Polar Lipids, Inc. (Alabaster, Ala.). The oxidized phospholipids derived from PAPC including Ox-PAPC, and the oxidized phospholipids 1-palmitoyl-2-(5)oxovaleryl-sn-glycero-3-phosphocholine (POVPC, m/z 594), 1-palmitoyl-2-glutaryl-sn-glycero-3-phosphocholine (PGPC, nz/z 610), and 1-palmitoyl-2-(5,6-epoxyisoprostane $E_2$)-sn-glycero-3-phosphocholine (PEIPC, m/z 828) were prepared and isolated as previously described (25,26). 13(S)-HPODE and 15(S)-IPETE were obtained from Biomol (Plymouth Meeting, Pa.). Human apo A-I and apo A-II and soybean lipoxygenase were obtained from Sigma Chemical Co. (St. Louis, Mo.) and were used for in vitro studies and for injection into mice.

SDS-PAGE analyses demonstrated an approximately 90% purity for apo A-I and apo A-II preparations. Apo A-I peptide mimetics were synthesized as previously described (30-32). Human apo A-I/Phosphatidylcholine discs for infusion into humans were prepared as previously described by ZLB Central Laboratory (Bern, Switzerland) (33-35). Purified paraoxonase was a generous gift from Professor Bert La Du of the University of Michigan. In addition two mutant recombinant paraoxonase preparations, that were unable to hydrolyze paraoxon (Sorenson et al. (1995) *Proc. Natl. Acad. Sci*. USA 92: 7187-7191) were utilized.

Lipoproteins.

Low density lipoprotein (LDL, d=1.019 to 1.063 g/ml) and high density lipoprotein (HDL, d=1.063 to 1.21 g/ml) were isolated based on the protocol described by Havel and colleagues (Havel et al. (1955) *J. Clin. Invest*. 43: 1345-1353) from the blood of fasting normal volunteers after obtaining written consent under a protocol approved by the human research subject protection committee of the University of California, Los Angeles. Lipoprotein deficient serum was prepared by removing the pellet following HDL isolation, dialysis and readjustment of the protein concentration to 7.5 g/100 ml. In some experiments butylated hydroxytoluene (BHT) 20 mM in ethanol was added to freshly isolated plasma to a concentration of 20 μM and the lipoproteins were separated by FPLC using methods previously described (Navab et al. (1997) *J Clin Invest*, 99: 2005-2019). The LDL, HDL and LPDS had endotoxin levels below 20 pg/ml which is well below the threshold needed for induction of monocyte adhesion or chemotactic activity. The concentration of lipoproteins reported in this study are based on protein content.

Cocultures.

Human aortic endothelial cells (HAEC), and smooth muscle cells (HASMC) were isolated as previously described (Navab, et al. (1991) *J. Clin. Invest*. 88: 2039-2046). The wells of the microtiter plates were treated with 0.1% gelatin at 37° C. overnight. HASMC were added at a confluent density of $1 \times 10^5$ cells/cm$^2$. Cells were cultured for 2 d at which time they had covered the entire surface of the well and had produced a substantial amount of extracellular matrix. HAEC were subsequently added at $2 \times 10^5$ cells/cm$^2$ and were allowed to grow forming a complete monolayer of confluent HAEC in 2 d. In all experiments, HAEC and autologous HASMC (from the same donor) were used at passage levels of four to six.

Monocyte Isolation.

Monocytes were isolated using a modification of the Recalde method as previously described (Fogelman et al. (1988) *J. Lipid Res*. 29: 1243-1247) from the blood of normal volunteers after obtaining written consent under a protocol approved by the human research subject protection committee of the University of California, Los Angeles.

Monocyte Chemotaxis Assay.

In general, the cocultures were treated with native LDL (250 μg/ml) in the absence or presence of HDL for 8 h. The supernatants were collected and used for determination of lipid hydroperoxide levels. The cocultures were subsequently washed and fresh culture medium 199 (M199) without any additions was added and incubated for an additional 8 hrs. This allowed the collection of monocyte chemotactic activity released by the cells as a result of stimulation by the oxidized LDL. At the end of incubation, the supernatants were collected from cocultures, diluted 40-fold, and assayed for monocyte chemotactic activity. Briefly, the supernatant was added to a standard Neuroprobe chamber (NeuroProbe, Cabin John, Md.), with monocytes added to the top. The chamber was incubated for 60 min at 37° C. After the incubation, the chamber was disassembled and the nonmigrated monocytes were wiped off. The membrane was then air dried and fixed with 1% glutaraldehyde and stained with 0.1% Crystal Violet dye. The number of migrated monocytes was determined microscopically and expressed as the mean±SD of 12 standardized high power fields counted in quadruple wells.

Monocyte Adhesion Assay.

In brief, HAEC monolayers, in 48-well tissue culture plates were incubated with the desired LDL or phospholipid for 4 hrs at 37° C. as described (Watson et al. (1995) *J. Clin. Invest.* 96: 2882-2891). After washing, a suspension of human peripheral blood monocytes was added and incubated for 10 min. The loosely adherent monocytes were then washed away, the monolayers were fixed and the number of adherent monocytes counted in 9 high power microscopic fields.

Effect of 13(S)-HPODE on LDL Oxidation.

Freshly isolated LDL (250 μg) was incubated with pure 13(S)-HPODE (1.0 μg) in 10% LPDS in M 199 for 4 hrs at 37° C. with gentle mixing. LDL was re-isolated by centrifugation and was incubated with monolayers of human aortic endothelial cells. Supernatants were removed at time points ranging from zero to 5 hours and were assayed for lipid hydroperoxide content. The endothelial monolayer was washed after each time point and a monocyte suspension was added, incubated, washed, and the number of adherent monocytes determined.

Treatment of LDL With Soybean Lipoxygenase.

Freshly isolated LDL (250 μg) was incubated with 10 units of pure soybean lipoxygenase bound to sepharose beads for 4 hrs at 37° C. with gentle mixing. LDL was re-isolated by centrifugation and incubated with monolayers of HAEC. Supernatants were removed at time points ranging from zero to 4 hours and were assayed for lipid hydroperoxide content. The endothelial monolayer was washed after each time point and monocyte adhesion determined.

Mice.

C57BL/6J and C3H/HeJ mice were purchased from Jackson Laboratories (Bar Harbor, Me.). All animals were female (4-6 months of age at the time of the experiments). The mice were maintained on a chow diet, Purina Chow (Ralston-Purina Co., St. Louis, Mo.) containing 4% fat. LDL was isolated from groups of the lesion susceptible C57BL/6 and from the lesion resistant C3H/HeJ mice from blood obtained from the retroorbital sinus using heparin as an anticoagulant (2.5 U/ml blood) and under mild isoflurane anesthesia, adhering to the regulations set forth by the University of California Animal Research Committee.

Infusion of apo A-I Into Humans.

After obtaining written informed consent and with IRB approval from St Bartholomew's and the Royal London School of Medicine and Dentistry, apo A-I/phosphotidylcholine discs were infused at a dose of 40 mg apo A-I /kg of body weight over four hours using the materials and protocol described by Nanjee et al (Nanjee et al. (1999) *Arterioscler. Thromb. Vascul. Biol.* 19: 979-989; Nanjee et al. (1996) *Arteroscler. Thromb. Vascul. Biol.* 16: 1203-1214) into six healthy male subjects. The lipid levels for these six volunters, subjects 1, 2, 3, 4, 5, and 6 respectively, were: Total Cholesterol: 149, 160, 164, 209, 153, 163; Triglycerides: 176, 169, 95, 150, 121, 153; LDL-cholesterol: 69, 73, 88, 117, 73, 82; and HDL-cholesterol: 45, 54, 56, 62, 59, 47 mg/dl. Plasma was prepared 2 hrs before and 6 hrs following the infusion, was cryopreserved as described (Havel et al. (1955) *J. Clin. Invest.* 43: 1345-1353) and LDL was isolated by FPLC in the authors' lab in Los Angeles before the experiments. LDL islated from plasma according to this protocol functions in a manner that is indistinguishable from freshly isolated LDL in vitro and in vivo (Rumsey et al. (1994) *J. Lipid Res.* 35: 1592-1598).

Fast Performance Liquid Chromatography (FPLC).

Figure 2:
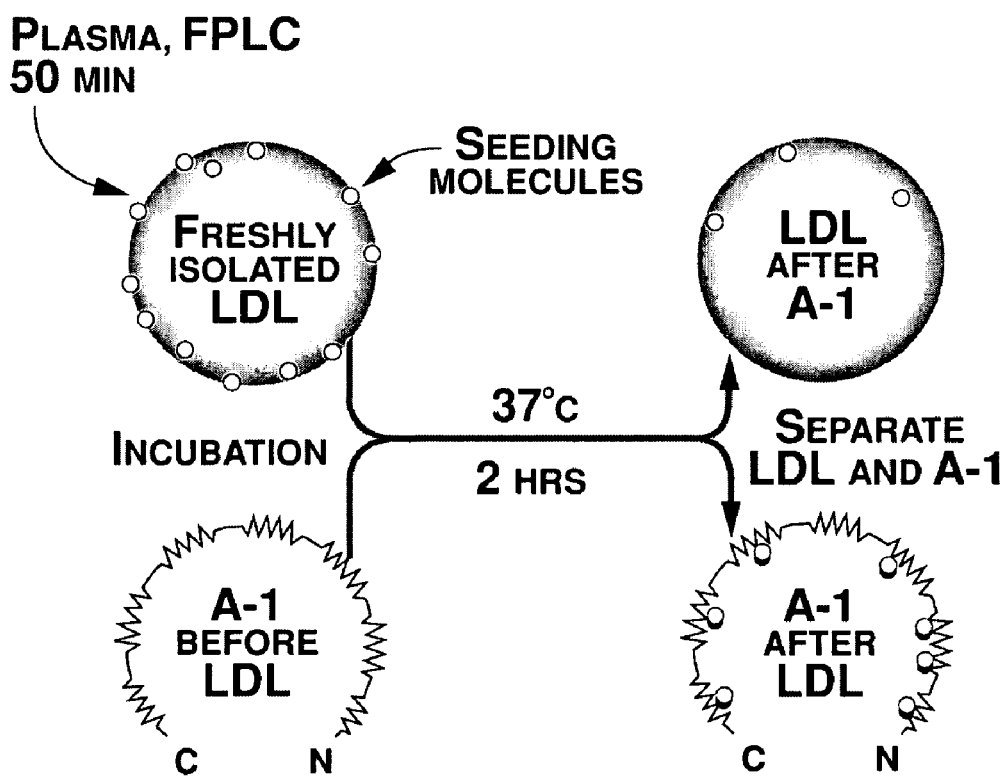
FIG. 2 illustrates the removal of seeding molecules from LDL by apo A-I. Butylated hydroxy toluene (BHT) was added to freshly isolated plasma to a concentration of 20 μM and was fractionated by gel filtration chromatography using an FPLC system with two Superose 6 columns connected in series and eluting with normal saline. The fractions containing LDL were pooled. Purified apo A-I (100 μg/ml) was added to the LDL (1 mg/ml) and incubated for 2 hrs at 37° C. with gentle mixing in normal saline. The LDL and apo A-I were then re-isolated by FPLC or by centrifugation. Re-isolated LDL is designated "LDL after A-I" and the re-isolated apo A-I is designated "A-I after LDL".

Fast performance liquid chromatography (FPLC) for the rapid and mild isolation of LDL and for re-isolation of LDL and apo A-I after incubation as shown in FIG. 2 was performed as previously reported (Navab et al. (1997) *J Clin Invest*, 99: 2005-2019).

Solid Phase Extraction Chromatography.

Solid phase extraction chromatography was preformed as previously described (Kaluzny et al. (1985) *J. Lipid Res.* 26: 135-140). In brief, the lipid extract from no more than 2.0 mg LDL protein was resuspended in 250 μl of chloroform. Solid phase extraction amino columns (Fisher) were conditioned by adding 3.0 ml of methanol followed by 6.0 ml of hexane using a Vac-Elut manifold (Analytichem International, Harbor City, Calif.). The lipids were added to the column and neutral lipids (cholesterol, cholesteryl esters, cholesteryl ester hydroperoxides, triglycerides, diglycerides, and monoglycerides) were eluted with 3.0 ml of chloroform/isopropanol (2:1, v/v). Free fatty acids were eluted with 3.0 ml of 3% acetic acid in diethyl ether, and phospholipids were eluted with 3 ml of methanol. The solvents were evaporated, the lipids were resuspended in chloroform/methanol (2:1, v/v with 0.01% BHT, covered with argon and stored at −80° C. In these analyses the recovery of the C17:0 added as an internal standard was 92±3%.

Reverse Phase High Performance Liquid Chromatography.

High performance reverse phase liquid chromatography (RP-HPLC) was conducted according to the methods of Ames and colleagues (Yamamoto and Ames (1987) *Free Rad. Biol. Med.* 3: 359-361), Kambayashi and colleagues (Kambayashi et al. (1997) *J. Biochem.* 121: 425-431), and Alex Sevanian (personal communication). In brief, the analyses were performed by injecting isolated lipids resuspended in mobile solvent onto the column and eluting with a flow rate of 1.0 ml/min. Detection of fatty acid oxidation products was performed by UV absorbance with a diode array detector (Beckman Instruments) scanning from 200 to 350 nm or with an evaporative light scattering detector (SEDEX 55, France). Hypersil MOS-1 C8 (Alltech) or Supelcosil LC-18-DB (Supelco) columns were used for the separation of fatty acid oxidation products, and a Alltima C18 column (Alltech) was used for the separation of cholesteryl ester oxidation products. A solvent system composed of methanol/triethylamine (99.99/0.01, v/v) was utilized for eluting 13-HPODE, one consisting of a gradient of acetonitrile/water/acetic acid (60/40/0.1, v/v/v) to acetonitrile/water/acetic acid (98/2/0.1, v/v/v) was used for eluting 15-HPETE, and one consisting of acetonitrile/2-propanol/water (44/54/2, v/v/v) for eluting cholesteryl linoleate hydroperoxide.

Electrospray Ionization Mass Spectrometry (ESI-MS).

Electrospray ionization mass spectrometry (ESI-MS) in the positive or negative ion mode was performed according to the protocol and conditions previously described (Watson et al. (1997) *J. Biol. Chem.* 272: 13597-13607).

Other Methods.

Protein content of lipoproteins was determined by a modification (Lehman et al. (1995) *In Vitro Cell. Develop. .Biol. Animal.* 31: 806-810) of the Lowry assay (Lowry et al. (1951) *J. Biol. Chem.* 193: 265-275). The levels of monocyte chemotactic protein 1 were determined using an ELISA as described previously (Navab, et al. (1991) *J. Clin. Invest.* 88: 2039-2046). Lipid hydroperoxide levels were measured using the assay reported by Auerbach et al. (1992) *Anal. Biochem.* 201: 375-380. In some experiments where indicated the lipids in culture supernatant containing LDL that was oxidized by the artery wall cell cocultures was extracted by chloroform-methanol and hydroperoxides determined by the Auerbach method. Paraoxonase (PON) activity was measured as previously described (Gan et al. (1991) *Drug Metab. Dispos.* 19: 100-106). Statistical significance was determined by model 1 ANOVA. The analyses were carried out first using ANOVA in an EXCEL application to determine if differences existed among the group means, followed by a paired Student's t-test to identify the significantly different means, when appropriate. Significance is defined as p<0.05.

Results

Apo A-I and An Apo A-I Peptide Mimetic Remove "Seeding Molecules" from Freshly Isolated Human LDL and Render the LDL Resistant to Oxidation by Human Artery Wall Cells Our human artery wall coculture system has been extensively characterized (Navab, et al. (1991) *J. Clin. Invest.* 88: 2039-2046; Navab et al. (1993). *J. Clin. Invest.* 91: 1225-1230; Navab et al. (1997) *J Clin Invest*, 99: 2005-2019; Shih et al. (1996) *J. Clin. Invest.* 97: 1630-1639; Ishikawa et al. (1997) *J. Clin. Invest.* 100: 1209-1216; Castellani et al. (1997) *J. Clin. Invest.* 100: 464-474; Shih et al. (1998) *Nature* 394: 284-287). When LDL is added to this coculture it is trapped in the subendothelial space and is oxidized by the artery wall cells. As a result, three biologically active oxidized phospholipids are produced—POVPC, PGPC, PEIPC with characteristic m/z ratios of 594, 610, and 828, respectively (Watson et al. (1997) *J. Biol. Chem.* 272: 13597-13607; Watson et al. (1999) *J. Biol. Chem.* 274: 24787-24798). These three oxidized phospholipids account for the ability of mildly oxidized LDL to induce endothelial cells to bind monocytes, secrete the potent monocyte chemoattractant MCP-1, and the differentiation factor M-CSF (Navab, et al. (1991) *J. Clin. Invest.* 88: 2039-2046; Berliner et al. (1990) *J. Clin Invest.* 85: 1260-1266; Rajavashisth et al. (1990) *Nature* 344: 254-257). Conditioned medium from cocultures exposed to LDL was found to contain MCP-1 (Navab, et al. (1991) *J. Clin. Invest.* 88: 2039-2046). When human monocytes were added to the ILDL-treated cocultures, the monocytes bound to the endothelial cells and emigrated into the subendothelial space (Id.). Addition to the cocultures of neutralizing antibody to MCP-1 completely abolished LDL-induced monocyte chemotaxis (Id.). Thus, coculture monocyte chemotaxis is a highly sensitive bioassay for the formation of the biologically active oxidized phospholipids and the subsequent induction of MCP-1 (Navab, et al. (1991) *J. Clin. Invest.* 88: 2039-2046; Navab et al. (1993). *J. Clin. Invest.* 91: 1225-1230; Navab et al. (1997) *J Clin Invest*, 99: 2005-2019; Ishikawa et al. (1997) *J. Clin. Invest.* 100: 1209-1216; Berliner et al. (1990) *J. Clin Invest.* 85: 1260-1266).

Apo A-I is the major protein component of normal HDL. Because of its known ability to bind cholesterol and phospholipids (Oram and Yokoyama (1996 *J. Lipid Res.* 37: 2473-2491; Forte et al. (1995). *J. Lipid Res.* 36: 148-157; Bruceet al. (1998) *Ann. Rev. Nutr.* 18: 297-330; Phillips et al. (1998) *Atheroscler.* 137 Suppl: S13-S-17) we hypothesized that apo A-I might also bind the "seeding molecules" in LDL. To test this hypothesis we utilized the protocol shown in FIG. 1. Butylated hydroxytoluene (BHT) was added to freshly drawn plasma and LDL was separated by FPLC and incubated for 2 hours with apo A-I at 37° C. The LDL and apo A-I were then rapidly separated and studied. We refer to the LDL and apo A-I after separation as "LDL after A-I" and "A-I-after LDL", respectively.

Figure 3:
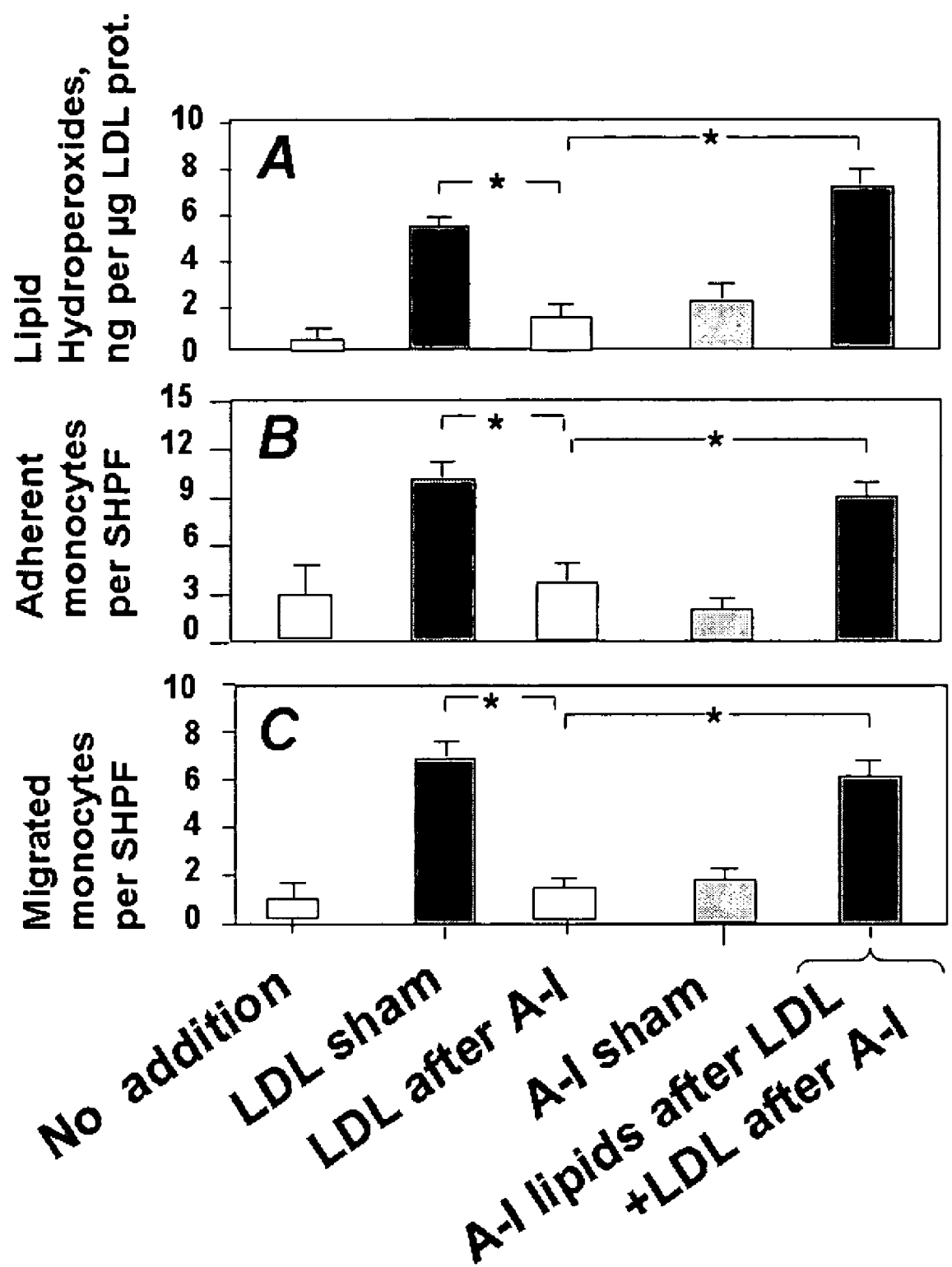
FIG. 3, panels A, B, and C, illustrate the resistance of LDL to oxidation following incubation with apo A-I. LDL was rapidly isolated by FPLC from seven normal human donors and 1 mg/ml LDL incubated with 100 μg/ml apo A-I followed by re-isolation of the LDL and apo A-I as described in FIG. 2. Cocultures of artery wall cells were incubated with sham-treated LDL (LDL sham) or with IDL that was incubated with apo A-I and was re-isolated (LDL after A-I), or with sham-treated apo A-I (A-I sham). To other coculture wells was added reconstituted LDL that was prepared by incubating "LDL after A-I" plus the lipids extracted from "A-I after LDL" (A-I lipids after LDL+LDL after A-I). The cocultures were incubated for 8 hrs at 37° C. in the presence of 10% LPDS. The supernatants were collected and analyzed for lipid hydroperoxide levels. Monocyte adhesion was determined on one set of the cocultures and the others were washed and incubated with culture medium without serum or LPDS for 16 hrs. This conditioned medium was collected and analyzed for monocyte chemotactic activity. Panel A demonstrates the lipid hydroperoxide levels of supernatants. Panel B demonstrates monocyte adherence and Panel C contains the values for monocyte chemotactic activity. The figure is a representative of seven separate experiments using LDL from 7 different normal donors and cocultures and monocytes from different donors. The values are mean±SD of quadruplicate cocultures. The asterisks indicate p<0.0004.
Figure 4:
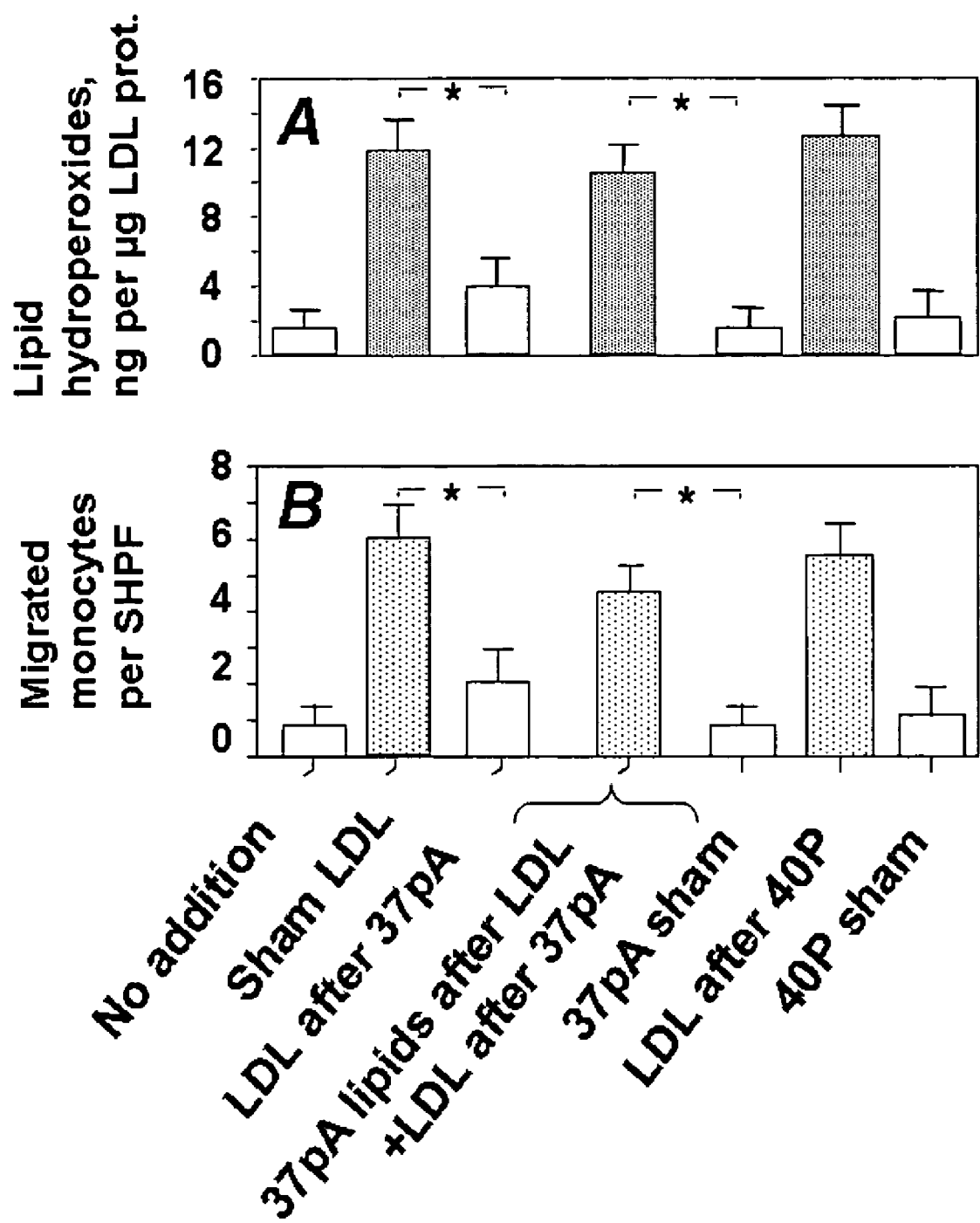
FIG. 4, panels A and B, illustrate the effect of pretreatment of LDL with apo A-I peptide mimetics on LDL oxidation and chemotactic activity. Freshly isolated LDL was incubated at 250 μg/ml with buffer (Sham LDL), with the apo A-I mimetic peptide 37 pA at 100 μg/ml or with the control peptide 40 P at 100 μg/ml. The incubation was conducted in M199 for 2 hrs at 37° C. with gentle mixing. LDL and the peptides were subsequently re-isolated as in FIG. 1. Cocultures of artery wall cells were incubated with sham-treated LDL (Sham LDL), or LDL that was incubated with the apo A-I mimetic peptide (LDL after 37 pA), or with the control peptide (LDL after 40 P), sham-treated 37 pA (37 pA sham), or sham-treated 40 P (40 P sham). To other coculture wells was added reconstituted LDL that was prepared by incubating "LDL after 37 pA" plus the lipids extracted from "37 pA after LDL" (37 pA lipids after LDL+LDL after 37 pA). These additions were incubated with human artery wall cocultures for 8 hrs in the presence of 10% LPDS. The supernatants were collected and analyzed for lipid hydroperoxide levels (Panel A). The cocultures were then washed and were incubated with culture medium without serum or LPDS for 8 hrs. The conditioned medium was then collected and analyzed for monocyte chemotactic activity (Panel B). The data indicate mean±SD of values obtained from quadruplicate cocultures in three separate experiments. Asterisks indicate p<0.0014.

FIGS. 4A and 4B demonstrate that "LDL after A-I" could not be oxidized by a coculture of human artery wall cells. The data in FIGS. 3A through 3C represent the mean±SD of those obtained in seven out of seven experiments using LDL taken from seven different normal individuals and using different cocultures and monocytes taken from different donors. Thus, these results are highly reproducible and demonstrate in FIG. 4A that the artery wall cells were unable to oxidize "LDL after A-I". However, if the lipid extract from "A-I after LDL" was added back to "LDL after A-I", it was readily oxidized (FIG. 3A). Also, as shown in FIG. 2, "LDL after A-I" did not stimulate monocyte adherence (FIG. 3B) or chemotaxis (FIG. 3C). However, when the lipid extract from "A-I after LDL" was added back to "LDL after A-I" the reconstituted LDL induced monocyte adherence (FIG. 3B) and chemotaxis (FIG. 3C) to the same degree as sham treated LDL. Results that were highly similar to those shown in FIG. 3C were obtained when monocyte chemotactic protein 1 levels were measured by ELISA (data not shown).

The ability of apo A-I to bind lipids has been determined to be a function of its specific α-helical structure (Palgunachari et al. (1996) *Arterioscler. Thromb. Vascul. Biol.* 16: 328-338). Anantharamaiah and colleagues have synthesized apo A-I peptide mimetics that have been extensively characterized (Garber et al. (1992) *Arterioscler. Thromb.* 12: 886-894; Anantharamaiah (1986) *Meth. Enz.* 128: 627-647). One of these peptide mimetics is known as 37 pA with the amino acid sequence DWL KAF YDK VAE KLK EAF PDW LKA FYD KVA EKL KEA F (SEQ ID NO: 1). A peptide with the same amino acid sequence as 37 pA but containing three extra amino acid residues [aspartic acid (D), glutamic acid (E), and proline (P)] at the N-terminal that prevents the α helix formation necessary for lipid binding has also been constructed by this group using previously published methods (Anantharamaiah (1986) *Meth. Enz.* 128: 627-647). This control peptide, known as 40 P, binds lipids poorly compared to 37 pA. As shown in FIGS. 4A and 4B, after LDL had been incubated with and then separated from the apo A-I peptide mimetic 37 pA, the LDL ("LDL after 37 pA") was resistant to oxidation by the artery wall cells (FIG. 4A) and did not induce monocyte chemotactic activity (FIG. 4B). However, if the lipid extract from the peptide after incubation with the lipoprotein ("37 pA after LDL") was added back to "LDL after 37 pA", it was readily oxidized (FIG. 4A). In contrast, "LDL after 40 P" showed no reduction in LDL oxidation by the artery wall cells (FIG. 4A) and there was no reduction in LDL-induced monocyte chemotaxis (FIG. 4B). Thus, both apo A-I and its peptide mimetic 37 pA were able to remove lipids from freshly isolated LDL that rendered the LDL resistant to oxidation by human artery wall cells and prevented LDL-induced monocyte chemotaxis.

The "Seeding Molecules" in Freshly Isolated LDL that are Removed by Apo A-I Include 13-HPODE and 15-HPETE.

Figure 5:
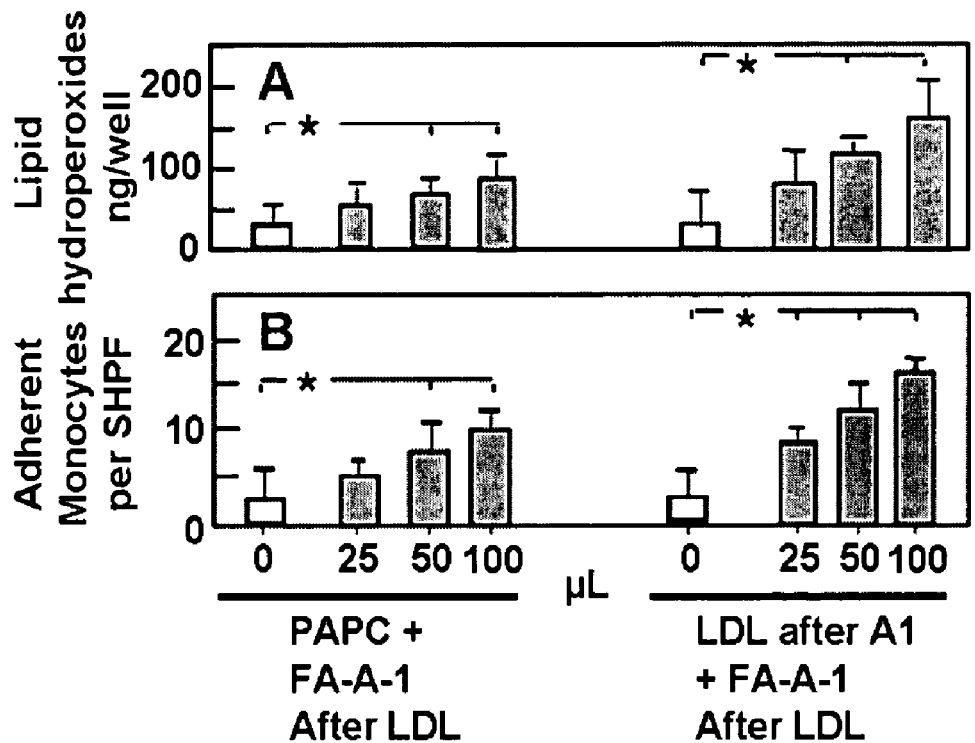
FIG. 5, panels A, B, C, and D, show the bioactivity of lipids extracted by apo A-I-Freshly isolated LDL (1 mg/ml) was incubated with apo A-I (100 µg/ml) and re-isolated as indicated in FIG. 1. Lipids were extracted from "A-I after LDL" by chloroform-methanol extraction and separated with solid phase extraction chromatography as described in Methods. The fatty acid (FA) or neutral lipid (NL) fractions were evaporated to dryness and were incubated with 200 µl of M199 containing 10% LPDS at 37° C. for 5 minutes with intermittent gentle vortexing. Fatty acids (FA-A-I after LDL, Panel A and Panel B), or neutral lipids (NL-A-I after LDL, Panel C and Panel D), were then incubated at the indicated quantities with either 100 µg PAPC or 250 µg "LDL after A-I" in a total volume of 1 ml of M199 containing 10% LPDS at 37° C. for 3 hrs. This treated PAPC or LDL in M 199 containing 10% LPDS was then incubated with HAEC at 37° C. for 4 hrs. The supernatants were removed and assayed for lipid hydroperoxide content (Panel A and Panel C) as described herein. The cells were washed and monocyte adhesion was determined (Panel B and Panel D) as described herein.
Figure 5:
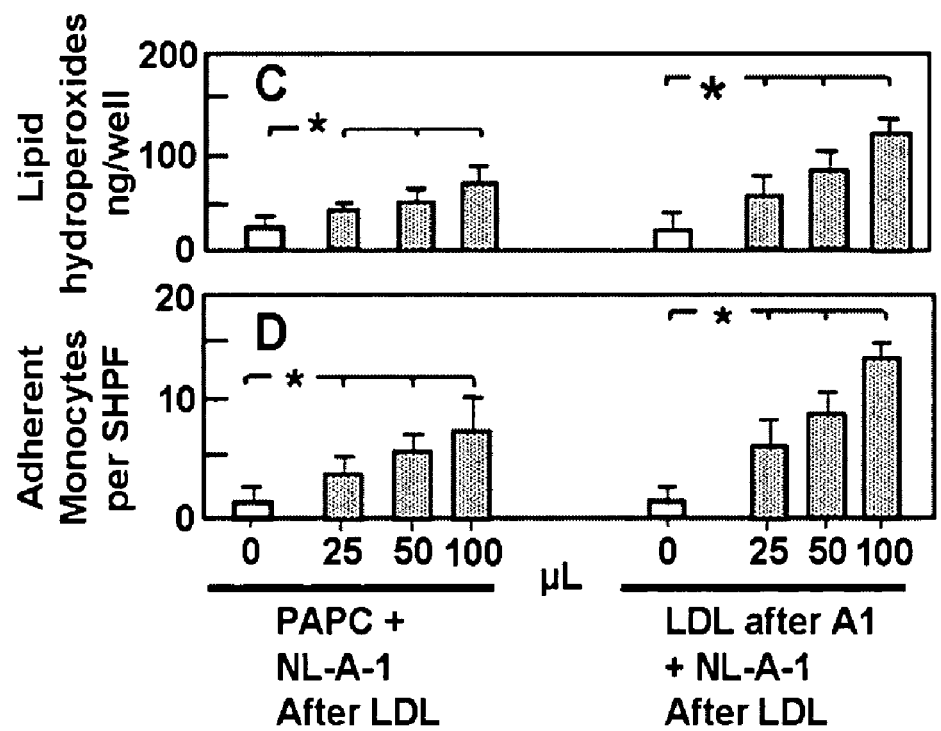

To identify biologically active lipids associated with LDL that was rapidly isolated by FPLC in the presence of 20 μM BHT as indicated in FIG. 2, lipids were extracted from "A-I after LDL". These lipids were separated by solid phase extraction chromatography. The neutral lipid or fatty acid fractions were then added to cocultures together with either PAPC a phospholipid present in LDL or to "LDL after A-I". Addition to the cocultures of PAPC or "LDL after A-I" did not stimulate lipid hydroperoxide formation or monocyte chemotactic activity (FIG. 5, panels A-C, open bars). However, addition to PAPC or to "LDL after A-I" of either the fatty acid fraction (FIG. 5, panels A and B, solid bars) or the neutral lipid fraction (FIG. 5, panels C and D, solid bars) extracted from "A-I after LDL" induced a dose dependent increase in the formation of lipid hydroperoxides and monocyte chemotaxis. These experiments indicated that apo A-I removed lipids from freshly isolated LDL that was required for the artery wall cells to oxidize both PAPC and LDL.

Addition of either the fatty acid or neutral lipid fractions recovered from "A-I after LDL" resulted in the oxidation of PAPC and "LDL after A-I" by the artery wall cells.

Figure 6:
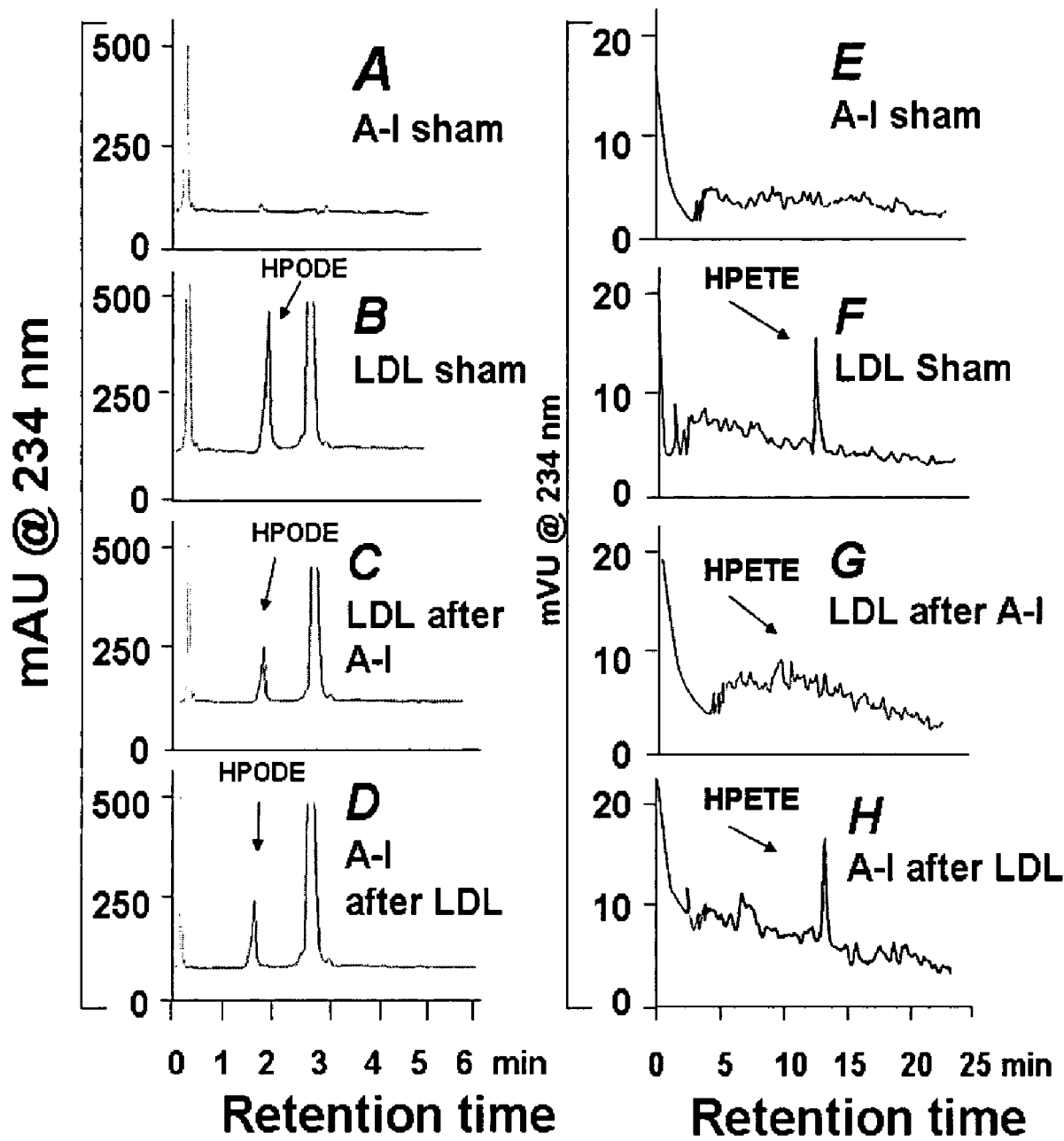
FIG. 6, panels A through H, illustrate the removal of 13-HPODE and 15-HPETE by apo A-I from LDL. Freshly isolated LDL (1 mg/ml) was incubated alone (LDL sham), or with apo A-I (100 µg/ml) in M199 for 2 hrs, with gentle mixing. For controls, 100 µg/ml apo A-I was incubated alone in M 199 for 2 hrs (A-I Sham, Panel A and Panel E) or 1 mg/ml freshly isolated LDL was incubated alone in M 199 for 2 hrs (LDL Sham, Panel B and Panel F) with gentle mixing at 37° C. The LDL and apo A-I were then re-isolated by centrifugation using Millipore molecular weight cut-off filters (100 kDa). Lipids were extracted from apo A-I and from LDL and were analyzed by reverse phase HPLC. Panel C and Panel G demonstrate the decrease in the 13-HPODE and 15-HPETE peaks in LDL following incubation with apo A-I (LDL after A-I) and FIG. 6D and FIG. 6H demonstrate the increase in 13-HPODE and 15-HPETE respectively in the lipid extract from apo A-I after incubation with and separation from LDL (A-I after LDL).

To further identify the fatty acids, freshly isolated LDL was incubated with or without apo A-I and then separated by centrifugation. Following incubation with apo A-I, the lipids were extracted from the LDL and from the apo A-I. Lipids were also extracted from apo A-I that was incubated without LDL (A-I sham) and from LDL that was not incubated with apo A-I (LDL sham). The extracted lipids were then fractionated by reverse phase HPLC. Apo A-I that had not been incubated with LDL contained little if any 13-HPODE (FIG. 6, panel A) or 15-HPETE (FIG. 6, panel E). In contrast, freshly isolated LDL that had been incubated without apo A-I (LDL sham) contained 13-HIPODE and an unidentified nearby peak (FIG. 6, panel B), and also contained 15-HPETE (FIG. 6, panel F). "LDL after A-I" contained substantially less 13-HPODE relative to the nearby unidentified peak (compare the 13-BIPODE peak relative to the unidentified peak in FIG. 6, panels B and C) and markedly less 15-HPETE (FIG. 6, panel G). FIG. 6, panels D and H, demonstrate that 13-HPODE and 15-HPETE, respectively, were transferred to apo A-I. Additional analyses using mass spectrometry also confirmed the presence of significant amounts of HPODE and HPETE in freshly isolated LDL, both of which were effectively removed by incubation with apo A-I (data not shown). Analysis of the lipid extract from "A-I after LDL" by ESI-MS in the negative ion mode demonstrated the presence of an ion with m/z 311 indicating the presence of HPODE (data not shown). An ion present in less abundance compared with that for HPODE and with m/z 335 was also observed, indicating the presence of HIPETE in the lipids of "A-I after LDL" (data not shown). The lipid extract of "A-I after LDL" also contained a relatively large quantity of an ion with nz/z 317 indicating the presence of a dehydration product of HPETE i.e. the loss of one molecule of water (data not shown). Analysis by MS/MS of the lipid extract from freshly isolated LDL that was not treated with apo A-I confirmed the presence of HPODE (data not shown). However, HPETE was not detected in these samples (data not shown). Since HPETE was readily detected in "A-I after LDL" by both HPLC and MS/MS, we deduce that: 1) treatment of apo A-I may have concentrated the HPETE allowing its detection; 2) HPODE may be present in higher concentrations in freshly isolated LDL than is HPETE.

Addition of authentic 13(S)-HPODE to freshly isolated LDL as described in Methods increased the formation of lipid hydroperoxides when the LDL was added to HAEC and also increased monocyte adherence to HAEC (data not shown).

13(S)-HPODE is the product of lipoxygenase activity on linoleic acid (55,56). Since the major unsaturated fatty acid in LDL is linoleic acid, freshly isolated LDL was incubated with or without soybean lipoxygenase. After incubation with and then separation from the soybean lipoxygenase as described herein, the LDL was added to HAEC. The LDL that was incubated with and then separated from soybean lipoxygenase significantly increased the formation of lipid hydroperoxides in the culture supernatants and also increased monocyte adherence to HAEC as compared to LDL incubated without soybean lipoxygenase (data not shown).

Taken together these experiments indicate that the "seeding molecules" in freshly isolated LDL that are removed by apo A-I may include HPODE and HPETE.

Freshly Isolated LDL from Mice that are Genetically Susceptible to Atherosclerosis are Highly Susceptible to Oxidation by Human Artery Wall Cells and are Rendered Resistant to Oxidation by Human Apo A-I.

Figure 7:
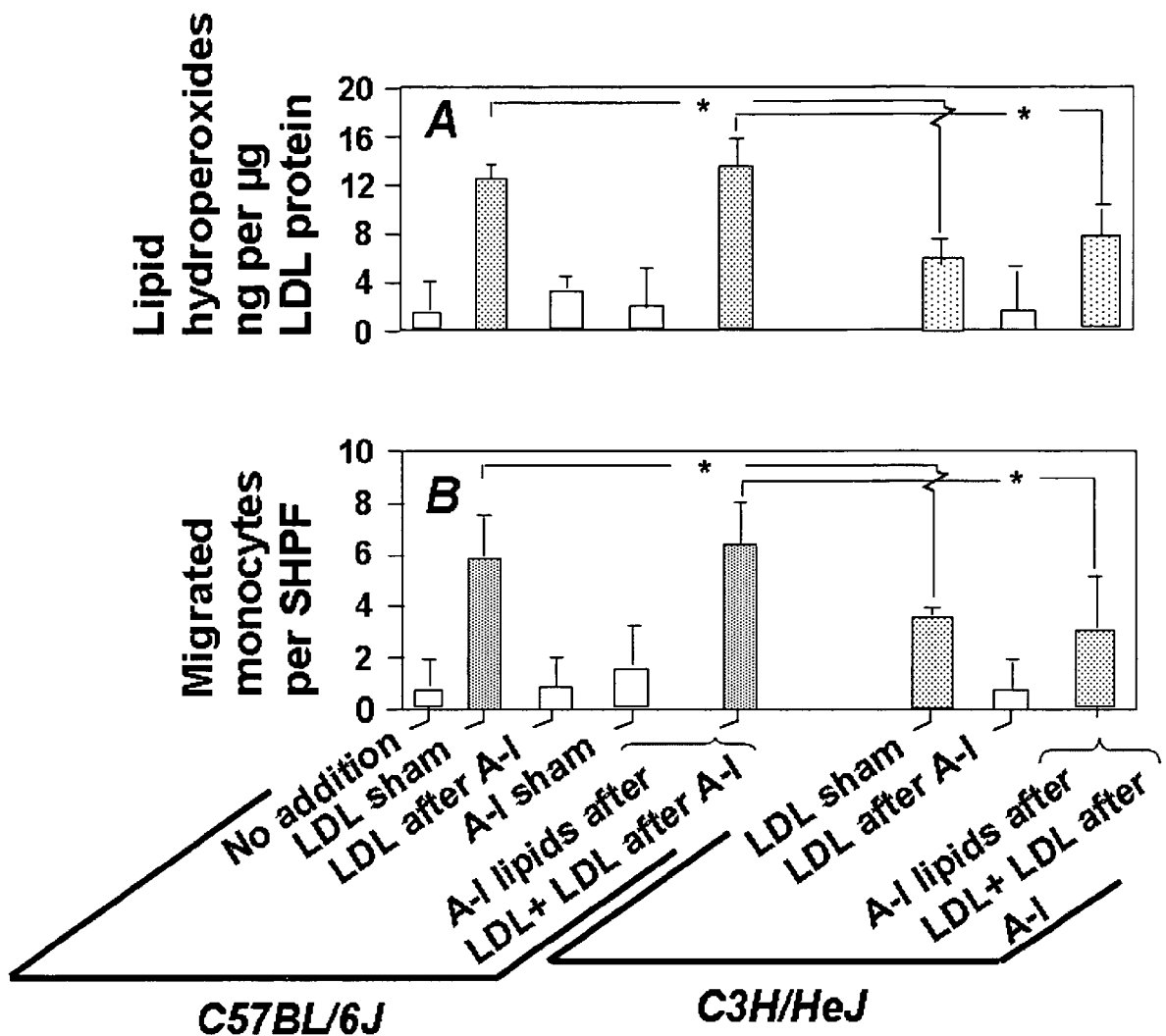
FIG. 7, panels A and B, illustrate seeding molecules in LDL from C57BL/6 and C3H/HeJ mouse strains on a chow diet. LDL was isolated from plasma obtained from groups (n=5 each group) of the lesion susceptible C57BL/6 (BL/6) and from the lesion resistant C3H/HeJ (C3H) mice. The LDL was incubated (at 100 µg/ml) with human apo A-I (at 100 µg/ml) with gentle mixing at 37° C. and then re-isolated by FPLC as indicated in FIG. 2. Reconstitution of LDL with lipids removed by apo A-I was carried out as described in FIG. 3 and incubated with aortic wall cell cocultures. The abbreviations are the same as in FIG. 3. Panel A shows data on lipid hydroperoxides formed and Panel B demonstrates the chemotactic activity that was induced. The values shown are mean±SD of quadruplicate cocultures. The asterisks indicate p<0.0015.

When fed an atherogenic diet, C57BL/6J (BL/6) mice develop fatty streak lesions in their aorta while C3H/HeJ (C3H) mice do not, despite equivalent levels of apo B containing lipoproteins (Paigen et al. (1987) *Proc. Natl. Acad. Sci.* USA 84: 3763-3767; Ishida et al. (1991) *J. Lipid Res.* 32: 559-568). We previously have presented evidence to suggest that the lesion-susceptible BL/6 mice are under oxidative stress Shih et al. (1996) *J. Clin. Invest.* 97: 1630-1639; Shih et al. (1998) *Nature* 394: 284-287; Liao et al. (1994) *J. Clin. Invest.* 94: 877-884). A logical consequence of this hypothesis might be increased susceptibility to oxidation of LDL from the BL/6 mice compared to LDL from the lesion resistant C3H mice. On a low-fat chow diet the two strains of mice have similar low levels of LDL and the lesion susceptible BL/6 mice have higher levels of HDL (Paigen et al. (1987) *Proc. Natl. Acad. Sci.* USA 84: 3763-3767). To test our hypothesis we incubated freshly isolated LDL from the two strains, both of which were on the low-fat chow diet, with and without human apo A-I and then separated the LDL and apo A-I and incubated them with the human artery wall cell cocultures. As shown in FIG. 7, panels A and B, LDL incubated without apo A-I (LDL Sham) from the lesion sensitive BL/6 mice was more readily oxidized by the artery wall cells than was the case for the LDL from the lesion resistant C3H mice (FIG. 7, panel A). In contrast, "LDL after A-I" from both the lesion sensitive BL/6 and the lesion resistant C3H mice were resistant to oxidation by the artery wall cells (FIG. 7, panel A). On the other hand, if the lipids were extracted from "A-I after LDL", and added back to "LDL after A-I" the reconstituted LDL was oxidized by the artery wall cells to the same degree as was the case for the sham-treated LDL (FIG. 7, panel A). Similar results were obtained for LDL-induced monocyte chemotaxis (FIG. 7, panel B). The data in FIG. 7, panels A and B, indicate that the difference in the ability of artery wall cells to oxidize LDL from the lesion sensitive BL/6 mice compared to LDL from the C3H mice is due to lipids in their LDL that can be removed by apo A-I. These data also indicate that this difference is present while the animals are on the low-fat chow diet.

Injection of Human APo A-I (but not Human Apo A-II) into Mice Renders the Mouse LDL Resistant to Oxidation by Human Artery Wall Cells.

Figure 8:
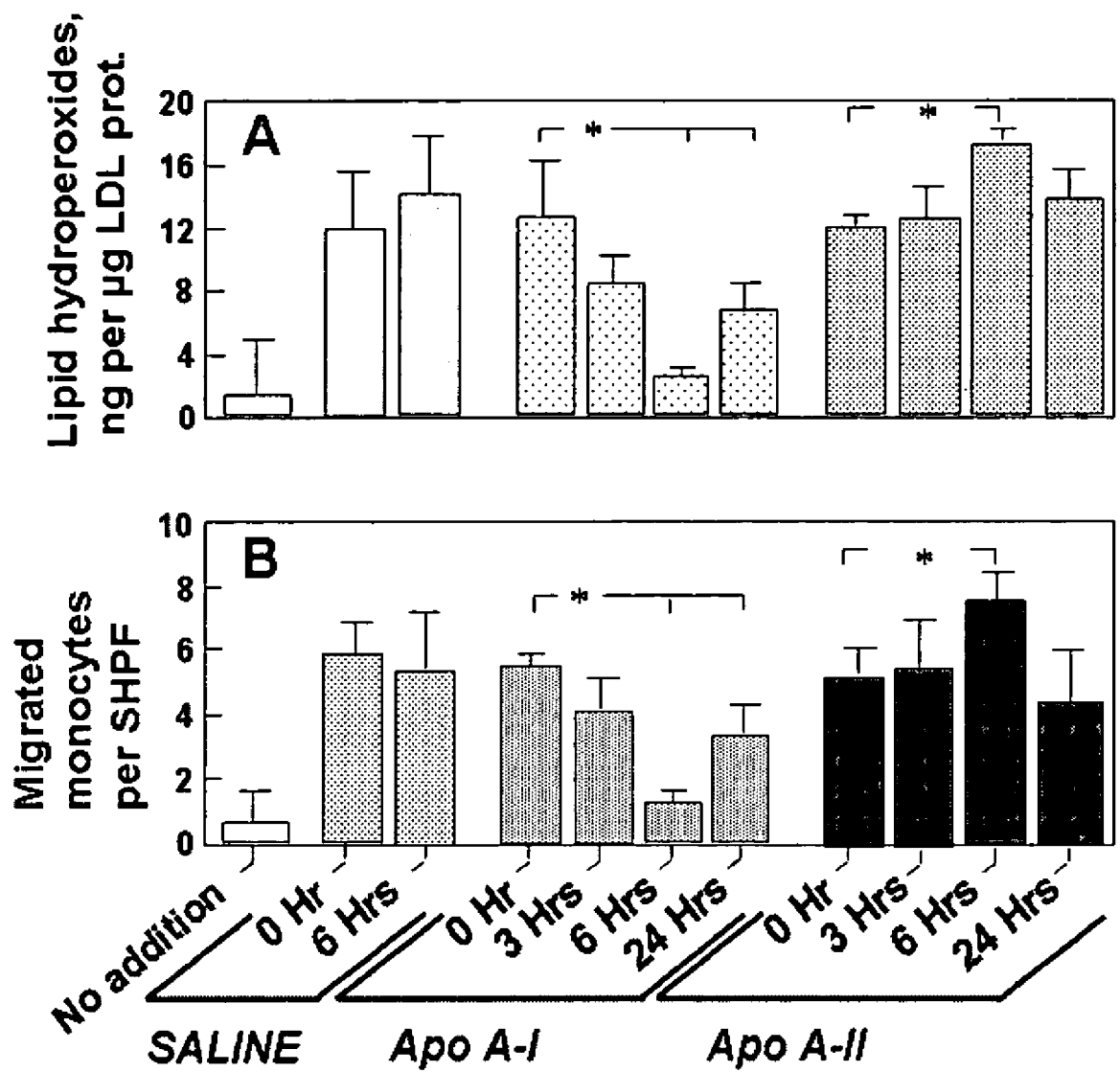
FIG. 8, panels A and B, show that injection of apoA-I (but not apoA-II) into mice renders the mouse LDL resistant to oxidation by human artery wall cells. Groups of C57BL/6 mice (n=5) were injected in the tail vein with 100 µg per animal of apo-AI, apoA-II or with saline alone. Blood samples were removed at time points, LDL was isolated and incubated with cocultures for 8 hrs. Culture supernatants were assayed for lipid hydroperoxides (Panel A) and for monocyte chemotactic activity (Panel B) as described in Methods. The figure depicts the mean±SD of quadruplicate samples from a representative experiment. The asterisks indicate p<0.0001 as compared to 0 time. Identical results were obtained in two out of two separate experiments.

To test the ability of apo A-I to alter the potential oxidative state of LDL in vivo, we injected 100 μg of apo A-I or apo A-II or saline alone into mice via their tail veins. Blood was removed immediately (0 hr) or 3, 6, or 24 hours after injection. LDL was isolated by FPLC and incubated with human artery wall cocultures and the formation of lipid hydroperoxides and monocyte chemotactic activity was determined. FIG. 8, panel A demonstrates that the freshly isolated LDL from BL/6 mice that had been injected with apo A-I three to six hours earlier was resistant to oxidation by human artery wall cells and this resistance persisted for up to 24 hours (FIG. 8, panel A). In contrast, the LDL obtained immediately after injection (0 hr) or 6 hours after injection of saline alone, or 6 hours after injection of apo A-II did not render the mouse LDL resistant to oxidation by the artery wall cells (FIG. 8, panel A). Similar results were obtained for monocyte chemotactic activity (FIG. 8, panel B). PON activity in plasma and HDL increased by approximately 20% six hours after injection of apo A-I but did not change after injection of apo A-II (data not shown). Thus, as was the case for the in vitro studies above, apo A-I injected in vivo (but not apo A-II) was able to dramatically decrease the oxidation of LDL.

Infusion of Human APO A-I into Humans Renders their LDL Resistant to Oxidation by Human Artery Wall Cells.

Figure 9:
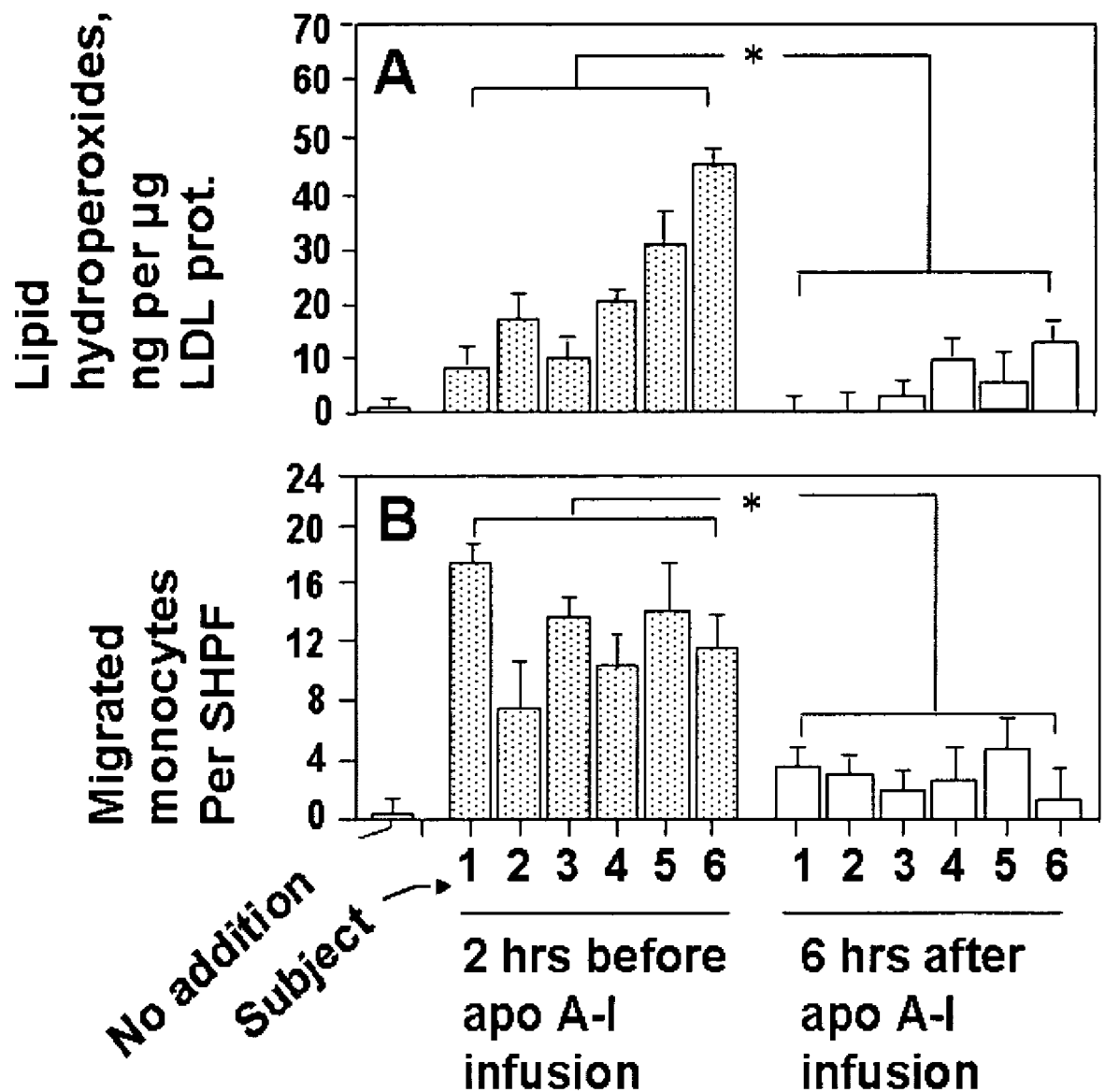
FIG. 9, panels A and B, show that infusion of human apo A-I into humans renders their LDL resistant to oxidation by human artery wall cells. Six individuals (described herein) were infused with human apo A-I/phosphatidylcholine discs at 40 mg apo A-I/kg body weight during a 4-hr period. Plasma was prepared 2 hrs before and 6 hrs following the start of the infusion (i.e., 2 hrs after completion of the infusion). LDL was isolated by FPLC and incubated (at 100 µg/ml) with cocultures for 8 hrs. Culture supernatants were collected and subjected to lipid extraction and were assayed for hydroperoxide content (Panel A). The cocultures were washed and incubated in culture medium without serum or LPDS for 8 hrs and the conditioned medium was analyzed for monocyte chemotactic activity (Panel B). Mean±SD of quadruplicate cocultures are presented and asterisk indicates p<0.0173 for panel A; p<0.0077 for panel B.

As indicated above in FIG. 8, panel A, injection of apo A-I into mice rendered their LDL resistant to oxidation by the artery wall cells. FIG. 9, panel A and FIG. 9, panel B, describes a parallel study in humans. Blood was taken from six healthy subjects (one with mildly increased levels of triglycerides, 176 mg/dl, as indicated in Methods) two hours before and six hours after infusion of apo A-I. LDL was isolated from the plasma at each time point and incubated with human artery wall cell cocultures. As shown in FIG. 9, panel A, in six out of six subjects, the LDL isolated six hours after the infusion of apo A-I was much more resistant to oxidation by the artery wall cells as compared to the LDL two hours before the infusion. Similar results were obtained for LDL induced monocyte chemotactic activity (FIG. 9, panel B) although the decrease in oxidation for subject 4 was less than the decrease in LDL- induced monocyte chemotactic activity. PON activity in plasma and HDL was increased by approximately 20% six hours after the infusion as compared to two hours before the infusion (data not shown). These data indicate that as was the case for the mice, injection of apo A-I into humans rendered their LDL resistant to oxidation by human artery wall cells.

HDL or HDL Associated Enzymes Render LDL Resistant to Oxidation by Human Artery Wall Cells.

Figure 10:
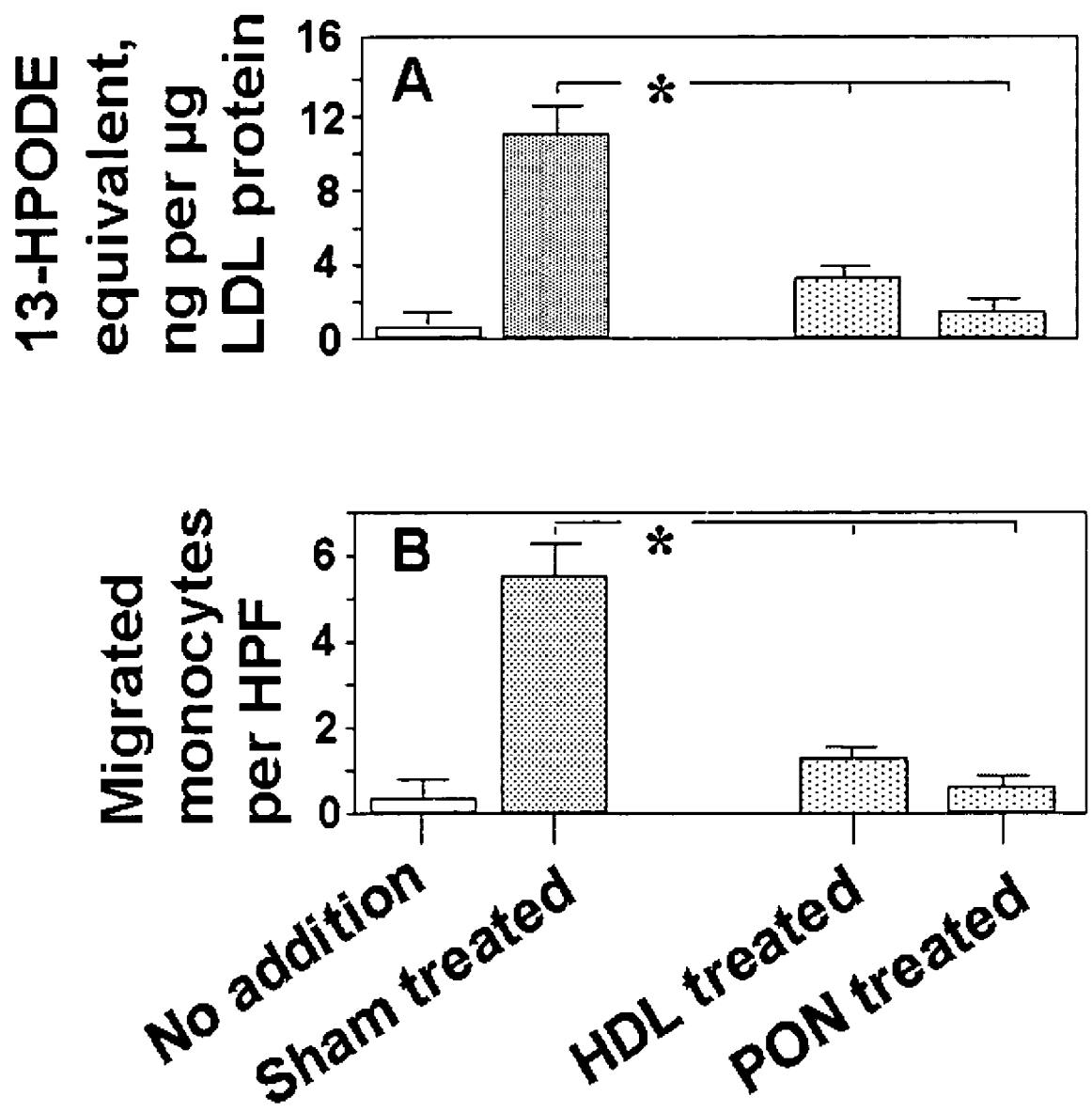
FIG. 10, panels A and B, show that HDL or HDL associated enzymes render LDL resistant to oxidation by human artery wall cells. Freshly isolated LDL was incubated at 250 µg/ml with buffer (Sham treated LDL), with HDL at 350 µg/ml (HDL treated LDL) or with purified PON at $1 \times 10^{-2}$ U/ml (PON treated LDL). The incubation was conducted in M199 for 3 hrs at 37° C. with gentle mixing. LDL was subsequently re-isolated by centrifugation using Millipore molecular weight cut-off filters (100 kDa) and was incubated with human artery wall cocultures for 8 hrs in the presence of 10% LPDS. The supernatants were removed and analyzed for lipid hydroperoxides (Panel A); the cocultures were washed and incubated with culture medium without serum or LPDS. After 8 hrs the medium was collected and analyzed for monocyte chemotactic activity (Panel B). The data indicate mean±SD of values obtained from quadruplicate cocultures in three separate experiments. Asterisks indicate significance at the level of p<0.0008.

To test the ability of whole HDL and its components other than apo A-I, such as PON, to render LDL resistant to oxidation by artery wall cells, LDL was incubated with or without HDL, or PON, as described herein and then separated from these and incubated with human artery wall cell cocultures. Incubation with HDL, or PON, rendered the LDL resistant to oxidation by the artery wall cells compared to sham treated LDL (FIG. 10, panel A). Similar results were obtained for LDL-induced monocyte chemotactic activity (FIG. 10, panel B). Thus, HDL and its associated enzyme PON can render LDL resistant to oxidation by artery wall cells.

Discussion.

The data presented in this example demonstrate a role for HDL and its components, apo A-I and PON in regulating the first step in a three-step process that leads to the formation of mildly oxidized LDL. Parthasarathy (1994) *Modified Lipoproteins in the Pathogenesis of Atherosclerosis*. Austin, Tex.; R.G. Landes Co. pp. 91-119; Parthasarathy (1994) *Free Radicals in the Environment, Medicine and Toxicology*. edited by H. Nohl, H. Esterbauer, and C. Rice Evans. Richelieu Press, London. pp. 163-179; Witztum and Steinberg (1991) *J. Clin. Invest*. 88: 1785-1792; Witztum (1994) *Lancet* 344: 793-795; Chisolm (1991) *Clin. Cardiol*. 14: 125-130; and Thomas and Jackson (1991) *J. Pharmacol. Exp. Therap*. 256: 1182-1188, hypothesized that LDL must be "seeded" with reactive oxygen species before it can be oxidized. Spector and colleagues (Spector et al. (1988) *Prog. Lipid Res*. 27: 271-323; Alexander-North et al. (1994) *J. Lipid Res*. 35: 1773-1785) have demonstrated that the lipoxygenase pathway is active in artery wall cells, and Parthasarathy emphasized the possibility that hydrogen peroxide or its lipoperoxide equivalent (Parthasarathy et al. (1989) *Proc. Natl. Acad. Sci*. USA 86: 1046-1050; Parthasarathy (1994) *Modified Lipoproteins in the Pathogenesis of Atherosclerosis*. Austin, Tex.; R.G. Landes Co. pp.91-119; Parthasarathy (1994) *Free Radicals in the Environment, Medicine and Toxicology*. edited by H. Nohl, H. Esterbauer, and C. Rice Evans. Richelieu Press, London. pp. 163-179) may play an important role in "seeding" LDL. The recent findings of Cyrus et al. (1999) *J. Clin. Invest*.103: 1597-1604) that disruption of the 12/15-lipoxygenase gene diminished atherosclerosis in apoE-deficient mice are consistent with this hypothesis and the data in this example.

We found that freshly isolated LDL from mice on a chow diet that are genetically susceptible to the development of atherosclerosis was more readily oxidized by artery wall cells than was the case for LDL taken from mice that are genetically resistant to the development of atherosclerosis. The LDL from both strains of mice was rendered resistant to oxidation by the artery wall cells after apo A-I treatment (FIG. 7, panels A and B), and the levels of oxidation of LDL after treatment with apo A-I were not significantly different for the two strains (FIG. 7, panels A and B). This may indicate that the genetic difference in susceptibility to develop atherosclerosis may be due, in part, to a difference in the level of "seeding molecules" in the LDL of these two mouse strains.

The in vitro ability of apo A-I (FIG. 3 and FIG. 7) and an apo A-I peptide mimetic (FIG. 4, panels A and B) to render LDL resistant to oxidation by artery wall cells was also demonstrated to apply in vivo in both mice (FIG. 8, panels A and B) and in humans (FIG. 9, panels A and B). In mice, within three hours of injection of apo A-I, LDL was rendered resistant to oxidation by artery wall cells and this state of protection persisted for up to 24 hours (FIG. 8, panels A and B). In contrast to the case for apo A-I, injection of apo A-II did not protect LDL against oxidation by artery wall cells (FIG. 7, panel A). In humans, infusion of apo A-I into six out of six men rendered their LDL resistant to oxidation by artery wall cells within 6 hours of the infusion (FIG. 8, panel A).

Not only was apo A-I capable of favorably altering the susceptibility of LDL to oxidation by artery wall cells but so was HDL itself and the HDL associated enzyme, PON. Aviram and colleagues recently demonstrated that PON has peroxidase activity (Aviram et al. (1998) *J. Clin. Invest*. 101: 1581-1590; Aviram et al. (1998) *Arterioscler. Thromb. Vascul. Biol*. 18: 1617-1624) which in part may explain the role of PON in protecting against atherosclerosis in mouse models (Shih et al. (1996) *J. Clin. Invest*. 97: 1630-1639; Shih et al. (1998) *Nature* 394: 284-287) and in epidemiological studies (Serrato and Marian (1995*J. Clin. Invest*. 96: 3005-3008; Mackness et al. (1998) *Curr. Opin. Lipidol*. 9: 319-324; Heinecke and Lusis (1998) *Amer. J. Hum. Genet*. 62: 20-24). The recent paper by Dansky and colleagues (Dansky et al. (1999) *J. Clin. Invest*. 104: 31-39) suggested that there was benefit to over expression of apo A-I in apo E deficient mice without an increase in PON activity. However, as acknowledged by the authors of this study (Id.), they limited their experiments to the first 8 weeks of life. Aviram and colleagues reported that serum PON activity declined in apo E-deficient mice after 3 months of age, coincident with increases in aortic lesion area and serum lipid peroxidation (Aviram et al. (1998) *J. Clin. Invest*. 101: 1581-1590). The mice studied by Plump and colleagues (Plump et al. (1994) *Proc. Natl. Acad. Sci*. USA 91: 9607-9611) were sacrificed at 4 or 6 months of age when Aviram's data would suggest that PON activity would be reduced. Dansky and colleagues (Dansky et al. (1999) *J. Clin. Invest*. 104: 31-39) also reported that lipid retention in the artery wall and monocyte adherence to the endothelium were not different at eight weeks and concluded that the benefit of apo A-I was limited to a later time in lesion development. It should be noted that Dansky and colleagues (Id.) did not measure monocyte adherence but measured instead CD11a adherence, which is not specific for monocytes. Additionally, Dansky and colleagues (Id.) used mice with a genetically mixed background for most of their experiments and did not measure monocyte/macrophages in the subendothelial space. Based on our data, we would predict that apo A-I over expression might reduce the susceptibility of LDL to oxidation independent of any change in PON activity. However, we saw approximately a 20% increase in PON activity six hours after injection of apo A-I (but not apo A-II) into mice and a similar small increase in humans six hours after infusion of apo A-I Sevanian and colleagues (Sevanian et al. (1997) *J. Lipid Res.* 38:419-428) reported increased levels of cholesterol oxides in LDL. Our finding (FIG. 5) that the neutral lipid extracted from "A-I after LDL" could restore the ability of artery wall cells to oxidize "LDL after A-I" are consistent with Sevanian's observations. Our results on the fatty acid fractions extracted from "A-I after LDL" (FIG. 5, panels A-C, and FIG. 6, panels A-H) indicate that metabolites of the linoleic and arachidonic acids can also act as LDL "seeding molecules". Review of FIG. 6, panels A-H reveals that "LDL after A-I" still contained a detectable level of 13-HPODE. However, this level was not sufficient to allow "LDL after A-I" to be oxidized by human artery wall cells (FIGS. 3, 5, 7, 8, and 9). Since the step-wise addition of either the neutral lipid or fatty acid fractions from "A-I after LDL" to "LDL after A-I" restored its ability to be oxidized by the artery wall cells (FIG. 5), we conclude that there is a critical threshold for the "seeding molecules" that is necessary for oxidation.

Stocker and colleagues (Garner et al. (1998) *J. Biol. Chem.* 273: 6080-6087; Garner et al. (1998) *J. Biol. Chem.* 273: 6088-6095) demonstrated that both apo A-I and apo A-II can reduce cholesteryl ester hydroperoxides via a mechanism that involves oxidation of specific methionine residues (Garner et al. (1998) *J. Biol. Chem.* 273: 6088-6095). In our experiments only apo A-I and not apo A-II was able to reduce the oxidation of LDL after injection into mice (FIG. 8). These results suggest that the mechanism of protection of apo A-I in our studies was different from that investigated by Stocker and colleagues (Garner et al. (1998) *J. Biol. Chem.* 273: 6080-6087; Garner et al. (1998) *J. Biol. Chem.* 273: 6088-6095). HDL has been demonstrated to be a strong inverse predictor of risk for atherosclerosis (Miller and Miller (1975) *Lancet* 1(7897): 16-19). It has been shown to reduce atherosclerosis in animal models when infused (Badimon et al. (1990) *J. Clin. Invest.* 85:1234-1241) and when associated with the over expression of apo A-I (Plump er al. (1994) *Proc. Nail. Acad. Sci.* USA 91: 9607-9611). However, the over expression of apo A-II has been demonstrated to enhance atherosclerosis (Castellani et al. 1997 *J. Clin. Invest.* 100: 464-474; Warden et al. (1993) *Science.* 261: 469-472; Hedrick et al. (1993) *J. Biol. Chem.* 268: 20676-20682). The studies reported here are consistent with these published reports and indicate that apo A-I but not apo A-II is capable of removing "seeding" molecules from freshly isolated LDL.

In example 2 we present evidence that normal HDL and its components can also inhibit the second and third steps in the formation of mildly oxidized LDL.

Example 2

Normal HDL Inhibits Three Steps in the Formation of Mildly Oxidized LDL- Steps 2 and 3

In this example, treatment of human artery wall cells with apo A-I (but not apo A-II), with an apo A-I peptide mimetic, or with HDL, or paraoxonase, rendered the cells unable to oxidize LDL. Addition of 13(S)-hydroperoxyoctadecadienoic acid [13(S)-HPODE] and 15(S)-hydroperoxyeicosatetraenoic acid [15(S)-HPETE] dramatically enhanced the non-enzymatic oxidation of both 1-palmitoyl-2-arachidonoyl-sn-glycero-3-phosphocholine (PAPC) and cholesteryl linoleate. On a molar basis 13(S)-HPODE and 15(S)-HPETE were approximately two orders of magnitude greater in potency than hydrogen peroxide in causing the formation of biologically active oxidized phospholipids (m/z 594, 610, and 828) from PAPC. Purified paraoxonase inhibited the biologic activity of these oxidized phospholipids. HDL from 10 out of 10 normolipidemic patients with coronary artery disease, who were neither diabetic nor on hypolipidemic medications, failed to inhibit LDL oxidation by artery wall cells and failed to inhibit the biologic activity of oxidized PAPC while HDL from 10 out of 10 age and sex matched controls did.

We conclude that: (a) Mildly oxidized LDL is formed in three steps, each of which can be inhibited by normal HDL and, (b) HDL from at least some coronary artery disease patients with normal blood lipid levels is defective both in its ability to prevent LDL oxidation by artery wall cells and in its ability to inhibit the biologic activity of oxidized PAPC.

Introduction.

We discovered that HDL but not apo A-I when added to human artery wall cell cocultures together with LDL prevented the oxidation of the LDL by the artery wall cells. In those experiments, the apo A-I was kept in the culture together with the artery wall cells and the LDL (Navab et al. (1991) *J. Clin. Invest.* 88: 2039-2046). Subsequently, in pursuing the mechanisms for the ability of HDL to protect LDL against oxidation by human artery wall cells, we discovered that if the apo A-I was incubated with the cells and then removed prior to the addition of the LDL, the artery wall cells were then unable to oxidize the added LDL. This suggested to us that apo A-I might be able to remove from cells not only cholesterol and phospholipids but perhaps oxidized lipids as well. These preliminary findings prompted us to perform the studies detailed in this example.

The experiments detailed in this example and in example 1 have led us to propose that the biologically active lipids in mildly oxidized LDL are formed in a series of three steps. The first step is the seeding of LDL with products of the metabolism of linoleic and arachidonic acid as well as with cholesteryl ester hydroperoxides. The evidence for the first step was presented in example 1. In this example we present evidence regarding the second step i.e., trapping of LDL in the subendothelial space and the delivery to this trapped LDL of additional reactive oxygen species derived from nearby artery wall cells.

Stocker and colleagues have presented indirect evidence that lipoxygenases mediate the peroxidation of cholesteryl linoleate largely by a non-enzymatic process (Neuzil et al. (1998) *Biochem*. 37: 9203-9210; Upston et al. (1997) *J. Biol. Chem.* 272: 30067-30074). We demonstrate in this example that the non-enzymatic oxidation of cholesteryl linoleate is greatly enhanced by the presence of 13-hydroperoxyoctadecadienoic acid [13(S)-HPODE]. We also propose in this example that the third step in the formation of mildly oxidized LDL is the non-enzymatic oxidation of LDL phospholipids that occurs when a critical threshold of "seeding molecules" (e.g., 13(S)-HPODE and 15-hydroperoxyeicosatetraenoic acid [15(S)-HPETE] is reached in the LDL. We present evidence in this example to indicate that when these "seeding molecules" reach a critical level, they cause the non-enzymatic oxidation of a major LDL phospholipid, 1-palmitoyl-2-arachidonoyl-sn-glycero-3-phosphocholine (PAPC). This results in the formation of the three biologically active oxidized phospholipids: 1-palmitoyl-2-oxovaleryl-sn-glycero-3-phosphocholine (POVPC, m/z 594), 1-palmitoyl-2-glutaryl-sn-glycero-3- phosphocholine (PGPC, m/z 610), and 1-palmitoyl-2-(5,6-epoxyisoprostane $E_2$)-sn-glycero-3-phosphocholine (PEIPC, m/z 828) (Watson (1999) *J. Biol. Chem.* 274: 24787-24798; Watson (1997) *J. Biol. Chem.* 272: 13597-13607). The experiments in this example also indicate that in contrast to the case for normal HDL, HDL taken from patients with coronary artery disease who showed normal blood lipid levels, were neither diabetic nor on hypolipidemic medications, did not protect LDL against oxidation by human artery wall cells and failed to inhibit the biologic activity of oxidized PAPC.

Materials and Methods.

Materials.

The arachidonic acid analogue, 5,8,11,14-eicosatetraynoic acid (ETYA) was obtained from Biomol (Plymouth Meeting, Pa.). Cholesteryl linoleate hydroperoxide (Ch18: 2:—OOH) standard was prepared by peroxidation of cholesteryl linoleate using tert-butyl hydroperoxide. Seventy percent tert-butyl hydroperoxide was added into the mixture of chloroform and methanol (2:1, v/v) containing 100 mg of cholesteryl linoleate. After peroxidation for 48 hrs at room temperature with mixing, the lipids were extracted by the Folch method (Folch et al. (1957) *J. Biol. Chem.* 226: 497-509) and separated by reverse phase high performance liquid chromatography (RP-HPLC) as described below. All other materials were from sources described in example 1.

Lipoproteins, Cocultures, Monocyte Isolation, Monocyte Chemotaxis Assays, and Monocyte Adhesion Assays.

These were prepared and/or performed as described in example 1.

Patients and Normal Subjects.

Blood samples were collected from patients referred to the cardiac catheterization laboratory at The Center for Health Sciences at the University of California, Los Angeles. After signing a consent form approved by the human research subject protection committee of the University of California, Los Angeles, the patient donated a fasting blood sample collected in a heparinized tube. LDL and/or HDL were isolated by FPLC from the blood samples collected from patients who had angiographically documented coronary atherosclerosis but who had normal total cholesterol (<200 mg/dl), LDL-cholesterol (<130 mg/dl), HDL-cholesterol (males >45 mg/dl, females >50 mg/dl), and triglycerides (<150 mg/dl), who were not on hypolipidemic medications and who were not diabetic. Data from some patients and some controls previously reported by us (Navab et al. (1997) *J. Clin. Invest.* 99: 2005-2019) have been included with additional new data. The inclusion of previously reported patients is explicitly indicated in the appropriate figure legend. HDL was isolated from each individual and paraoxonase activity was determined as previously described (Navab et al. (1997) *J. Clin. Invest.* 99: 2005-2019). The ability of the HDL from each subject to protect LDL against oxidation by human artery wall cell cocultures using techniques previously described was then determined (Navab et al. (1991) *J. Clin. Invest.* 88: 2039-2046; Navab et al. (1997) *J. Clin. Invest.* 99: 2005-2019). The LDL used for testing HDL's ability to protect LDL against oxidation by human artery wall cells was prepared from a normal donor and was aliquoted and cryopreserved in sucrose as previously described (Rumsey et al. (1992) *J. Lipid Res.* 33: 1551-1561). To determine the capacity of HDL to inactivate oxidized phospholipids, in some cases 100 µg/ml of oxidized PAPC (Navab et al. (1997) *J. Clin. Invest.* 99: 2005-2019) was incubated with 250 µg/ml of HDL in test tubes in 10% LPDS in M199 at 37° C. with gentle mixing. The HDL-Ox-PAPC mixture was then added to endothelial monolayers and monocyte binding was determined.

Effect of Over Expression of 15-Lipoxvpenase (15-LO) in Fibroblasts on the Removal of 13(S)-HPODE by apo A-I.

Fibroblasts that were transfected with vector alone or cells that over expressed 15-LO were a generous gift of Drs. Joe Witztum and Peter Reaven. In the present experiments, the fibroblasts were incubated with or without 100 µg/ml apo A-I. Following 3 hrs of incubation at 37° C. with gentle mixing, the culture supernatants were removed, apo A-I was separated by FPLC and the level of hydroperoxides determined in lipid extracts of the culture supernatants and in lipid extracts of apo A-I.

Effect of Lipoxygenase and Cyclooxygenase Inhibitors.

Human artery wall cocultures were preincubated with ETYA at a concentration of $10^{-8}$ mol/L or with cinnamyl-3,4-dihydroxy-α-cyanocynamate (CDC, from Biomol) at a concentration of $10^{-8}$ mol/L in M199 containing 10% LPDS for 30 min. The cocultures were then washed and LDL was added at 250 µg/ml and incubated for 8 hrs. The supernatants were removed and assayed for lipid hydroperoxides and monocyte chemotactic activity was determined as described in example 1.

Formation of Oxidized Phospholipids (POVPC, PGPC, and PEIPC) from PAPC By Addition of 13(S)-HPODE or 15(S)-HPETE or Hydrogen Peroxide.

13(S)-BPODE or 15(S)-HPETE or vehicle alone was added at various concentrations to PAPC, mixed and evaporated forming a thin film and allowed to oxidize in air. In some experiments, PAPC was evaporated forming a thin film and allowed to oxidize in air with 100 µl containing hydrogen peroxide at various concentrations. The samples were extracted with chloroform/methanol (2:1, v,v) and in the case of the hydrogen peroxide experiments by addition of 5 parts chloroform/methanol (2:1,v,v) to one part aqueous solution, mixing, and centrifugation. The chloroform phase was collected and analyzed by ESI-MS in the positive ion mode. The level of the remaining PAPC and the oxidized phospholipids that formed were determined and expressed in relation to the internal standard, 1,2-ditetradecanoyl-rac-glycerol-3-phosphocholine (DMPC, m/z 678.3).

Fast Performance Liquid Chromatography (FPLC) and Reverse Phase High Performance Liquid Chromatography (RP-HPLC).

Fast performance liquid chromatography (FPLC) and reverse phase high performance liquid chromatography (RP-BPLC) were performed as described in example 1. For the detection of cholesteryl linoleate hydroperoxide an Alltech Alltima 250×4.6 mm, 5 micron RP-HPLC C18 column was used to separate and detect cholesteryl linoleate hydroperoxide at 234 nm and cholesteryl linoleate at 205 nm. The mobile solvent consisted of acetonitrile/2-propanol/water (44:54:2, v/v/v) at 1.0 ml/min. Lipids were resuspended in the mobile solvent for injection.

Electrospray Ionization Mass Spectrometry (ESI-MS).

Electrospray ionization mass spectrometry (ESI-MS) in the positive or negative ion mode was performed according to the protocol and conditions previously described (Watson (1999) *J. Biol. Chem.* 274: 24787-24798; Watson (1997) *J. Biol. Chem.* 272: 13597-13607). ESI-MS was performed with a API III triple-quadrupole biomolecular mass analyzer (Perkin-Elmer) fitted with an articulated, pneumatically assisted nebulization probe and an atmospheric pressure ionization source (Watson (1997) *J. Biol. Chem.* 272: 13597-13607). Positive ion flow injection analysis was done with acetonitrile/water/formic acid (50/50/0.1, v/v/v) and negative ion flow injection analysis was done with methanol/water (50/50) containing 10 mM ammonium acetate. For quantitative analysis, 1,2-ditetradecanoyl-rac-glycerol-3-phosphocholine (DMPC) or heptadecanoic acid were used as internal standards. Ions were scanned at a step size of 0.3 Da. Data were processed by software provided by PE Sciex.

Other Methods.

Protein content of lipoproteins was determined by a modification (Lorenzen and Kennedy (1993) *Anal. Biochem.* 214: 346-348) of the Lowry assay (Lowry et al. (1951) *J. Biol. Chem.* 193: 265-275). Lipid hydroperoxide levels were measured using the assay described by Auerbach et al. (1992) *Anal. Biochem.* 201: 375-380. In some experiments, where indicated, the lipid in culture supernatants containing LDL that was oxidized by the artery wall cell cocultures was extracted by chloroform-methanol and hydroperoxides determined by the Auerbach method. Paraoxonase activity was measured as previously described (Gan et al. (1991) *Drug Metab. Dispos.* 19: 100-106). Statistical significance was determined by model 1 ANOVA. The analyses were carried out first using ANOVA in an EXCEL application to determine if differences existed among the group means, followed by a paired Student's t-test to identify the significantly different means, when appropriate. Significance is defined as $p<0.01$.

Results.

Example 1 demonstrated that LDL contains "seeding molecules" necessary for LDL oxidation by artery wall cells. We previously reported (Navab et al. (1991) *J. Clin. Invest.* 88: 2039-2046; Berliner et al. (1990) *J. Clin. Invest.* 85: 1260-1266) that freshly isolated LDL does not induce monocyte adherence to endothelial cells and does not induce monocyte chemotaxis while mildly oxidized LDL induces both (Id.). The ability of mildly oxidized LDL to induce monocyte adherence and chemotaxis was based on the presence in the mildly oxidized LDL of three oxidized phospholipids with characteristic m/z ratios (m/z 594,610, and 828) (Watson (1999) *J. Biol. Chem.* 274: 24787-24798; Watson (1997) *J. Biol. Chem.* 272: 13597-13607). We did not see evidence of these oxidized phospholipids in freshly isolated LDL (data not shown). Therefore, we concluded that the "seeding molecules" in freshly isolated LDL were by themselves insufficient to generate the three biologically active oxidized phospholipids either because the level of these "seeding molecules" was less than some critical threshold or because additional and different "seeding molecules" were required to generate the biologically active oxidized phospholipids. Thus, we concluded that at least one other step in the formation of mildly oxidized LDL was required beyond the initial "seeding".

Step 2.

Apo A-I (But Not apo A-II) Renders Human Artery Wall Cells Unable to Oxidize LDL.

Figure 11:
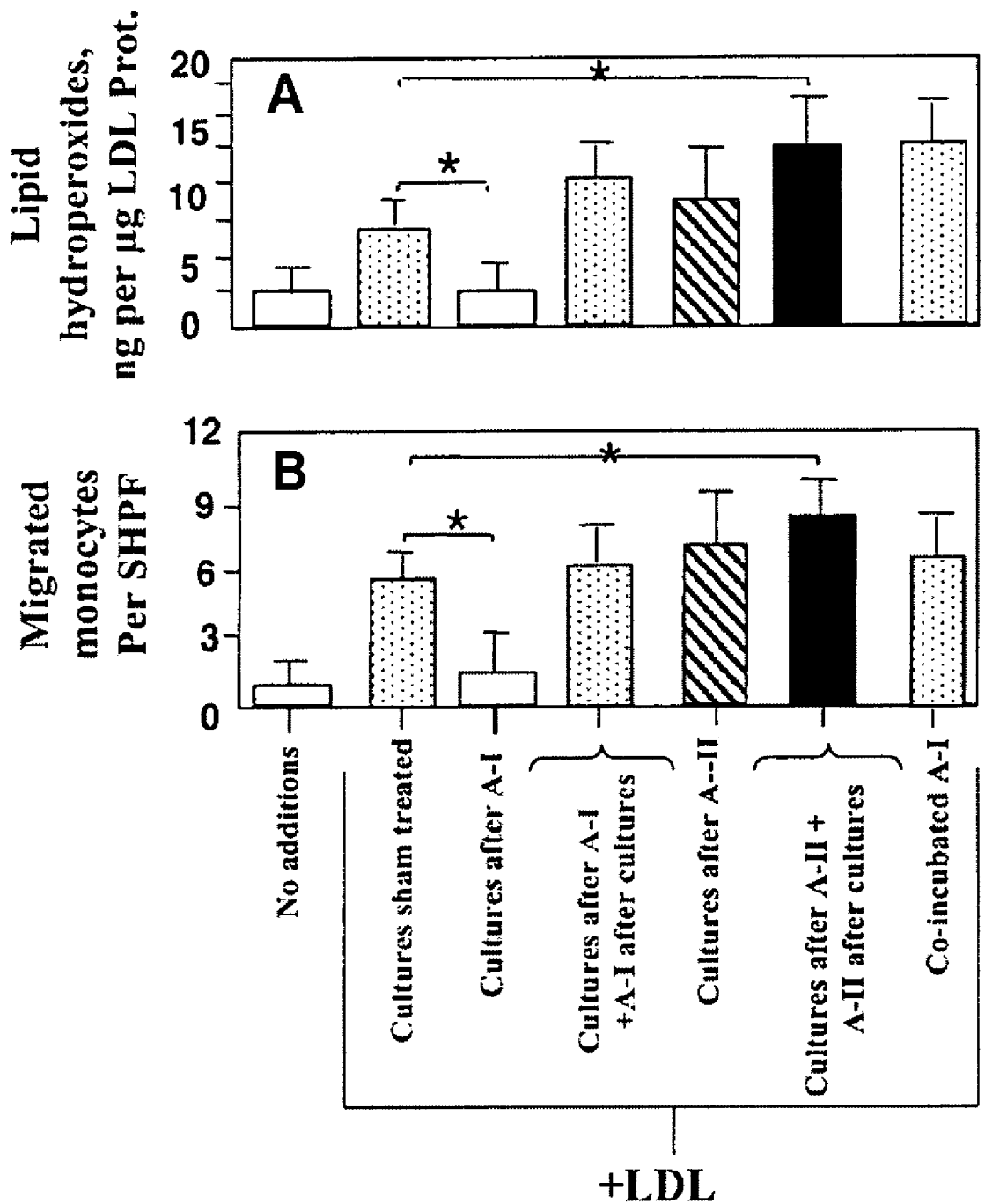
FIG. 11, panels A and B, show that Apo A-I removes substances from human artery wall cells and renders the cells unable to oxidize LDL. Cocultures were incubated with 50 µg/ml of apo A-I or apo A-II or were sham treated for 8 hrs. The conditioned media containing either apo A-I or apo A-II were removed and in some cases transferred to other cocultures that had been treated identically and served as target cocultures. LDL was added at 250 µg/ml to the target cocultures that had been sham treated (Cultures sham treated), or to target cocultures that had been treated with apo A-I which had been removed (Cultures after A-I), or treated with apo A-II which had been removed (Cultures after A-II). LDL was also added at 250 µg/ml to target cocultures that had been treated with apo A-I or apo A-II and to which was added the conditioned media containing either apo A-I or apo A-II from the first set of cocultures (Cultures after A-I+A-I after cultures), (Cultures after A-II+AII after cultures), respectively. The target cocultures were incubated for 8 hrs in M199 containing 10% LPDS and LDL with or without the additions (conditioned media) from the first set of cocultures. Some cocultures received 250 µg/ml of LDL plus 50 µg/ml of apo A-I at the start of the 8 hr incubation and this was continued for a total of 16 hrs (Co-incubated A-I). The supernatants were removed and assayed for lipid hydroperoxides (Panel A) and the cocultures were washed and fresh M199 without serum or LPDS was added and incubated for 8 hrs and assayed for monocyte chemotactic activity (Figure Panel B). Values are mean±SD from three separate experiments utilizing LDL from different donors. Asterisks indicate significance at the level of $p<0.001$.

We previously reported that co-incubation of human artery wall cells with apo A-I and LDL did not protect the LDL against oxidation by the artery wall cells (Navab et al. (1991) *J. Clin. Invest.* 88: 2039-2046). As shown in FIG. 11, these results were confirmed (compare Co-incubated A-I to sham treated cultures). However, when the human artery wall cocultures were first incubated with apo A-I and the apo A-I was then removed from the cocultures prior to the addition of LDL (Cultures after A-I), the artery wall cells were not able to oxidize the LDL (FIG. 11, panel A) and monocyte chemotaxis was prevented (FIG. 11, panel B). In contrast to the case for apo A-I, when the cultures were first incubated with apo A-II and the apo A-II then removed, the artery wall cocultures retained their ability to oxidize LDL (FIG. 11, panel A) and induce monocyte chemotaxis (FIG. 11, panel B) (cultures after A-II).

In other experiments, apo A-I was incubated with a first set of cocultures and then removed from the first set of cocultures and added to a second set of cocultures that had been identically treated (i.e. the second set of cocultures had been incubated with apo A-I which was then removed). When LDL was added to this second set of cocultures which contained apo A-I from the first set of cocultures, these reconstituted cocultures readily oxidized the LDL (FIG. 11, panel A) and induced monocyte chemotaxis (FIG. 11, panel B) (Cultures after A-I+A-I after cultures).

Similar experiments were performed with apo A-II. Apo A-II was incubated with a first set of cocultures and then removed and added to a second set of cocultures that had been identically treated (i.e. the second set of cocultures had been incubated with apo A-II which was then removed). When LDL was added to this second set of cocultures which contained apo A-II from the first set of cocultures, there was a significant increase in LDL oxidation by the artery wall cells (FIG. 11, panel A) and a significant increase in LDL-induced monocyte chemotaxis (FIG. 11, panel B) (Cocultures after A-II+A-II after cultures).

Since the reduction in LDL oxidation and LDL-induced monocyte chemotaxis by apo A-I required that the apo A-I be removed from the cocultures after incubation with the cells and before the addition of LDL (compare Cultures after A-I to Co-incubated A-I), we conclude that apo A-I removed substances from the artery wall cell cocultures that were necessary for the LDL to be oxidized by the cocultures and induce monocyte chemotaxis. We also conclude that apo A-II was incapable of reducing LDL oxidation and LDL-induced monocyte chemotaxis, and, in fact, enhanced these (compare Cultures after A-II to Cultures after A-I).

Figure 12:
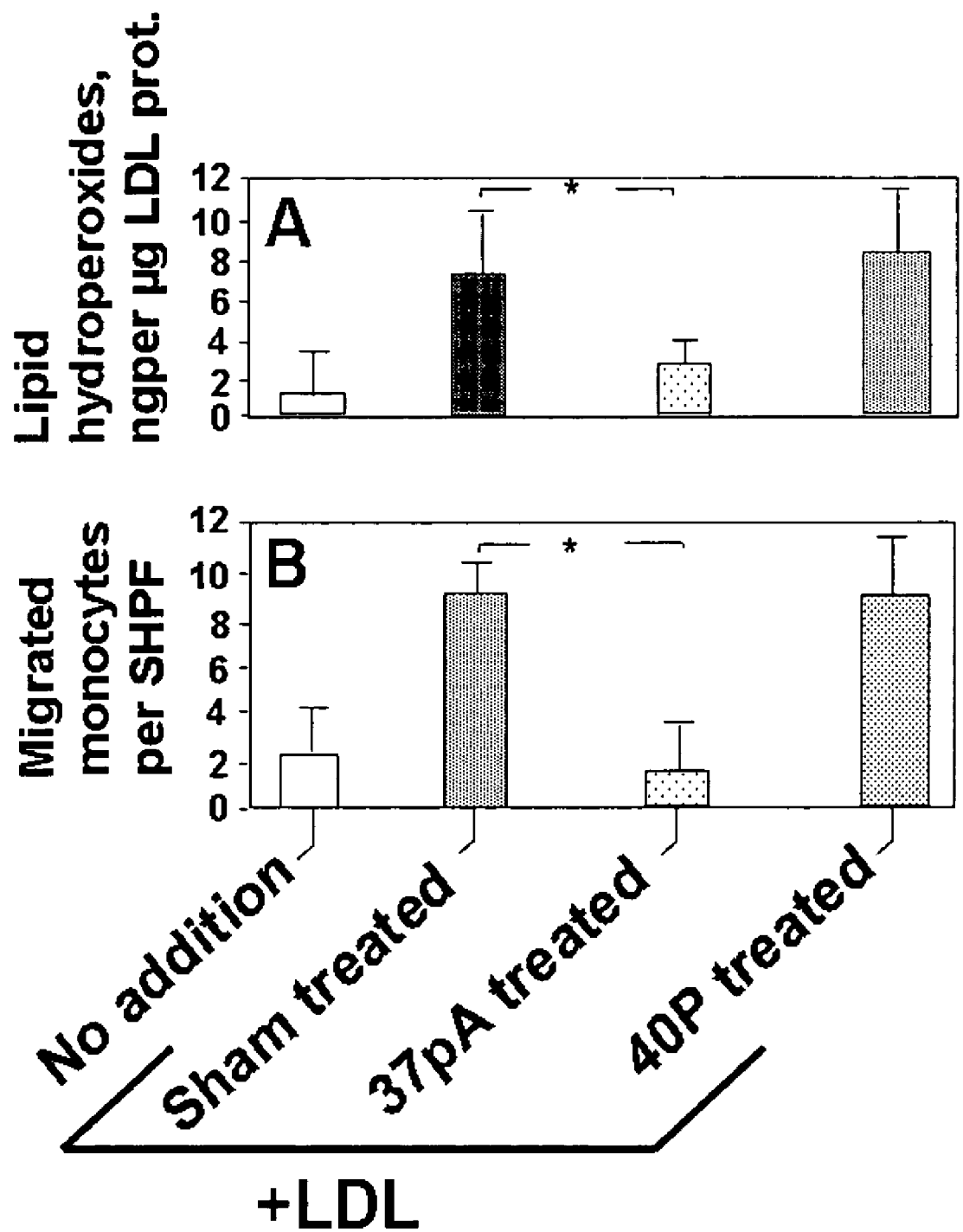
FIG. 12, panels A and B, show that an apo A-I peptide mimetic removes substances from human artery wall cells and renders the cells unable to oxidize LDL. Human aortic wall cocultures were incubated with medium alone (Sham treated), with an apo A-I mimetic peptide at 100 µg/ml (37 pA treated) or with control peptide at 100 µg/ml (40P treated) for 8 hrs. The cocultures were then washed and freshly isolated LDL was added and incubated in M199 containing 10% LPDS for an additional 8 hrs. The media were removed and assayed for lipid hydroperoxides (Panel A). The cocultures were then washed and were incubated with culture medium without serum or LPDS for an additional 8 hrs and assayed for monocyte chemotactic activity (Panel B). The data represent mean±SD of values obtained from quadruplicate cocultures in three separate experiments. Asterisks indicate significance at the level of $p=0.011$.

Similar results were obtained when the cocultures were treated with an apo A-I peptide mimetic (FIG. 12). The cocultures were incubated with or without the apo A-I peptide mimetic 37 pA, and the peptide was then removed before the addition of LDL. Other cocultures were incubated with the control peptide 40 P. Cocultures that had been incubated with the apo A-I peptide mimetic 37 pA that was removed prior to the addition of LDL were unable to oxidize the added LDL (FIG. 12, panel A) and did not induce monocyte chemotaxis (FIG. 12, panel B). This was not the case when the cocultures were treated with the control peptide 40 P. Following treatment with the control peptide 40 P, LDL was oxidized by the cocultures (FIG. 12, panel A) and induced monocyte chemotaxis (FIG. 12, panel B) to the same degree as sham treated cocultures. We conclude that the apo A-I peptide mimetic 37 pA removed substances from the artery wall cells that were necessary for LDL to be oxidized by the cocultures and induce monocyte chemotaxis.

HDL or HDL Associated Enzymes Render Human Artery Wall Cells Unable to Oxidize LDL.

We also tested whether whole HDL and its associated enzyme paraoxonase (PON) could alter the ability of artery wall cells to oxidize LDL. We incubated the artery wall cell cocultures with HDL, or purified PON and then removed these prior to the addition of LDL to the cocultures. Treatment of the artery wall cells with any of these two rendered the artery wall cells incapable of oxidizing IDL (FIG. 13, panel A) and prevented LDL-induced monocyte chemotaxis (FIG. 12, panel B). We conclude that in addition to apo A-I, HDL and PON can prevent human artery wall cells from oxidizing LDL and inducing monocyte chemotaxis.

Linoleic Acid But Not Oleic Acid Stimulates Human Artery Wall Cells to Oxidize LDL.

Figure 14:
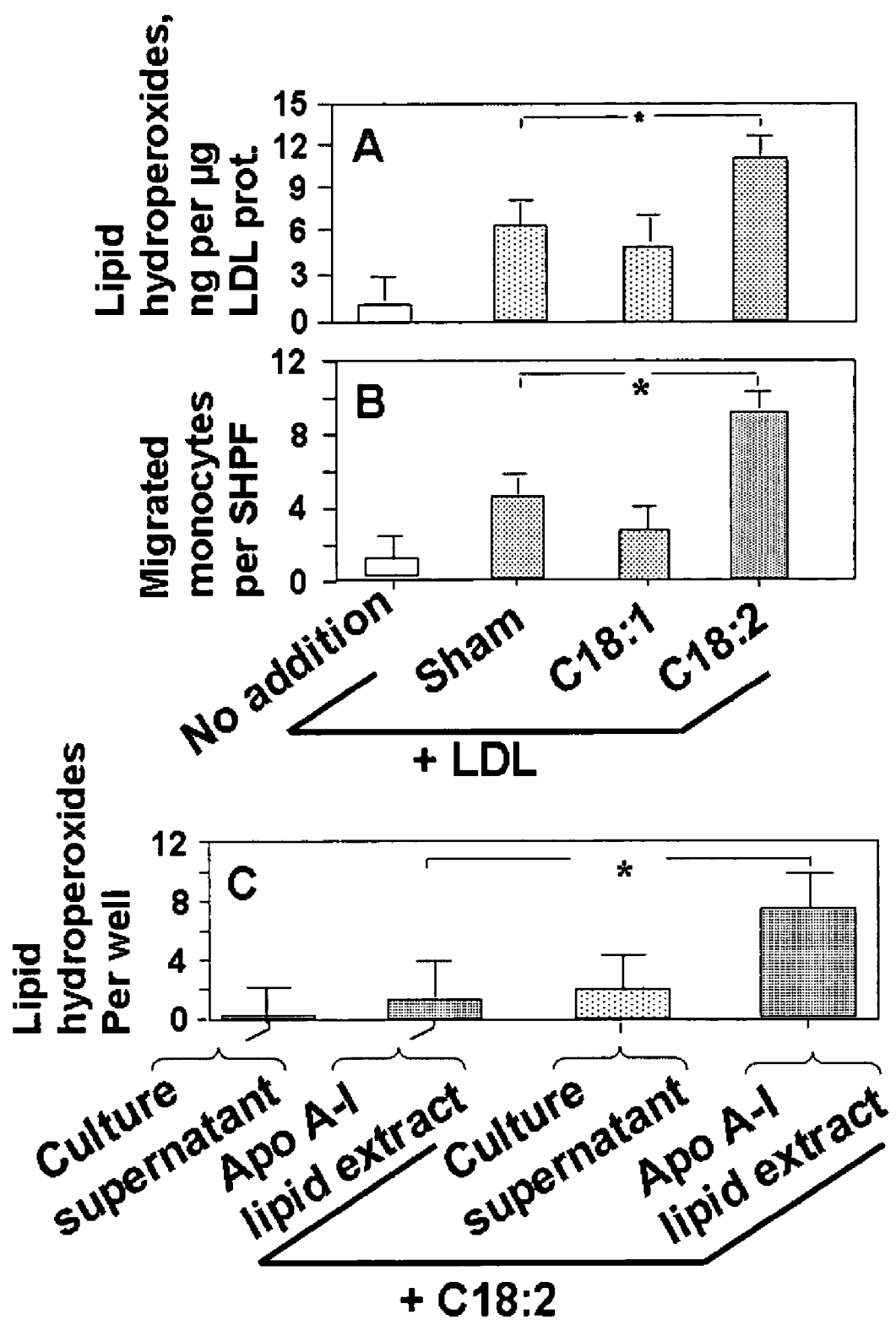
FIG. 14, panels A, B, and C, show that pretreatment of human artery wall cells with linoleic acid results in increased levels of lipid hydroperoxides, monocyte chemotactic activity and removal of 13-HPODE by apoA-I. Two sets of cocultures were incubated for 18 hours at 37° C. with 100 µM oleic acid (C18:1), or linoleic acid (C18:2) in M199 with 10% LPDS. The medium was removed and the cultures washed three times. Fresh medium without fatty acids was added and the cultures were incubated at 37° C. for an additional 3 hrs. IDL at 250 µg/ml was then added to one set of the cocultures in M199 containing 10% LPDS and incubated for 8 hrs. The medium was then removed and lipid hydroperoxides (Panel A) and monocyte chemotactic activity (Panel B) determined. To the second set of cocultures (Panel C) apo A-I was added at 100 µg/ml and incubated for three more hours with gentle mixing at 37° C. The supernatant was removed, apo A-I was separated by FPLC, and the hydroperoxide content of the lipid extract of the supernatants that did not receive apo A-I (Culture supernatant) and the lipid extract from apo A-I (Apo A-I lipid extract) were determined as described in Methods which are expressed as ng per well. Values are mean±SD of triplicate determinations. The asterisks denote $p<0.001$.

As noted above, we concluded that the "seeding molecules" in mildly oxidized LDL were by themselves insufficient to generate the three biologically active oxidized phospholipids that induce monocyte chemotaxis. We hypothesized that this might be because the level of these "seeding molecules" was less than some critical threshold or because additional and different "seeding molecules" were required to generate the biologically active oxidized phospholipids in ILDL. We reasoned that if there was some threshold for the same "seeding molecules" to generate the oxidized phospholipids and hence monocyte chemotaxis and if these "seeding molecules" were in part derived from the metabolism of linoleic acid, then enriching the human artery wall cocultures with linoleic acid might be expected to enhance their ability to oxidize LDL and induce monocyte chemotaxis. Consequently, we incubated human artery wall cocultures with or without linoleic acid (C18:2), or oleic acid (C18:1), washed the cells, and allowed them to metabolize the fatty acids by incubating them for 3 hours at 37° C. in fresh medium that was not supplemented with the fatty acids. Subsequently, we tested the ability of these human artery wall cell cocultures to oxidize ILDL and induce monocyte chemotaxis (FIG. 14, panels A-C). Incubating the artery wall cells with linoleic acid significantly enhanced the ability of the artery wall cells to oxidize ILDL compared to oleic acid (FIG. 4A) and induce monocyte chemotaxis (FIG. 14, panel B). In other experiments cocultures were incubated without LDL but with (+) or without (−) linoleic acid (C18:2) and the cells were washed and then incubated with or without apo A-I (FIG. 14, panel C). The supernatants were removed and the apo A-I separated by FPLC, and the lipid extracted from the apo A-I. Lipid extracts of the culture supernatants from incubations without apo A-I were also obtained. Incubating the cocultures with linoleic acid dramatically increased the 13-HPODE equivalents in the lipid extract of the apo A-I (FIG. 14, panel C) (compare Apo A-I lipid extract of the cells incubated with C18:2 to Apo A-I lipid extract of the cells incubated without C18:2). We conclude that incubating human artery wall cells with linoleic acid markedly enhances the cellular production of lipid hydroperoxides, i.e.13-HPODE equivalents which can be removed by apo A-I. We further conclude that incubation of human artery wall cells with linoleic acid but not oleic acid stimulates the oxidation of LDL by artery wall cells and stimulates LDL-induced monocyte chemotaxis. In other experiments, the studies described in FIG. 14, panels A-C were performed with arachidonic acid. The results indicated that arachidonic acid was even more potent than linoleic acid in stimulating the oxidation of LDL by artery wall cells (data not shown).

Further Evidence for the Role of Lipoxygenase Pathways.

Jackson and Parthasarathy suggested a role for lipoxygenase (LO) in the "seeding" of LDL (Thomas and Jackson (1991) *J. Pharmacol. Exp. Therap*. 256: 1182-1188; Parthasarathy (1994). *Modified Lipoproteins in the Pathogenesis of Atherosclerosis*. Austin, Tex.; R.G. Landes Co. pp. 91-119) and Sigari and colleagues demonstrated that fibroblasts over expressing 15-LO more readily oxidized LDL than fibroblasts transfected with vector alone (Sigari et al. (1997) *Arterioscler. Thromb. Vascul. Biol*. 17: 3639-3645). To further establish the ability of apo A-I to remove lipid hydroperoxide products of the LO pathway from cells, we incubated fibroblasts over expressing LO and cells that were transfected with vector alone with apo A-I or without apo A-I as described above. The supernatants were removed, the apo A-I was separated by FPLC, and the lipid was extracted from the apo A-I. Lipid extracts of the culture supernatants from incubations without apo A-I were also obtained. Without addition of apo A-I the lipid extracts of the supernatants from cells over expressing LO contained only slightly more 13-HPODE equivalents compared to the control cells (data not shown). In contrast, the lipid extracts of apo A-I incubated with the cells over expressing LO contained markedly more 13-HPODE equivalents (5.1-fold more) than the lipid extracts of apo A-I incubated with the control cells (data not shown).

Preincubation of the cocultures with the lipoxygenase/cyclooxygenase inhibitor ETYA ($1 \times 10^{-8}$ mol/L) prior to the addition of LDL as described in Methods resulted in an 80±7% reduction in lipid hydroperoxide levels and a 75±10% decrease in LDL-induced monocyte chemotactic activity (p<0.008, data not shown). Preincubation of human artery wall cocultures with the lipoxygenase inhibitor CDC ($1 \times 10^{-8}$ mol/L) prior to the addition of LDL as described in Methods resulted in a 73±6% reduction in lipid hydroperoxide levels and a 74±11% decrease in LDL-induced monocyte chemotactic activity (p<0.01, data not shown).

Taken together, these experiments suggest that artery wall cells produce reactive oxygen species, including those derived from the metabolism of linoleic and arachidonic acids, that are critical to the oxidation of "seeded" LDL. These experiments also suggest that HDL, apo A-I and PON, can remove or destroy these substances and render the artery wall cells incapable of oxidizing the "seeded" LDL. Our hypothesis also proposes that when a critical level in LDL is reached by the further addition of reactive oxygen species by the artery wall cells to "seeded" LDL, the non-enzymatic oxidation of a major LDL phospholipid, PAPC, results in the formation of three biologically active oxidized phospholipids (POVPC, PGPC, and PEIPC) that induce monocyte binding and chemotaxis.

Step 3.

13(S)-HPODE and 15(S)-HPETE Markedly Enhance the Oxidation of PAPC and Cholesteryl Linoleate.

Figure 15:
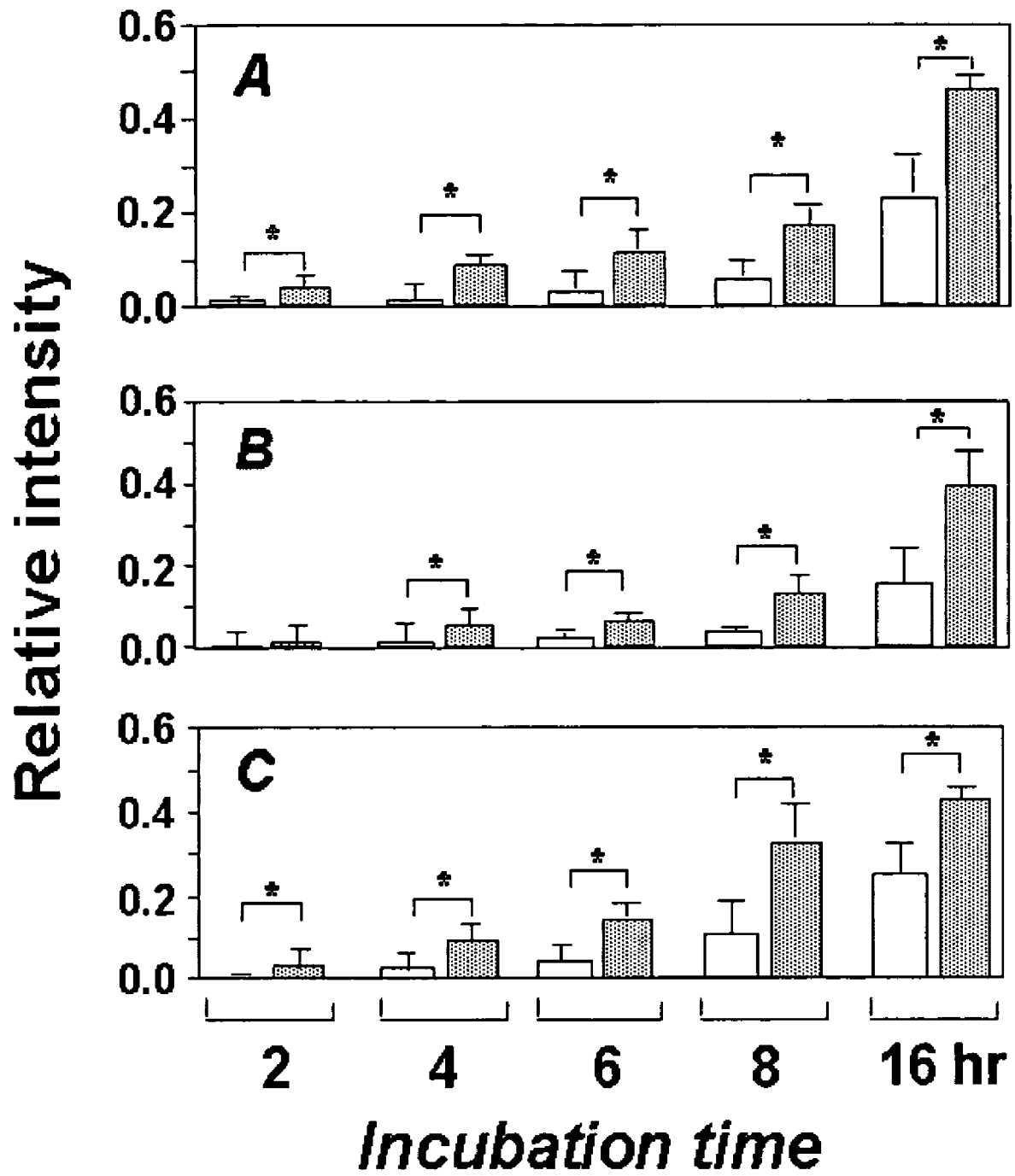
FIG. 15, panels A, B, and C, show that 13(S)-HPODE accelerates the formation of bioactive oxidized phospholipids from PAPC. Ten µg of PAPC with 1.0 µg of 13(S)-HPODE (stippled bars) or with vehicle alone (open bars) were mixed and evaporated forming a thin film and allowed to oxidize in air for the times shown. Following extraction with chloroform-methanol, the samples were analyzed by ESI-MS in the positive ion mode. The data represent the levels of 1-palmitoyl-2-oxovaleryl-sn-glycero-3-phosphocholine (POVPC, m/z 594, panel A), 1-palmitoyl-2-glutaryl-sn-glycero-3-phosphocholine (PGPC, m/z 610, panel B), and 1-palmitoyl-2-(5,6-epoxyisoprostane $E_2$)-sn-glycero-3-phosphocholine (PEIPC, m/z 828, panel C) relative to an internal standard (0.1 µg DMPC) that was added with the PAPC. The values are the mean±SD of triplicate samples. The asterisks indicate $p<0.01$. 13(S)-HPODE alone did not give a signal for m/z 594, 610 or 828 (data not shown).

We previously reported that if PAPC were exposed to air for 48 hours it would undergo auto-oxidation to produce the three biologically active phospholipids POVPC, PGPC, and PEIPC) (Watson (1999) *J. Biol. Chem*. 274: 24787-24798; Watson (1997) *J. Biol. Chem*. 272: 13597-13607). If products of the lipoxygenase pathway were involved in both the initial "seeding" of circulating LDL and the further "seeding" of LDL by artery wall cells necessary to reach a critical threshold that would cause the non-enzymatic oxidation of PAPC, then the addition of the products of the lipoxygenase pathway to PAPC should significantly increase the formation of the three biologically active oxidized phospholipids (POVPC, PGPC, and PEIPC). To test this hypothesis we measured the formation of the three biologically active oxidized phospholipids from PAPC as a function of time. As shown in FIG. 15, panels A-C the addition of 1.0 µg of 13(S)-HPODE to 10 µg of PAPC enhanced the formation of the three biologically active oxidized phospholipids at each time point sampled (POVPC, m/z 594, FIG. 15, panel A; PGPC, m/z 610, FIG. 15, panel B; PEIPC, m/z 828, FIG. 15, panel C).

Figure 16:
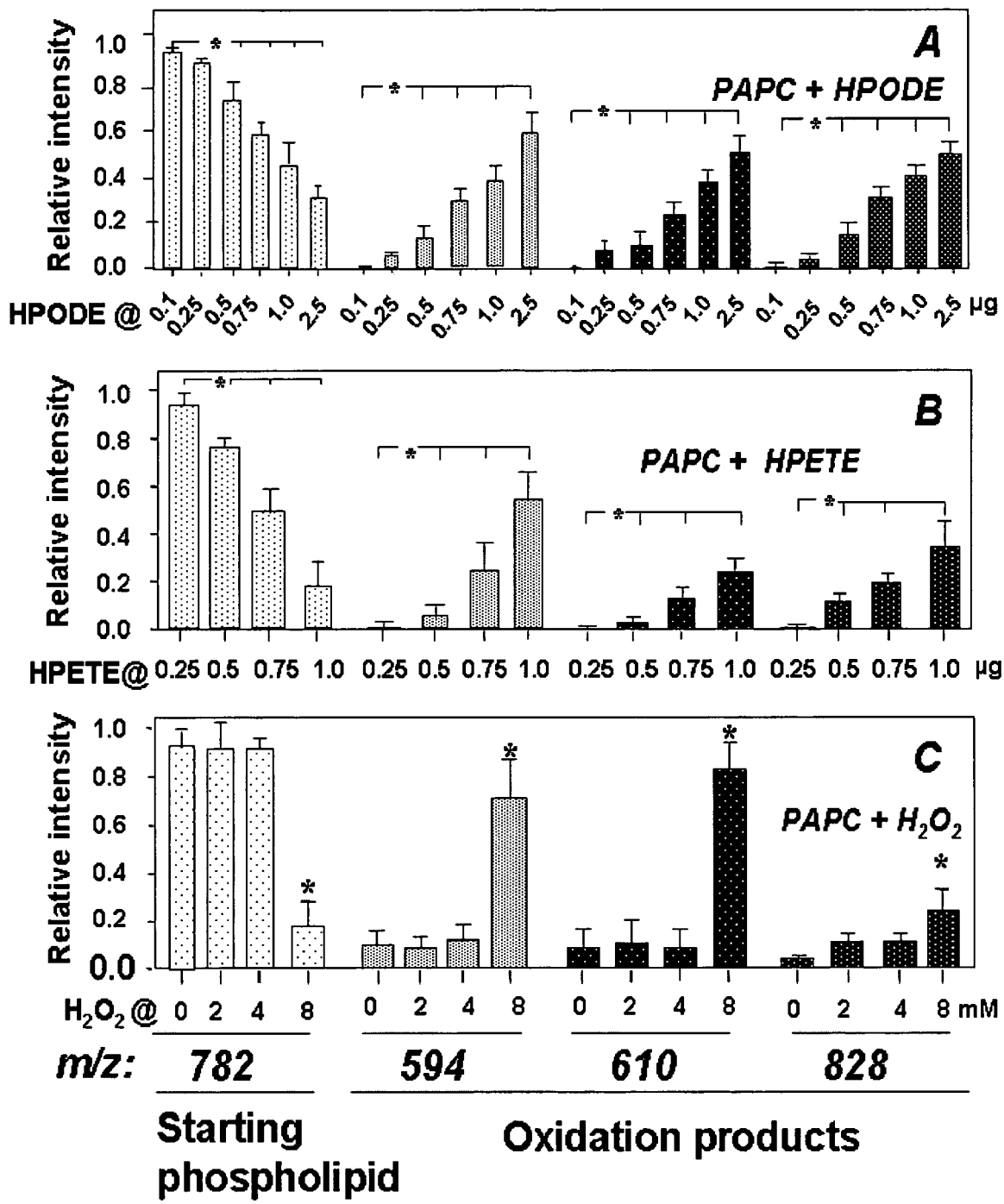
FIG. 16, panels A, B, and C, show that 13(S)-HPODE, 15(S) HPETE or $H_2O_2$ accelerate in a dose dependant manner the formation of oxidized phospholipids from PAPC. Ten µg of PAPC was mixed with the indicated micrograms of 13(S)-HPODE (Panel A), or 15(S)-HPETE (Panel B) and evaporated forming a thin film and allowed to oxidize in air for 8 hrs. In Panel C, ten µg of PAPC was evaporated forming a thin film and $H_2O_2$ was added at the indicated concentrations and allowed to oxidize for 8 hrs. Following extraction with chloroform-methanol, the samples were analyzed by ESI-MS in the positive ion mode. The data represent the levels of PAPC, m/z 782; POVPC, m/z 594; PGPC, m/z 610; and PEIPC, m/z 828 relative to an internal standard (0.1 µg DMPC) that was added with the PAPC. The values are the mean±SD of triplicate samples. 13(S)-HPODE alone, 15(S)-HPETE alone or $H_2O_2$ did not give a signal for m/z 594, 610 or 828 (data not shown). Asterisks indicate significant differences at $p<0.001$.

The data in FIG. 16, panel A, demonstrate that addition of as little as 0.5 µg of 13(S)-BPODE to 10 µg of PAPC for 8 hours significantly decreased the relative abundance of PAPC (m/z 782) and significantly increased the formation of the three biologically active oxidized phospholipids (m/z 594, 610, and 828). FIG. 16, panel B, demonstrates that addition of as little as 0.5 µg of 15(S)-HPETE to 10 µg of PAPC for 8 hours significantly decreased the relative abundance of PAPC (m/z 782) and significantly increased the formation of the three biologically active oxidized phospholipids (m/z 594, 610, and 828).

FIG. 16, panel C, shows that 8 mM hydrogen peroxide added to 10 µg PAPC for 8 hours dramatically decreased the relative abundance of PAPC and increased the formation of the biologically active phospholipids, while 2 mM and 4 mM hydrogen peroxide had no effect. Since the molecular weight of PAPC is 782 the molar ratio required for the enhanced oxidation of PAPC by hydrogen peroxide was approximately 62:1 ($H_2O_2$: PAPC) in the experiment described in FIG. 16, panel C. Since the molecular weight of 13(S)-HPODE is 311 and the molecular weight of 15(S)-HPETE is 336.5, the molar ratio at which these products of the lipoxygenase pathway promoted the oxidation of PAPC is approximately 1:8. Thus, on a molar basis the ability of 13(S)-HPODE and 15(S)-HPETE to oxidize PAPC was more than two orders of magnitude greater than that of hydrogen peroxide under these conditions. Taken together these data indicate that 13(S)-HPODE and 15(S)-HPETE, products of linoleic and arachidonic acid metabolism, respectively, act as potent oxidizing agents and promote the non-catalytic oxidation of PAPC to yield the three biologically active oxidized phospholipids found in mildly oxidized LDL.

Figure 17:
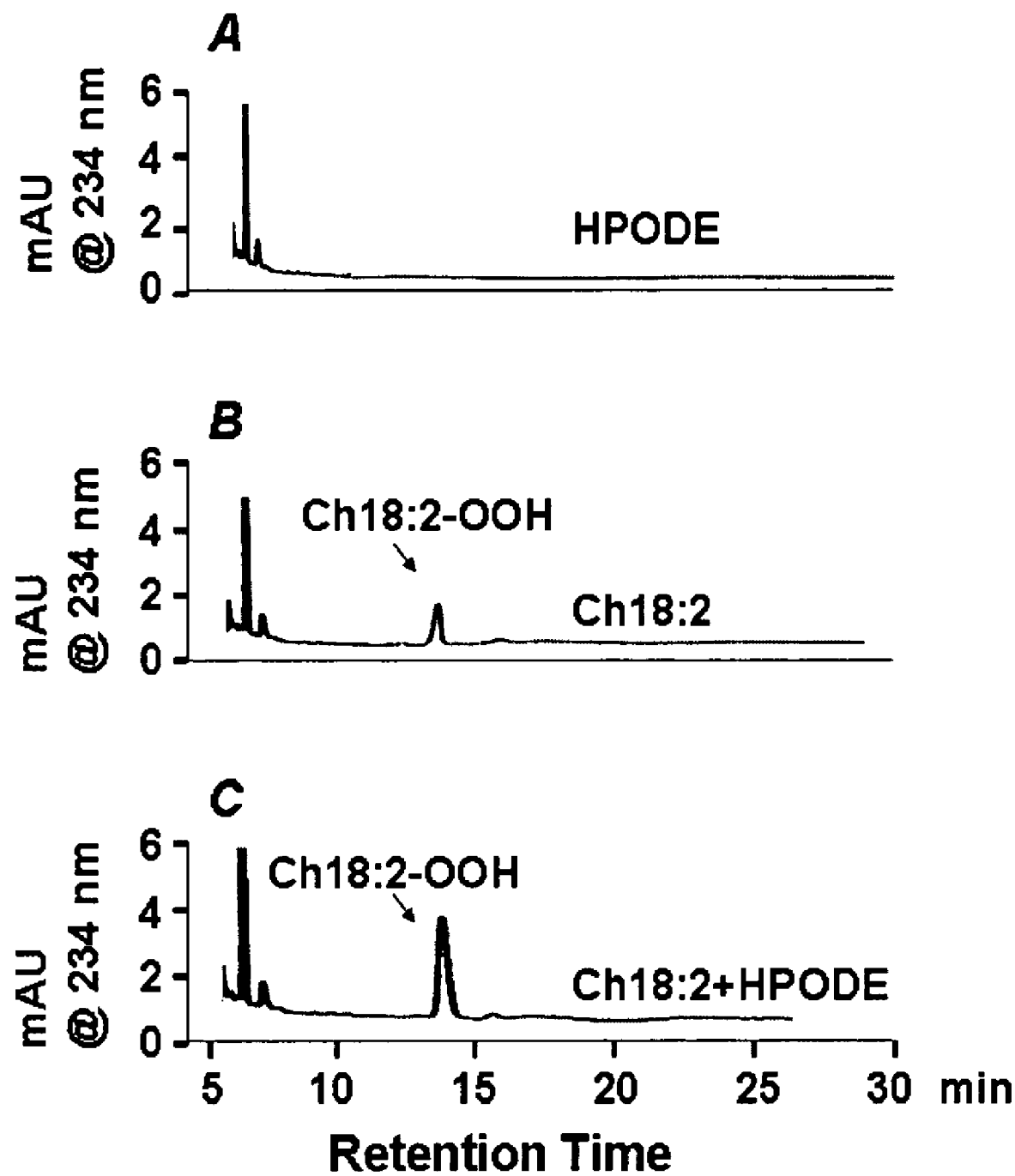
FIG. 17, panels A, B, and C, show that 13(S)-BPODE stimulates the non-enzymatic formation of cholesteryl linoleate hydroperoxide (Ch18:2-OOH). 13(S)-BPODE 0.5 µg/ml (Panel A) or cholesteryl linoleate 10 µg/ml (Panel B) or cholesteryl linoleate 10 µg/ml together with 13(S) HPODE 0.5 µg/ml (Panel C) in chloroform/methanol (2:1, v/v) containing 0.01% BHT was briefly swirled to mix and evaporated to dryness under argon and allowed to undergo air oxidation in a laminar flow hood for 6 hrs. The lipids were solubilized in 50 µl of chloroform and analyzed for the presence of cholesteryl linoleate hydroperoxide (Ch18:2-OOH) by RP-HPLC as described herein.

Stocker and colleagues (Neuzil et al. (1998) *Biochem*. 37: 9203-9210; Upston et al. (1997) *J. Biol. Chem*. 272: 30067-30074) presented indirect evidence to suggest that the lipoxygenase mediated oxidation of cholesteryl linoleate is mediated primarily by a non-enzymatic process that involves products of the lipoxygenase pathway. The experiments in FIG. 17 demonstrate that the presence of 13(S)-HPODE markedly stimulated the non-enzymatic formation of cholesteryl linoleate hydroperoxide (Ch18:2-OOH).

Paraoxonase Destroys the Biologic Activity of the Three Oxidized Phospholipids, m/z 594, 610, and 828.

Figure 18:
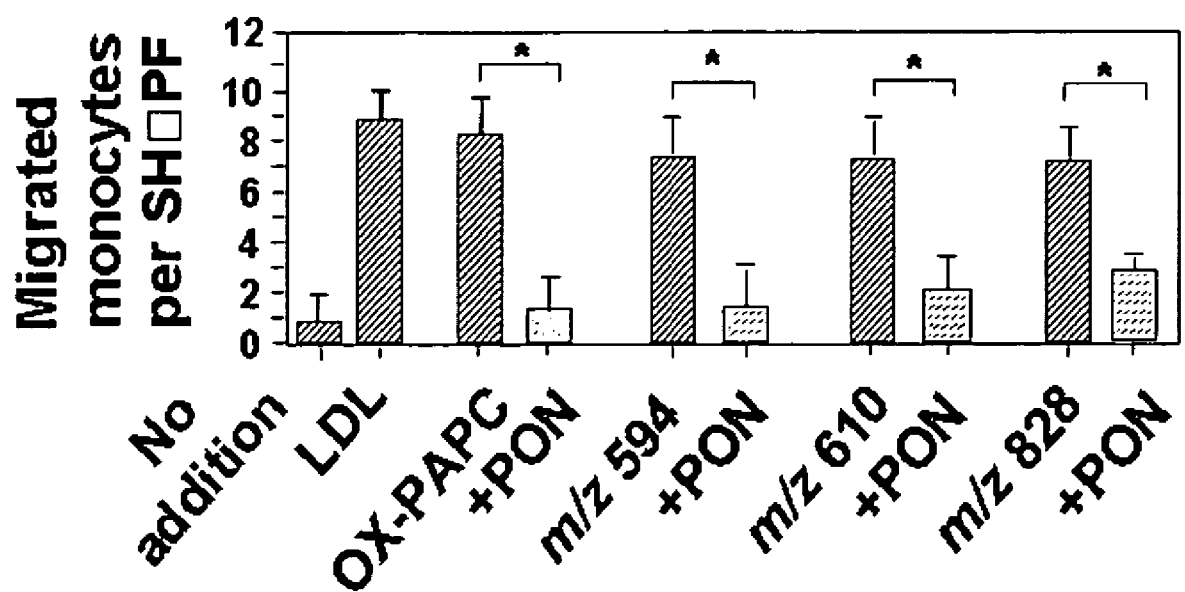
FIG. 18 shows that purified paraoxonase destroys the bioactivity of the oxidized phospholipids. Oxidized PAPC, (Ox-PAPC), POVPC (m/z 594), PGPC (m/z 610) or PEIPC (m/z 828) were incubated in test tubes in M199 without, or with $1\times10^{-2}$ U/ml purified human paraoxonase (+PON) for 3 hrs with gentle mixing at 37° C. Paraoxonase was removed from the mixture and the lipids were incubated with human aortic wall cocultures in M199 with 10% LPDS for 8 hrs at 37° C. The cocultures were then washed and incubated with fresh media without serum or LPDS for an additional 8 hrs at 37° C. The supernatants were removed and analyzed for monocyte chemotactic activity. Data are mean±SD for quadruplicate cocultures. Asterisks indicate significant differences at the level $p<0.0001$.

We previously reported that antioxidants and HDL could prevent the formation of biologically active mildly oxidized LDL, but once formed HDL and antioxidants could not decrease the biologic activity of the mildly oxidized LDL (Navab et al. (1991) *J. Clin. Invest*. 88: 2039-2046). In these experiments in contrast to those reported above where HDL was incubated with the cocultures before the LDL was added to the cocultures, we previously had added the HDL together with LDL to the cocultures. In other studies, we reported that PAF-AH (Watson et al. (1995) *J. Clin. Invest*. 95: 774-782), and PON (Watson et al. (1995) *J. Clin. Invest*. 96: 2882-2891) could destroy the biologic activity of mildly oxidized LDL if the enzymes were incubated with the LDL before addition to the cells. These studies were performed with mildly oxidized LDL, not the specific oxidized phospholipids (i.e. oxidized PAPC or POVPC, PGPC, PEIPC). To directly test the ability of paraoxonase to destroy the biologic activity of each of the three oxidized phospholipids we incubated oxidized PAPC (Ox-PAPC), or POVPC, m/z 594; PGPC, m/z 610; or PEIPC, n/z 828 with or without purified paraoxonase as described in Methods. The enzyme was separated from the mixtures and the compounds were added to human artery wall cocultures. Incubation of Ox-PAPC, or POVPC, m/z 594; PGPC, n/z 610; or PEIPC, m/z 828 with purified paraoxonase followed by separation of the paraoxonase from the compounds prior to presentation to the artery wall cell cocultures resulted in the destruction of the biologic activity of each, i.e. the loss of the ability to induce monocyte chemotactic activity (FIG. 18). Two mutant recombinant PON preparations, a generous gift of Drs. Robert Sorenson and Bert N. La Du (Sorenson et al. (1995) *Proc. Natl. Acad. Sci*. USA 92: 7187-7191) were unable to inactivate the biologically active phospholipids in this assay system (data not shown). PON that was inactivated by boiling at 100° C. had no effect on the activity of the oxidized phospholipids (data not shown).

HDL from Patients with Coronary Artery Disease, With Normal Blood Lipid Levels, Who Were Neither Diabetic Nor on Hypolipidemic Medications, Failed to Prevent LDL Oxidation by Artery Wall Cells and Failed to Destroy the Biologic Activity of Oxidized PAPC.

Figure 19:
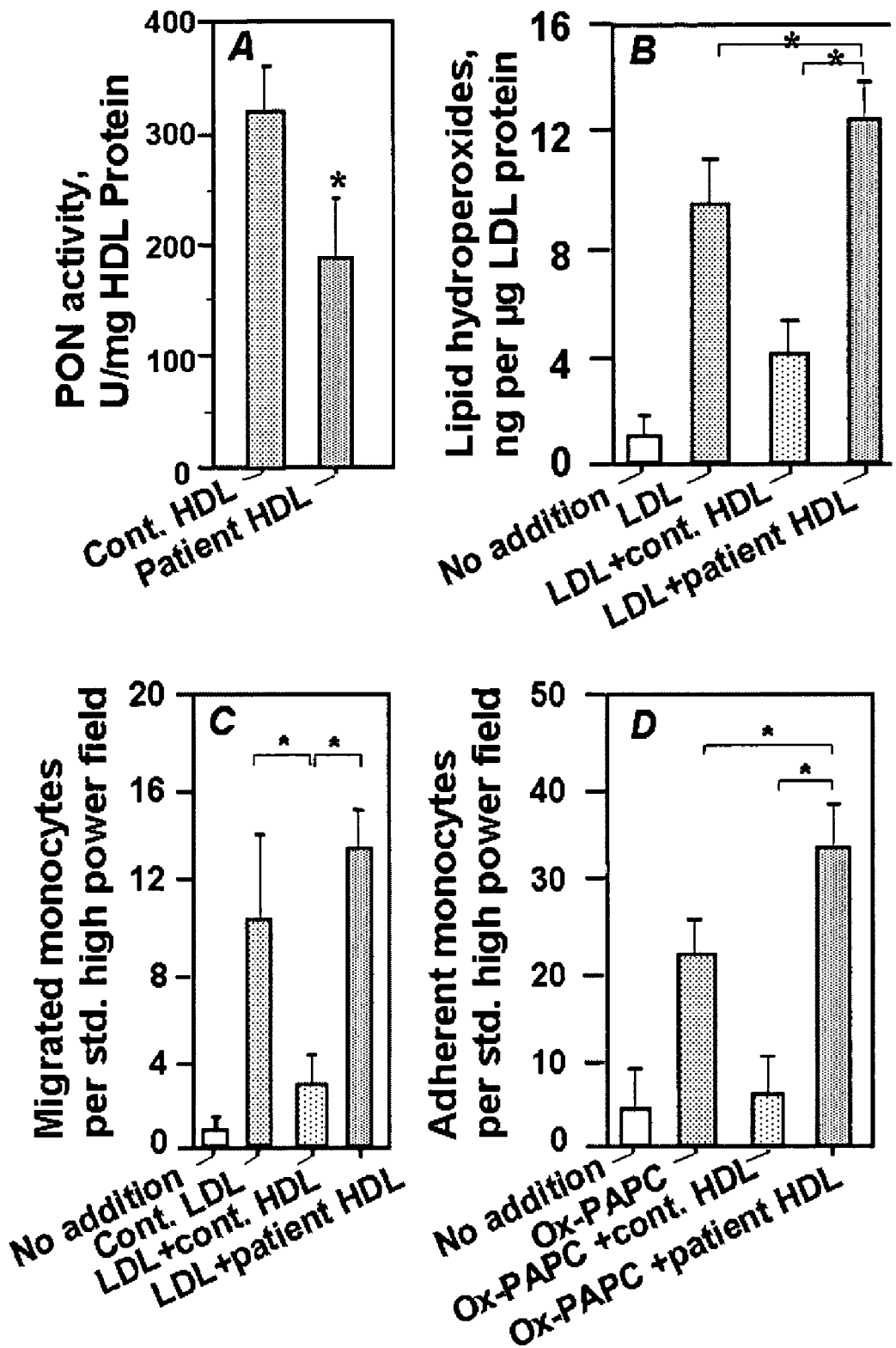
FIG. 19, panels A, B, C, and D, show that HDL from patients with angiographically documented coronary atherosclerosis despite normal IHDL-cholesterol levels that is deficient in paraoxonase activity, does not protect LDL from oxidation by artery wall cells, and does not destroy the biologic activity of oxidized phospholipids. These patients had angiographically documented coronary atherosclerosis, despite normal total cholesterol, triglycerides, LDL-cholesterol and HDL-cholesterol levels. The patients were not diabetic nor on hypolipidemic medications. Paraoxonase activity was determined as described in Methods for 24 patients and 29 age and sex matched normal subjects (Panel A). Data from 14 previously reported patients and from 19 previously reported normal subjects are included in panel A together with data from an additional 10 patients and age and sex matched normal subjects. The ability of HDL from the additional 10 patients and controls to protect a control LDL against oxidation by artery wall cells is shown in Panel B as determined by lipid hydroperoxide formation as described herein and in Panel C by monocyte chemotactic activity which was determined as described herein. The data in panel C includes data previously reported for 5 patients and 4 normal subjects together with data from the additional 10 patients and their age and sex matched normal subjects. The data in Panel D represent a new approach, namely the ability of patient and normal HDL (n=10 for each group) to inhibit the biologic activity of oxidized PAPC (Ox-PAPC). In each instance 100 µg/ml of Ox-PAPC was incubated with 250 µg/ml of HDL in test tubes in 10% LPDS in M199 at 37° C. with gentle mixing for 4 hrs. The HDL-Ox-PAPC mixture was then added to endothelial monolayers and monocyte binding determined. Data are the mean±SD of quadruplicate cocultures and the asterisk indicates a significant difference at the level of $p<0.01$ for Panel A; $p<0.001$ for LDL vs LDL+patient HDL, $p<0.0001$ for LDL+cont. HDL vs LDL+patient HDL in Panel B; $p<0.009$ for control LDL vs LDL+Control HDL, $p<0.000008$ for LDL+Control HDL vs LDL+Patient HDL in Panel C; $p<0.009$ for Ox-PAPC vs Ox-PAPC +Patient HDL, $p<0.0001$ for Ox-PAPC +Control HDL vs Ox-PAPC+Patient HDL in Panel D.

We reported (Navab et al. (1997) *J. Clin. Invest*. 99: 2005-2019) that after screening more than 250 patients with angiographically documented coronary artery disease, we identified 14 patients with angiographically documented coronary artery disease despite normal blood lipid levels and the absence of diabetes. These 14 had on average lower levels of paraoxonase activity despite their normal HDL-cholesterol levels compared to 19 age and sex matched controls (Id.). However, the differences between the patient's paraoxonase activity and normal controls did not reach statistical significance (Id). We have now identified another 10 patients with normal lipid levels (i.e. total cholesterol <200 mg/dl, LDL-cholesterol <130 mg/dl, HDL-cholesterol >45 mg/dl for males and >50 mg/dl for females, and triglycerides <150 mg/dl) who had angiographically documented coronary artery disease, who were neither diabetic nor on hypolipidemic medications. Combining the previously reported data with the new data we now see a statistically significant difference in paraoxonase activity between patients (n=24) and controls (n=29) (FIG. 19, panel A).

Previously we were only able to obtain sufficient sample from 5 of the original 14 patients to test in our coculture system (Navab et al. (1997) *J. Clin. Invest*. 99: 2005-2019). We reported that HDL from these five did not protect against LDL-induced monocyte chemotactic activity in the human artery wall coculture system, while HDL from 4 control subjects did. In our current studies we obtained HDL from an additional 10 normolipidemic patients with angiographically documented coronary artery disease, who were neither diabetic nor on hypolipidemic medications. The ability of HDL from these ten patients and ten age and sex matched normal subjects to modify the oxidation of a control LDL (i.e. LDL obtained from one normal subject which was used in all of the experiments) is shown in FIG. 19, panel B. As shown in FIG. 19, panel B, HDL taken from 10 out of 10 of the patients did not protect the control LDL against oxidation by human artery wall cells. Indeed, on average the patient HDL actually increased control LDL oxidation, while HDL from 10 out of 10 age and sex matched normal subjects markedly reduced control LDL oxidation by the artery wall cells.

Adding the data on monocyte chemotaxis from the ten new patients and ten normal subjects to that of the previously reported 5 patients and four age and sex matched normal subjects yields a total of 15 patients and 14 normal subjects that have now been studied in the coculture system. In the experiments shown in FIG. 19, panel C, HDL from 15 out of 15 of these patients was unable to protect against LDL- induced monocyte chemotactic activity, while 14 out 14 of the controls had HDL which did.

Previously, we had not directly tested the ability of HDL from this subset of patients to destroy the biologic activity of oxidized PAPC. FIG. 19, panel D demonstrates that the patients (none previously reported) had HDL which could not inhibit the biologic activity of oxidized PAPC (10 out of 10 patients had HDL which did not inhibit the biologic activity of oxidized PAPC). Indeed, the HDL of the 10 patients on average increased the Ox-PAPC-induced monocyte adherence to HAEC (FIG. 19, panel D). In contrast, HDL from 10 out of 10 age and sex matched normal subjects markedly decreased the ability of Ox-PAPC to induce monocyte adherence to HAEC (FIG. 19, panel D). Taken together these data indicate that HDL from this subset of patients with coronary artery disease appears defective despite their normal plasma HDL-cholesterol levels.

Discussion.

Figure 13:
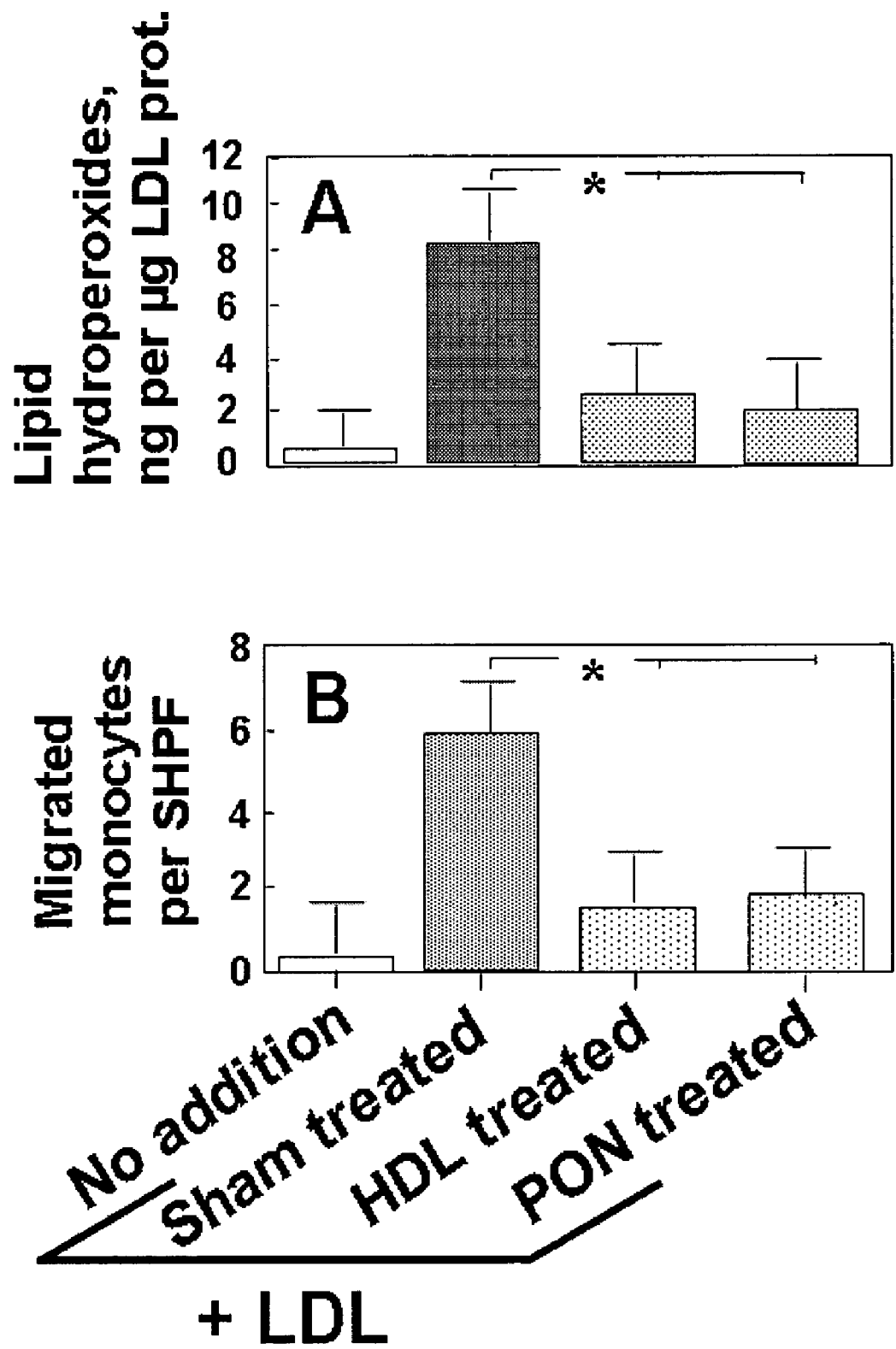
FIG. 13, panels A and B, show that HDL and its associated enzyme PON render human artery wall cells unable to oxidize LDL. Human aortic wall cocultures were incubated with medium alone (Sham treated), with HDL at 350 µg/ml (HDL treated), or with purified paraoxonase at $1\times10\times^{-2}$ U/ml (PON treated) for 8 hrs. The cocultures were then washed and freshly isolated LDL was added at 250 µg/ml and incubated in M199 containing 10% LPDS for an additional 8 hrs. The media were collected and analyzed for lipid hydroperoxides (Panel A). The cocultures were then washed and were incubated with culture medium without serum or LPDS for 8 hrs and the supernatant was collected and analyzed for monocyte chemotactic activity (Panel B). The data represent mean±SD of values obtained from quadruplicate cocultures in three separate experiments. Asterisks indicate significance at the level of $p<0.011$.

We have demonstrated in this example that apo A-I and an apo A-I mimetic were able to act directly on human artery wall cells and profoundly influence their ability to oxidize LDL (FIGS. 11 and 12). In contrast, apo A-II was unable to prevent human artery wall cells from oxidizing LDL (FIG. 11). Similar to the case for LDL (see example 1), treating human artery wall cells with HDL or PON rendered the artery wall cells incapable of oxidizing LDL (FIG. 13). These experiments indicate that HDL and its associated enzymes can inhibit human artery wall cells from contributing the additional reactive oxygen species necessary for circulating LDL to reach the critical threshold required to oxidize PAPC to the biologically active phospholipids.

The data in this example support a role for products of the lipoxygenase pathways in artery wall cells in the second step of the formation of mildly oxidized LDL and are consistent with the recent findings of Cyrus et al. that disruption of the 12/15-lipoxygenase gene diminished atherosclerosis in apoE-deficient mice (Cyrus et al. (1999) *J. Clin. Invest*. 103: 1597-1604). They concluded that several mechanisms could explain their findings but favored one in which ". . . lipoxygenase-derived hydroperoxides or secondary reactive lipid species may be transferred across the cell membrane to 'seed' the extracellular LDL, which would then be more susceptible to a variety of mechanisms that could promote lipid peroxidation."

The non-enzymatic oxidation of PAPC to form the three biologically active phospholipids (POVPC, PGPC, and PEIPC) was greatly enhanced by 13-HPODE and 15-HPETE (FIGS. 15 and 16). Indeed, the ability of 13-HPODE and 15-HPETE to oxidize PAPC to these three biologically active phospholipids was more than two orders of magnitude more potent than that of hydrogen peroxide (FIG. 16). These results are consistent with the findings of Montgomery, Nathan and Cohn (Montgomery et al. (1986) *Proc. Natl. Acad. Sci.* USA 83: 6631-6635) who found that the amount of hydrogen peroxide necessary to produce oxidation of LDL was two orders of magnitude greater than that produced by endothelial cells that oxidized LDL. The ability of 13-HPODE to stimulate the nonenzymatic formation of cholesteryl linoleate hydroperoxide (Ch18:2-OOH) (FIG. 17') is consistent with the results of Stocker and colleagues (Neuzil et al. (1998) *Biochem*. 37: 9203-9210; Upston et al. (1997) *J. Biol. Chem*. 272: 30067-30074) and suggests that products of the lipoxygenase pathway may be central in the formation of a variety of oxidized lipids as hypothesized by Cyrus et al. (1999) *J. Clin. Invest*. 103: 1597-1604.

Stocker and colleagues (Garner et al. (1998) *J. Biol. Chem*. 273: 6080-6087; Garner et al. (1998) *J. Biol. Chem*. 273: 6088-6095) also demonstrated that both apo A-I and apo A-II can reduce cholesteryl ester hydroperoxides via a mechanism that involves oxidation of specific methionine residues (Garner et al. (1998) *J. Biol. Chem*. 273: 6088-6095). In our experiments only apo A-I and not apo A-II was able to reduce the oxidation of LDL after injection into mice (see example 1). Moreover, only apo A-I and not apo A-II was able to decrease the ability of human artery wall cells to oxidize LDL (FIG. 11).

The destruction of the biologic activity of Ox-PAPC and its components (POVPC, PGPC, and PEIPC) by PON (FIG. 18) and by normal HDL but not by HDL from patients with angiographically proven atherosclerosis despite normal plasma HDL-cholesterol levels (FIG. 19), suggests that an abnormality in HDL may be responsible, at least in part, for the atherosclerosis in this relatively rare subset of patients. A role for PON in the pathogenesis of atherosclerosis was first suggested by the work of Mackness and Durrington (Mackness et al. (1998) *FEBS Let*. 423: 57-60; Ayub et al. (1999) *Arterioscler. Thromb. Vascul. Biol*. 19: 330-335) and has been supported by the work of a number of laboratories including ours (Shih et al. (1996) *J. Clin. Invest*. 97: 1630-1639; Shih et al. (1998) *Nature* 394: 284-287; Castellani et al. (1997) *J. Clin. Invest*. 100: 464-474). We report in this example that normolipidemic patients with coronary artery disease who were neither diabetic nor on hypolipidemic medications had significantly lower levels of PON activity compared to age and sex matched normal subjects (FIG. 19, panel A). However, there was overlap in PON activities of the patients and normal subjects. In contrast, HDL from 10 out of 10 patients failed to protect control LDL against oxidation by human artery wall cells (FIG. 19, panel B) and failed to inhibit the biologic activity of oxidized PAPC (FIG. 19, panel D) while HDL from 10 out of 10 age and sex matched normal subjects did. These findings suggest to us that the difference in patient and control HDL can not be completely explained by differences in PON activity.

Figure 20:
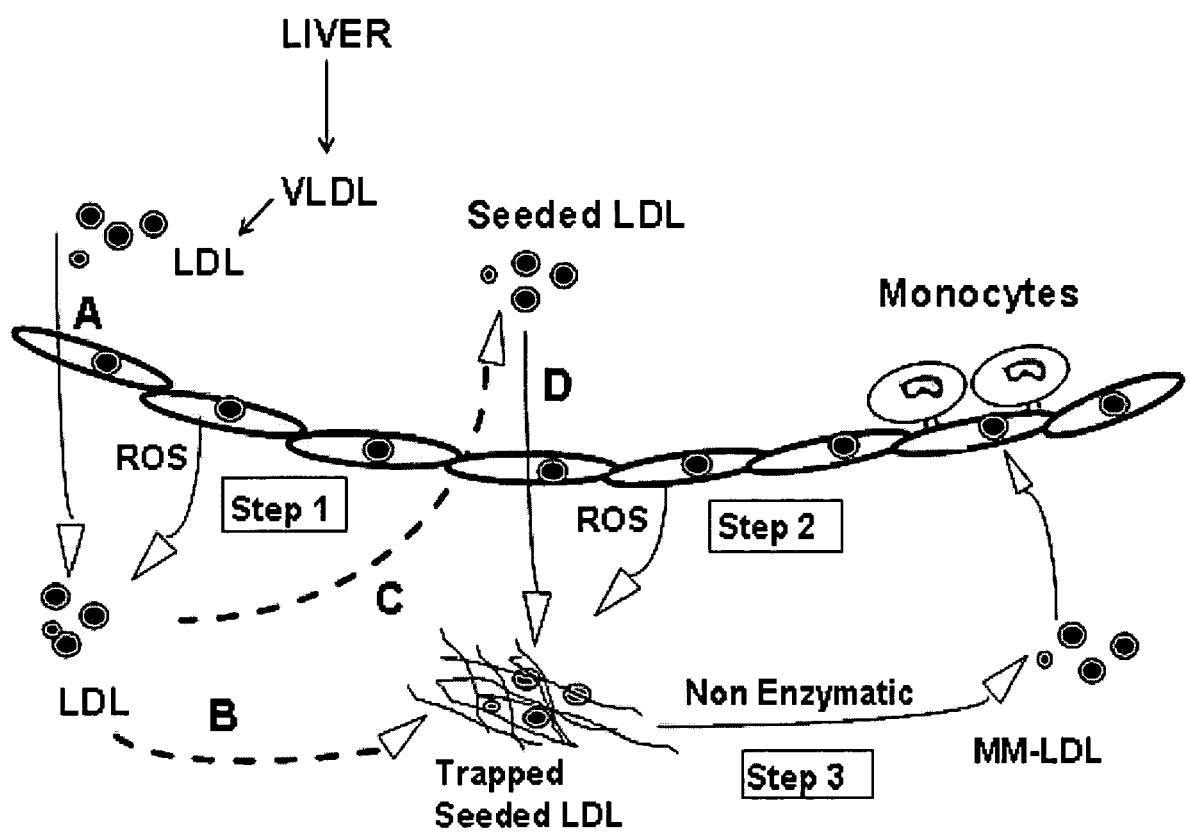
FIG. 20 illustrates a three step model for LDL oxidation by artery wall cells: Step1—LDL is seeded. Step 2—LDL is trapped in the artery wall and receives further seeding molecules. Step 3—When a critical level of seeding molecules relative to phospholipids is reached in the LDL, a non-enzymatic oxidation process generates POVPC, PGPC, and PEIPC. LDL that is formed from the hydrolysis of VLDL in the circulation may contain "seeding molecules". Alternatively, LDL may enter the subendothelial space (A), where it is seeded with reactive oxygen species (ROS) delivered from the artery wall cells (STEP 1). While the cartoon depicts this as occurring in the subendothelial space, STEP 1 might actually occur in the microcirculation. If the LDL is seeded in the subendothelial space it might remain there becoming trapped in the extracellular matrix (B) or the seeded LDL could exit into the circulation (C) and re-enter the subendothelial space at another site where it would become trapped in the extracellular matrix (D). In STEP 2 the artery wall cells generate and transfer additional or different ROS to the trapped seeded LDL. This transfer could occur within the cell, at the cell surface, or in an adjacent protected microdomain. Following this transfer of reactive oxygen species to the seeded and trapped LDL, a non-enzymatic propagation of lipid oxidation occurs (STEP 3). This results in the formation of specific oxidized phospholipids that induce NF-κB activation, monocyte binding, MCP-1 production, and M-CSF production and which are present in mildly oxidized LDL (minimally modified LDL; MM-LDL). As indicated, normal HDL is capable of blocking each and every step in the formation of MM-LDL.

The data presented in this example and in example 1 and in example 1 demonstrate a role for HDL and its components, apo A-I, and PON in regulating each and every step in a three step process that leads to the formation of mildly oxidized LDL and which is diagrammed in FIG. 20. Understanding the mechanisms for the formation of mildly oxidized LDL and the role of HDL and its components in preventing the formation and inhibiting the biologic activity of mildly oxidized LDL may lead to new therapeutic strategies for the prevention and treatment of atherosclerosis and the clinical syndromes that result from this inflammatory process.

Example 3

Cell-free Assay to Determine Inflammatory Properties of HDL

The inflammatory properties of HDL play a significant role in the development of atherosclerosis. We developed a new cell free assay (CFA) to distinguish the inflammatory properties of HDL. This new assay is a modified version of a CFA we previously reported (Navab et al. 2001; *J Lipid Res*. 42:1308-1317) based on the ability of HDL to inactivate oxidized phospholipids in LDL.

HDL was isolated from plasma or serum by Magnetic Bead Reagent (Polymedco). A standard mixture of LDL (90.0 μg/mL) and oxidized PAPC (62.5 μg/mL) were incubated (30 min) and the oxidation of the mixture was measured in the presence of DCFH-DA (dichlorofluorescein diacetate) that generates a fluorescent signal (485/530 nm) when oxidized. HDL was tested for its ability to inhibit the fluorescent signal, which in turn is a measure of HDL's ability to inactivate oxidized phospholipids in LDL.

Figure 21:
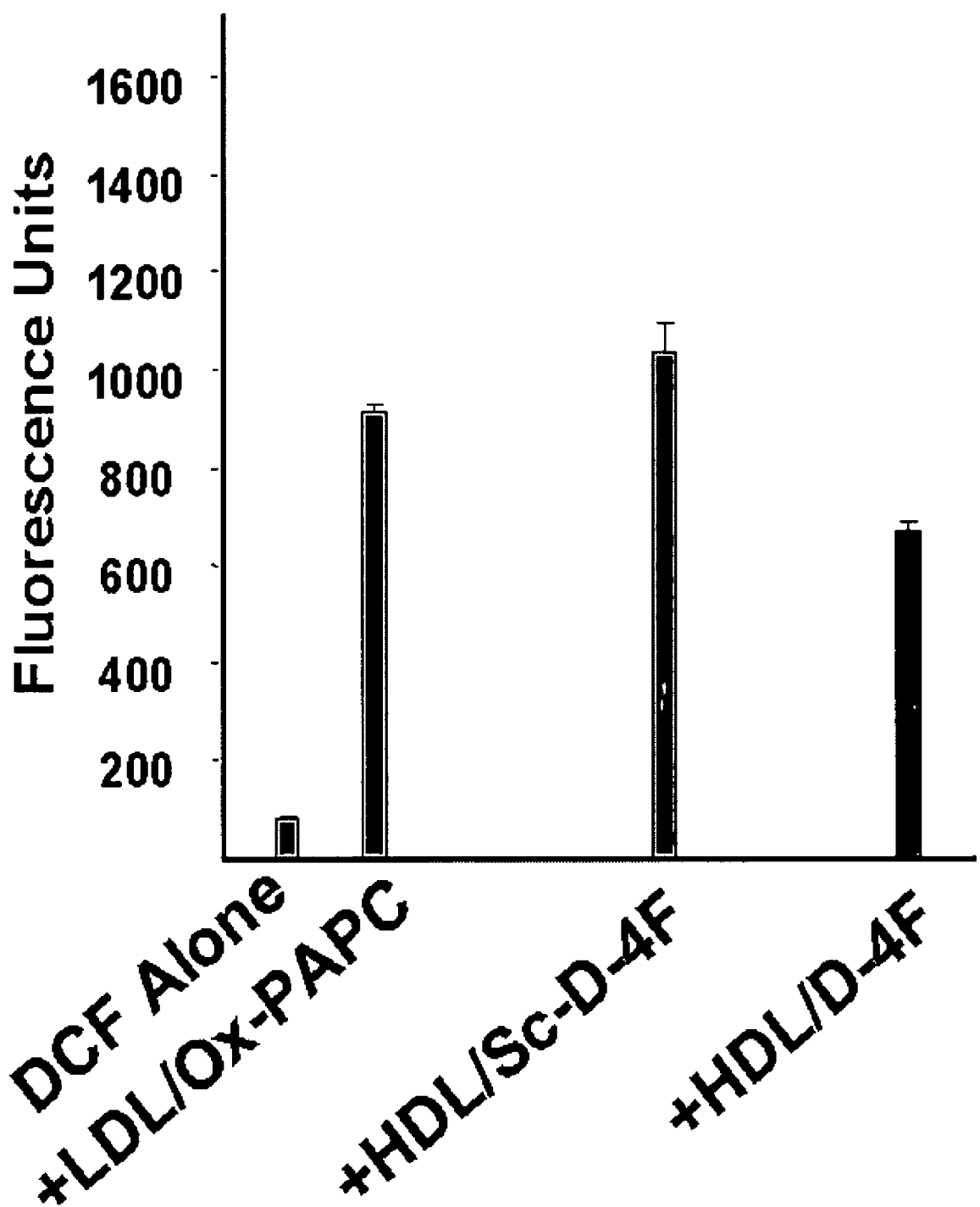
FIG. 21. D-4F or scrambled D-4F (Sc D-4F) at 100 µg/mL was added to the drinking water of apoE null mice (n=3 for each group) overnight. In the morning the mice were bled and their HDL isolated using Magnetic Bead Reagent (Polymedco) and 5 µg of mouse HDL-cholesterol was tested in the cell-free assay. The results clearly show improvement in HDL function after administration of D-4F.
Figure 22:
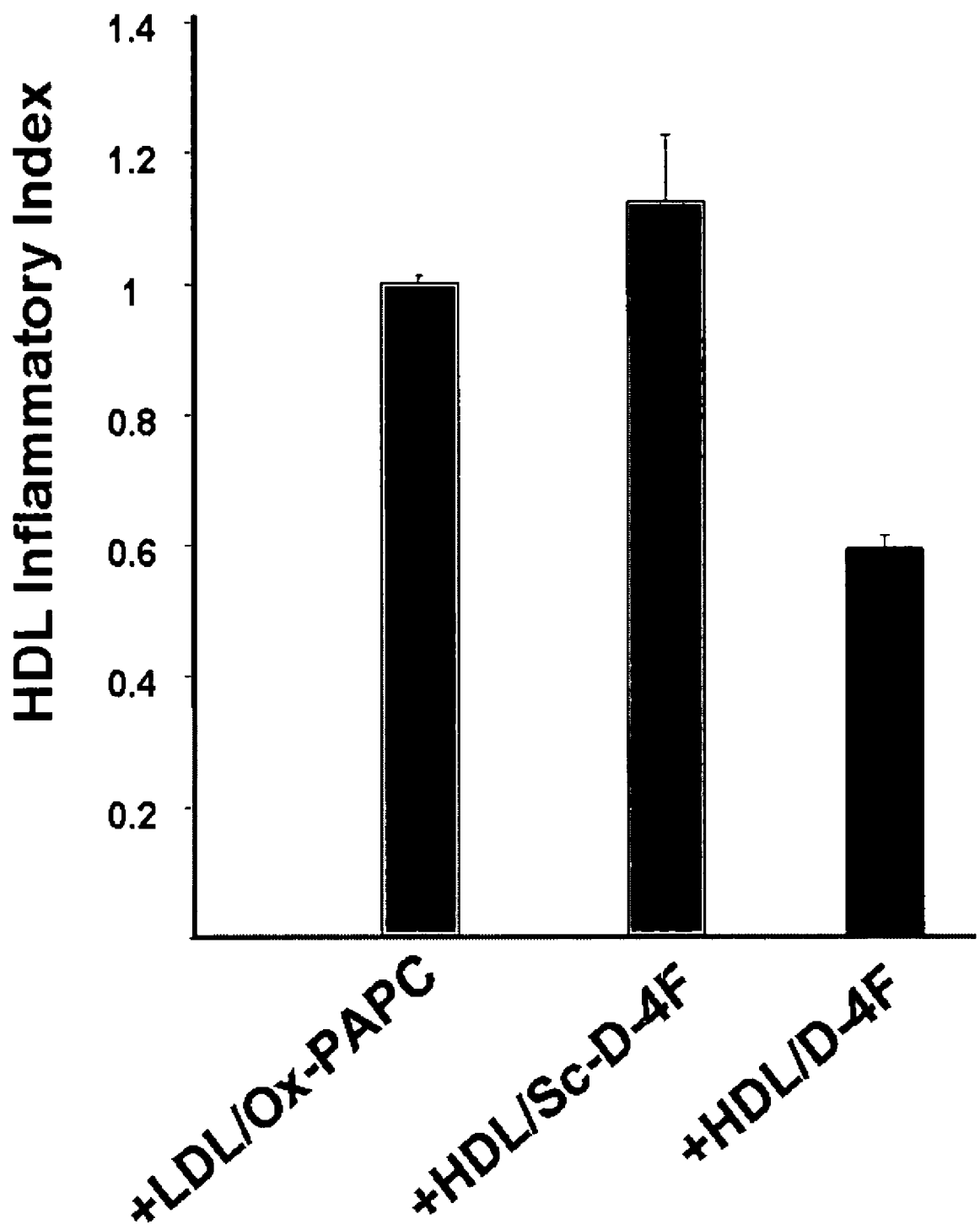
FIG. 22. The data in the FIG. 21 were normalized so that the fluorescence from LDL-Ox-PAPC alone was set at a value of 1.0. The other samples were then normalized to this value. The results show how these data can be used to construct an HDL-inflammatory index. Values less than 1.0 represent anti-inflammatory HDL; values>1.0 represent pro-inflammatory HDL.
Figure 23:
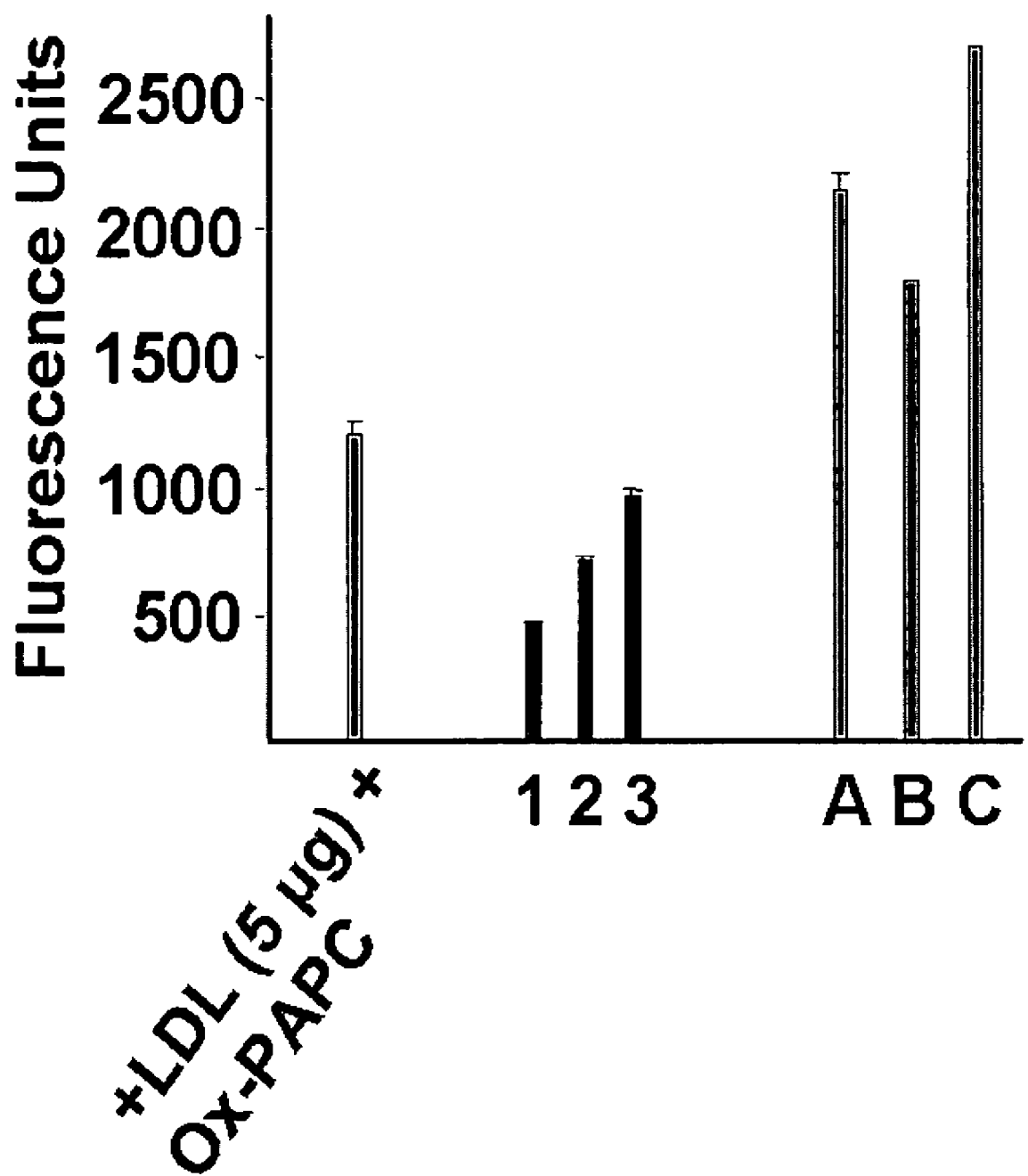
FIG. 23. Three subjects with anti-inflammatory HDL (subjects 1, 2, and 3) were compared to three subjects with pro-inflammatory HDL (subjects A, B, and C) in the cell-free assay. Five micrograms of HDL-cholesterol isolated using Magnetic Bead Reagent (Polymedco) from each subject was added to the LDL+Ox-PAPC in this assay.
Figure 24:
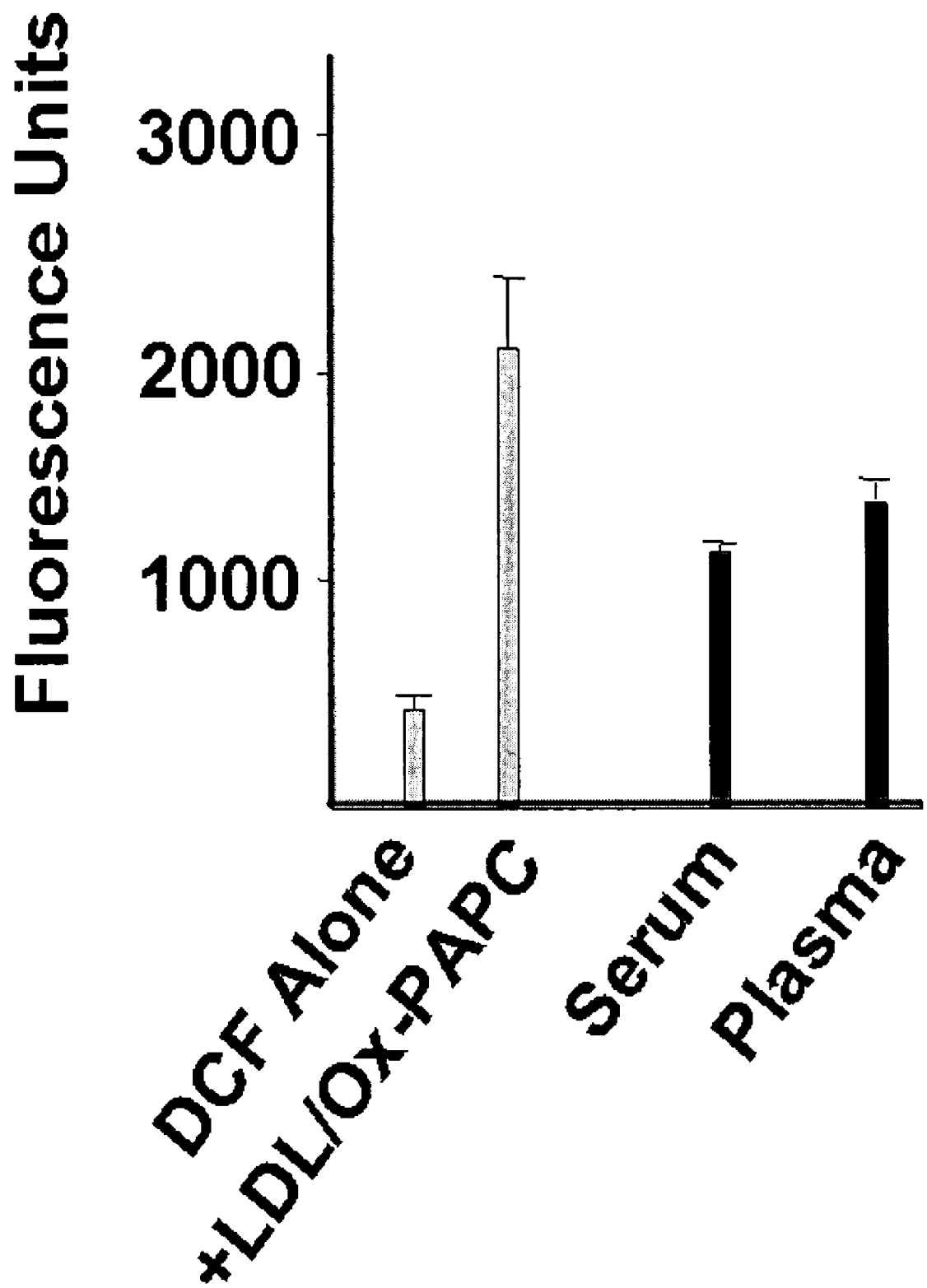
FIG. 24. HDL was isolated using Magnetic Bead Reagent (Polymedco) from serum or plasma from a single normal individual and tested in the cell-free assay. Five micrograms of HDL-cholesterol was added to the cell-free assay after being isolated from either serum or plasma. The results were indistinguishable with HDL isolated from either serum or plasma.

Using this new method, we were able to accurately distinguish the inflammatory properties of HDL, i) from mouse models of atherosclerosis, ii) from animal models of atherosclerosis in which an anti-atherogenic peptide, D-4F (an ApoAI mimetic peptide) was administered, iii) from monkeys that were administered D-4F, and iv) from known proinflammatory and anti-inflammatory human samples (see, e.g., FIGS. 21, 22, and 23). Moreover, the new CFA was equally effective on HDL prepared from both serum and plasma samples (see, e.g., FIG. 24).

HDL function has become the target for therapeutic interventions of cardiovascular diseases. We have developed a simple, rapid, versatile, and effective CFA to determine the inflammatory properties of HDL in serum samples, which can be used as a biomarker for drug efficacy.

Example 4

Protocols for a Cell-Free Assay

Materials:

Table 1 lists sources for basic materials for a cell-free assay according to the present invention.

Table 1. Reagents for use in one embodiment of a cell-free assay for "protective" HDL.

| Materials | Vendor | Catalog Number |
|---|---|---|
| 1 DCF (2',7'-dichlorodihydro-fluorescein diacetate, H2DCFDA | Molecular probes | D - 399 |
| 2 Low-density-lipoprotein (LDL) | Biomedical Tech. | BT - 903 |
| 3 Methanol (Drisolv) | EM Science | MX0472 -6 |
| 4 10× Dulbecco's phosphate buffered saline (PBS) | Gibco | 14200 - 075 |
| 5 Sodium azide | Sigma | S - 8032 |
| 6 Screw cap glass tubes | Fisher | |
| 7 Corning polypropylene, round bottom, black microplate | Fisher | 07 - 200 - 762 |
| 8 Vortex mixer | Fisher | |
| 9 Rotator/nutator | | |
| 10 Fluorescence plate reader (e.g., Spectra Max Gemini XS) | Molecular Devices | |
| 11 Uniplate (96 wells, 2 mL, polypropylene, round bottom) | Whatman | 7701 - 5200 |
| 12 PAPC | | |
| 13 HDL Magnetic Bead Reagent | Polymedco | 5030 |
| 14 Cholesterol Assay using cholesterol standard and cholesterol reagents | Thermo DNA | |

Methods:

Preparation of PBS Buffer 1×

Dilute the PBS 10× to 1× using double distilled water. Then add 0.2 g/L sodium azide. Adjust the pH to 7.4. Filter the solution (0.22 μ filter) and aliquot into, e.g., 50 ml centrifuge tubes. This buffer can be stored at 4° C.

Preparation of Stock Solution of DCF

Prepare a stock solution of 2.0 mg/mL DCF in methanol. Vortex for 2 minutes until it completely dissolves. Keep at room temperature for 20 minutes. Prepare aliquots of 500 μL in polypropylene tubes. Briefly blow argon gas onto the liquid to prevent further oxidation. Wrap parafilm around the lid and store at −80° C.

Preparation of Ox-PAPC

Add 5 mg of PAPC (for 100 mg PAPC, 20 glass tubes). Dry down the PAPC in chloroform with argon using a Pasteur glass pipette. (Note: PAPC should be generously spread along the walls of the tubes). Put tubes in hood for 48 hrs to air oxidize. After air exposure, add 0.5 ml $CHCl_3$ to tube and vortex vigorously. Repeat step 4 for all tubes. Pool the $CHCl_3$ from all tubes. Analyze by mass spectrometry to confirm oxidation. Make a stock solution of 10 mg/ml Ox-PAPC in Chloroform, aliquot and store at −80° C. protected from light.

Preparation of Stock Solution of Ox-PAPC

From the stock solution of Ox-PAPC (10 mg/ml Ox-PAPC in Chloroform), take appropriate amount needed for the experiment in a glass tube and dry down using Argon gas. Vortex for 5 sec. Resuspend in 1XPBS just before use.

HDL Isolation with Magnetic Bead Reagent

Separate plasma or serum from a blood sample using green top tube or serum separator tube by centrifuging at 5° C. at 2300 rpm for 20 minutes. Remove the supernatant (serum or plasma). Add ⅕ by volume of the magnetic bead reagent to each sample and mix by vortexing. Centrifuge at 5° C. at 12,000 rpm for 10 minutes. Remove supernatant (HDL). Using the cholesterol assay (see materials), measure the amount of HDL and prepare a stock at a concentration of 200 μg/ml.

LDL+ox-PAPC Pre-incubation.

Prepare LDL at 180 μg/mL using PBS. Prepare Ox-PAPC at 125 μg/mL using PBS. Make a 1:1 solution of LDL and Ox-PAPC. The final concentration should be 90 μg of LDL+62.5 μg of Ox-PAPC/ml. Incubate the mixture for 30 minutes at 37° C.

HDL+LDL+ox-PAPC Pre-incubation.

Prepare two sets of HDL serial dilutions. For each set take 20 μg (100 μL) of HDL and make serial dilutions (10 μg, 5 μg, and 2.5 μg) to a final volume of 50 μl in each tube. Add 100 μL PBS to all tubes. The new volume in all tubes should be 150 μL. To each tube in the first set add 100 μL PBS buffer. This will be the "HDL alone" treatment. To each tube in the second set add 100 μL of the LDL+Ox-PAPC mixture. This will be the "HDL+LDL+ox-PAPC" treatment. In a separate tube, add 150 μL PBS to 100 μL of the "LDL+ox-PAPC" mixture. (Note: the final volume in each tube should now be 250 μL). Incubate both sets for 30 minutes at 37° C.

Re-isolation of HDL

Re-isolate HDL as described above under the "HDL Isolation with Magnetic Bead Reagent" section. Add DCF to all tubes following Table 2. Incubate at 37° C. for 30 minutes. Read in a plate reader at an excitation of 485, emission of 530, and cutoff of 515 nm.

TABLE 2

Allocation of DCF and other components to assay tubes.

| Samples | PBS | HDL | LDL + Ox-PAPC | DCF | Total |
|---|---|---|---|---|---|
| DCF alone | 450 | | | 50 | 500 |
| LDL + ox-PAPC alone | 350 | | 100 | 50 | 500 |
| HDL (10 µg) alone | 200 | 250 | | 50 | 500 |
| HDL (5 µg) alone | 200 | 250 | | 50 | 500 |
| HDL (2.5 µg) alone | 200 | 250 | | 50 | 500 |
| Reisolated HDL (10 µg) | 200 | 250 | | 50 | 500 |
| Reisolated HDL (5 µg) | 200 | 250 | | 50 | 500 |
| Reisolated HDL (2.5 µg) | 200 | 250 | | 50 | 500 |

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

tically significant change in the amount of oxidized phospholipid indicates the mammal is at risk for atherosclerosis.

2. The method of claim 1, wherein said oxidized phospholipid is an oxidized phospholipid that causes a monocytic reaction.

3. The method of claim 2, wherein said phospholipid is an oxidized form of a lipid selected from the group consisting of 1-palmitoyl-2-arachidonoyl-sn-glycero-3-phosphorylcholine (Ox-PAPC), 1-palmitoyl-2-oxovaleroyl-sn-glycero-3-phosphorylcholine (POVPC), 1-palmitoyl-2-glutaroyl-sn-glycero-3-phosphorylcholine (PGPC), 1-palmitoyl-2-epoxyisoprostane-sn-glycero-3-phosphorylcholine (PEIPC), 1-stearoyl-2-arachidonoyl-sn-glycero-3-phosphorylcholine (SAPC), 1-stearoyl-2-oxovaleroyl-sn-glycero-3-phosphorylcholine (SOVPC), 1- stearoyl-2-glutaroyl-sn-glycero-3-phosphorylcholine (SGPC), 1-stearoyl-2-epoxyisoprostane-sn-glycero-3-phosphorylcholine (SEIPC), 1-stearoyl-2-arachidonyl-sn-glycero-3-phosphorylethanolamine (Ox-SAPE), 1-stearoyl-2-oxovaleroyl-sn-glycero-3-phosphorylethanolamine (SOVPE), 1-stearoyl-2-glutaroyl-sn-glycero-3-phosphorylethanolamine (SGPE), and 1-stearoyl-2-epoxyisoprostane-sn-glycero-3-phosphorylethanolamine(SEI PE).

4. The method of claim 1, wherein said oxidized phospholipid is ox-PAPC.

5. The method of claim 1, wherein said providing comprises removing non-HDL cholesterol from said sample.

What is claimed is:

1. A method of evaluating the risk for atherosclerosis in a mammal, said method comprising:

providing a biological sample from said mammal comprising a high-density lipoprotein (HDL);

contacting the high-density lipoprotein with an oxidized phospholipid combined with a low density lipoprotein (LDL); and measuring a change in the amount of oxidized or non-oxidized phospholipid wherein the absence of a statis- 6. The method of claim 5, wherein said providing comprises removing non-HDL cholesterol from said sample using a magnetic bead reagent.

7. The method of claim 1, wherein said providing comprises isolating the HDL from a blood sample.

8. The method of claim 1, wherein said measuring comprises a method selected from the group consisting of mass spectrometry, liquid chromatography, thin layer chromatography, fluorimetry, radioisotope detection, antibody detection, and detecting a signal from a label that indicates an oxidized phospholipid.

9. The method of claim 8, wherein said measuring comprises detecting a signal from a fluorescent indicator.

10. The method of claim 9, wherein said indicator is selected from the group consisting of 2',7'-dichlorodihydrofluorescine diacetate, rhodamine, cis-parinaric acid, NBD, cis-parinaric acid cholesteryl ester, dichlorofluorescein diacetate (DCFH-DA), and diphenylhexatriene propionic acid.

11. The method of claim 9, wherein said indicator is 2'7'-dichlorodihydrofluorescine diacetate (DCFH-DA).

12. The method of claim 8, wherein said measuring comprises fast performance liquid chromatography (FPLC).

13. The method of claim 1, wherein said biological sample is whole blood.

14. The method of claim 1, wherein said biological sample is a blood fraction.

15. The method of claim 1, wherein said biological sample is serum.

16. The method of claim 1, wherein said measuring comprises comparing said change in the amount of oxidized phospholipid with the change in amount of oxidized phospholipid produced by contacting the oxidized phospholipid with HDL known to reduce levels of oxidized phospholipid.

17. The method of claim 1, wherein said measuring comprises comparing said change in the amount of oxidized phospholipid with the change in amount of oxidized phospholipid produced by contacting the oxidized phospholipid with HDL known to be deficient in the ability to reduce levels of oxidized phospholipid.

18. The method of claim 1, wherein said measuring comprises comparing said change in the amount of oxidized phospholipid with the change in amount of oxidized phospholipid produced by performing the same method without an HDL.

19. The method of claim 1, wherein said mammal is selected from the group consisting of humans, non-human primates, canines, felines, murines, bovines, equines, porcines, and lagomorphs.

20. The method of claim 1, wherein said mammal is a human.

21. The method of claim 1, wherein said mammal is a human diagnosed as having a low HDL:LDL ratio.

22. The method of claim 1, wherein said mammal is a human diagnosed as being at risk for atherosclerosis by a different method.

23. The method of claim 1, wherein:
said biological sample is serum; and
said measuring comprises detecting a fluorescent indicator.

24. The method of claim 23, wherein said fluorescent indicator is 2'7'-dichlorodihydrofluorescine diacetate DCFH-DA.

25. The method of claim 24, wherein said oxidized phospholipid is 1-palmitoyl-2-arachidonoyl-sn-glycero-3-phosphorylcholine (Ox-PAPC).

* * * * *

SEQUENCE LISTING

```
<160> NUMBER OF SEQ ID NOS: 1

<210> SEQ ID NO 1
<211> LENGTH: 37
<212> TYPE: PRT
<213> ORGANISM: Artificial
<220> FEATURE:
<223> OTHER INFORMATION: Synthetic  apo A-I peptide mimetic

<400> SEQUENCE: 1

Asp Trp Leu Lys Ala Phe Tyr Asp Lys Val Ala Glu Lys Leu Lys Glu
1               5                   10                  15

Ala Phe Pro Asp Trp Leu Lys Ala Phe Tyr Asp Lys Val Ala Glu Lys
            20                  25                  30

Leu Lys Glu Ala Phe
        35
```